United States Patent [19]

MacKenzie et al.

[11] Patent Number: 6,020,127
[45] Date of Patent: Feb. 1, 2000

[54] NEURONAL APOPTOSIS INHIBITOR PROTEIN, GENE SEQUENCE AND MUTATIONS CAUSATIVE OF SPINAL MUSCULAR ATROPHY

[75] Inventors: Alex E. MacKenzie; Robert G. Korneluk; Natalie Roy, all of Ottawa, Canada; Mani S. Mahadevan, Madison, Wis.; Michael McLean, Guelph, Canada; Joh-E Ikeda, Tokyo, Japan

[73] Assignees: The University of Ottawa, Canada; Research Development Corp. of Japan, Japan

[21] Appl. No.: 08/836,134

[22] PCT Filed: Oct. 17, 1995

[86] PCT No.: PCT/CA95/00581

§ 371 Date: Jun. 20, 1997

§ 102(e) Date: Jun. 20, 1997

[87] PCT Pub. No.: WO96/12016

PCT Pub. Date: Apr. 25, 1996

[51] Int. Cl.[7] .............................. C12Q 1/68; C12P 19/34; G01N 33/53; C07H 21/04
[52] U.S. Cl. .............................. 435/6; 435/7.1; 435/91.2; 536/23.1; 536/24.5; 536/24.51; 536/24.33; 530/350; 530/387.1; 530/387.9; 530/388.15; 935/77; 935/78
[58] Field of Search ................................ 435/6, 7.1, 91.2; 536/23.1, 24.3, 24.31, 24.33; 530/350, 387.1, 387.9, 388.1, 388.15; 935/77, 78

[56] References Cited

U.S. PATENT DOCUMENTS 5,882,868   3/1999   Funanage et al. ..................... 435/6

FOREIGN PATENT DOCUMENTS

WO92/00386   9/1992   WIPO.

OTHER PUBLICATIONS

Soares et al.; "Refinement of the Spinal Muscular Atrophy Locus to the Interval between D5S435 and MAP1B"; *Genomics*, 15:365–371 (1993).

Francis et al.; "A contig of non–chimaeric YACs containing the spinal muscular atrophy gene in 5q13"; *Human Molecular Genetics*, 2(8):1161–1167 (1993).

Gilliam; "Is the Spinal Muscular Atrophy gene found?"; *Nature Medicine*, 1(2):124–127 (1995).

Roy et al.; "The Gene for Neuronal Apoptosis Inhibitory Protein is Partially Deleted in Individuals with Spinal Muscular Atrophy"; *Cell* 80:167–178 (1995).

Mahadevan et al.; "SMA genes: deleted and duplicated"; *Nature Genetics*, 9(2):112–113 (1995).

Shutler et al.; "Characterization of a cDNA clone that maps to the critical spinal muscular atrophy (SMA) locus region of 5q13"; *Amer. J. of Human Genetics*, 55(3):A327; Abstract #1919 (1994).

*Primary Examiner*—Stephanie Zitomer
*Attorney, Agent, or Firm*—Alston & Bird LLP

[57] ABSTRACT

The gene for the autosomal recessive neurodegenerative disorder Spinal Muscular Atrophy has been mapped to a region of chromosome 5. The gene encodes a protein having homology with apoptosis inhibitor proteins of viruses so that the encoded protein has been labelled as a neuronal apoptosis inhibitor protein (NAIP). A deletion in the (NAIP) domain was identified in persons with Type I, II and III Spinal Muscular Atrophy (SMA) and not in the normal non-SMA population.

33 Claims, 22 Drawing Sheets

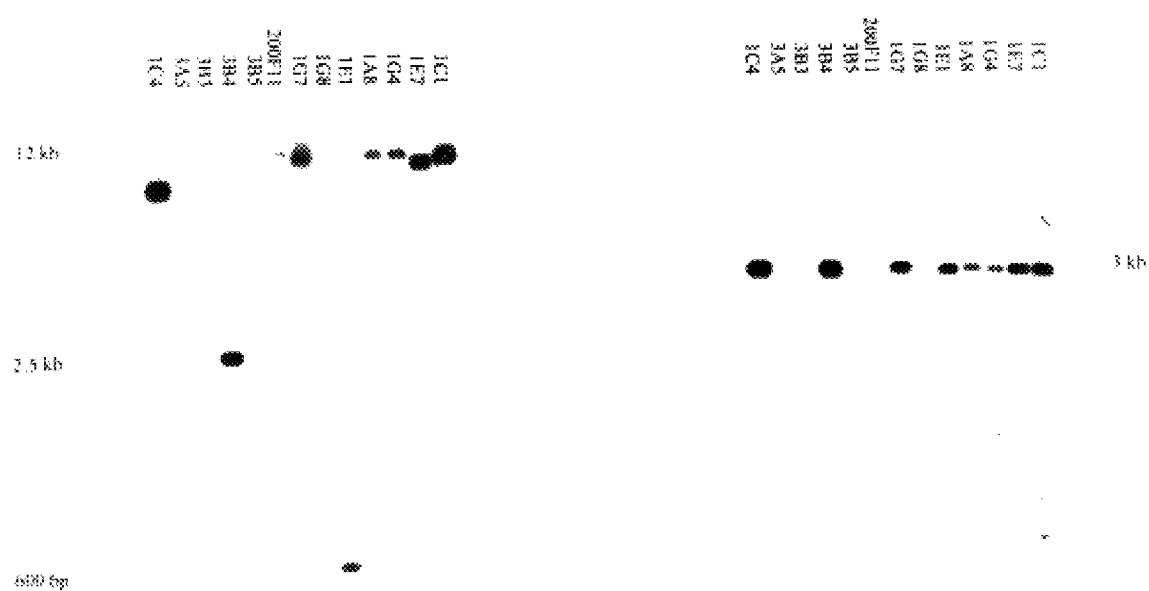

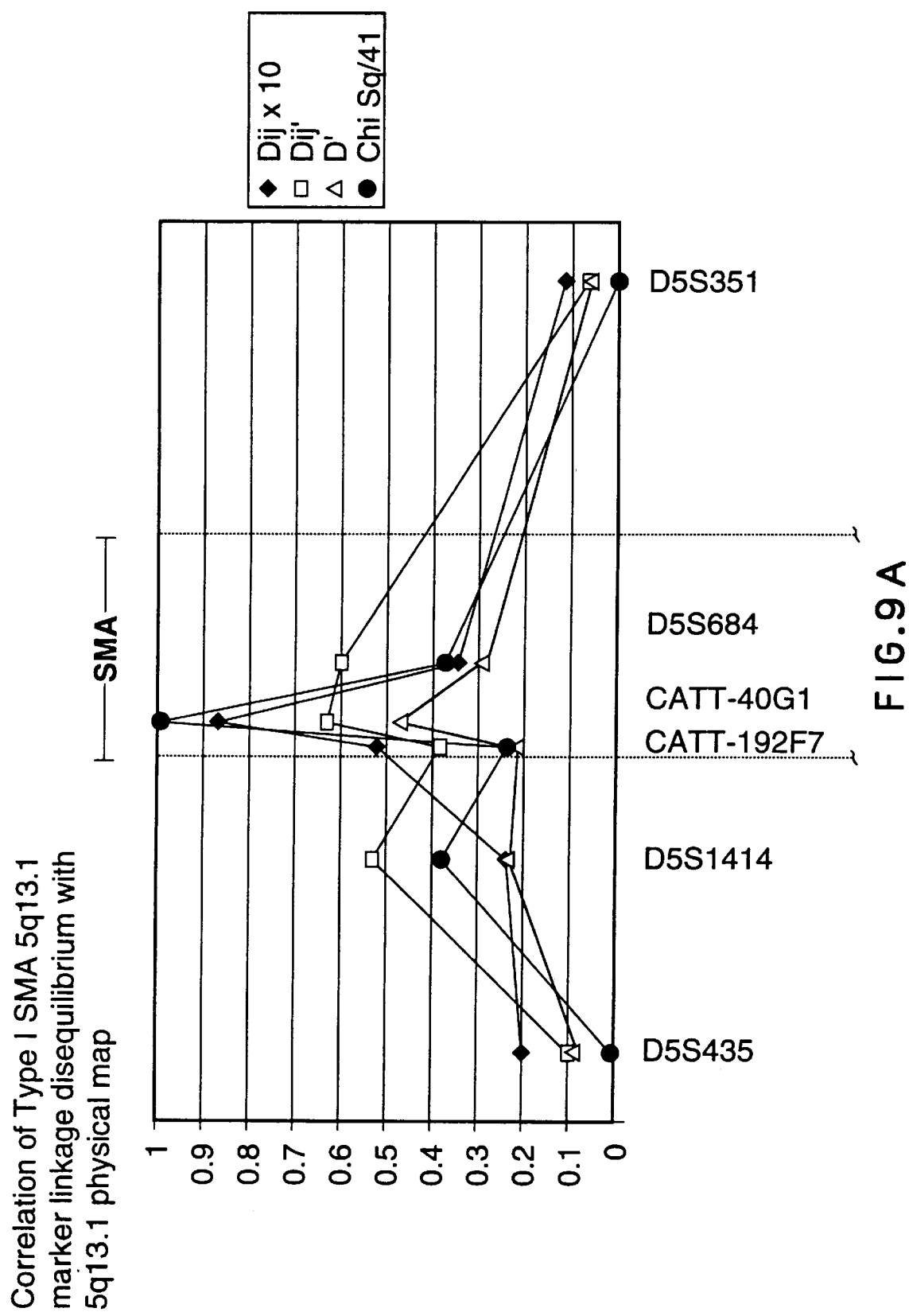

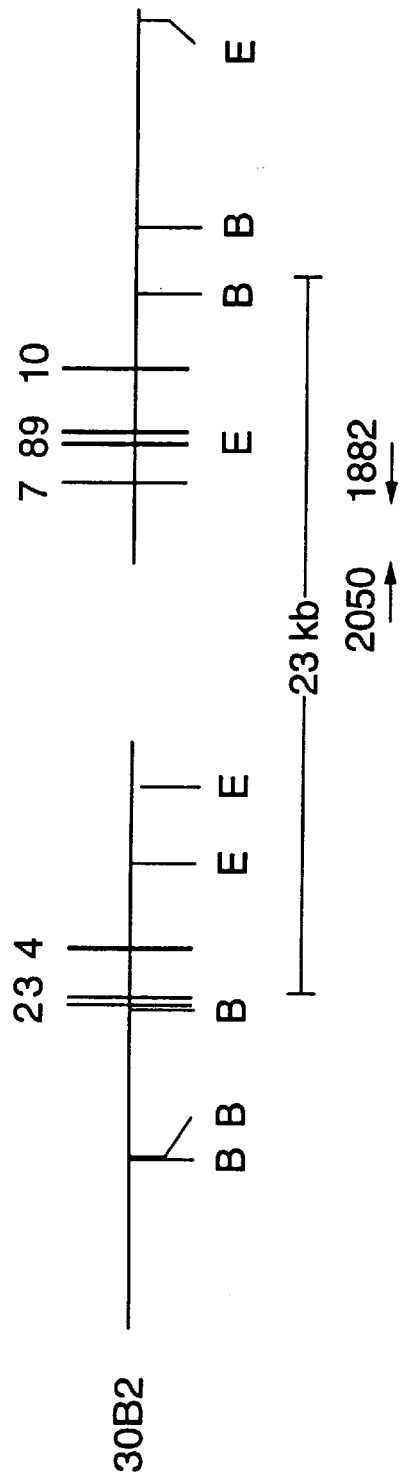
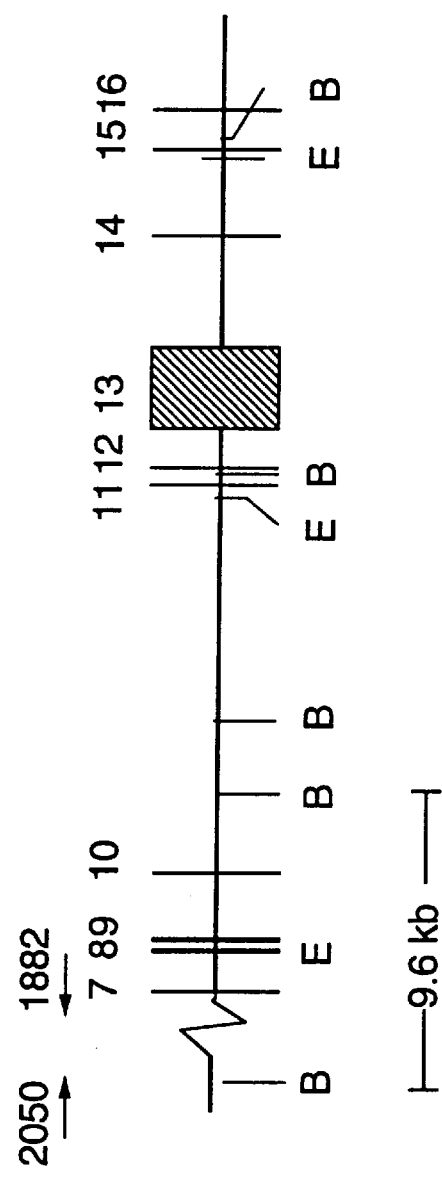
FIG.11C
FIG.11D

Splice Junctions of Exons of NAIP Mapping to PAC125D9

| Exon # | 3' Splice Junction | 5' Splice Junction |
|---|---|---|
| 0 | | |
| 1 | atgaag/ACAAAA | TCATCT/gtatcc |
| 2 | tgcgag/ACGACG | GCAAAG/gtgagt |
| 3 | ttttag/TTCCTT | CCTCAG/gtaagt |
| 4 | tttcag/AAAATG | TTACAG/gtacct |
| 5 | atatag/GTAAAC | |
| 6 | ttacag/ATGTGA | ATAACG/gtaatg |
| 7 | cctcag/GGAGAA | CATCAG/gtaaaa |
| 8 | ttccag/CTTATT | ACACAG/gtgagt |
| 9 | ttttag/GTATAA | TCCCAA/gtgagt |
| 10 | acttag/TTGTCC | TTACTG/gtaatg |
| 11 | tcaaag/GAAACC | TGCCAG/gtaaga |
| 12 | ccacag/AAATGG | CACAAG/gtatac |
| 13 | ttccag/ACCAAA | AACTAG/gtaagg |
| 14 | tcatag/TTGCCA | AATTTG/gtatgt |
| 15 | ctgcag/CCTACA | AAATTG/gtgagc |

FIG.12

FIG.15A. Family 24561    SCHEME 2.
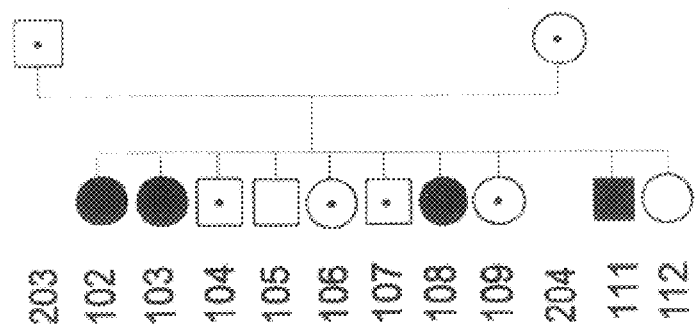
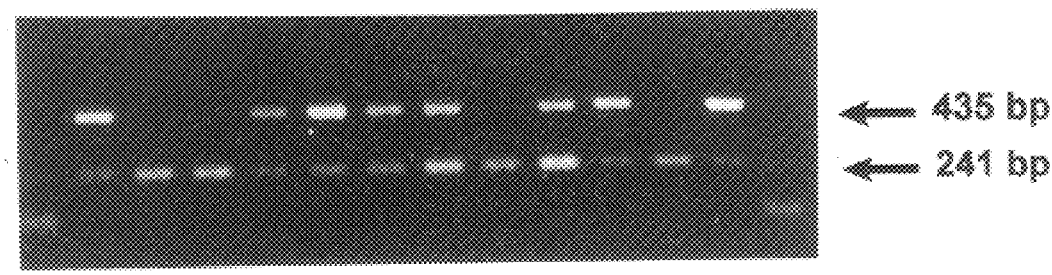
← 435 bp
← 241 bp
FIG.15B. Family 21470
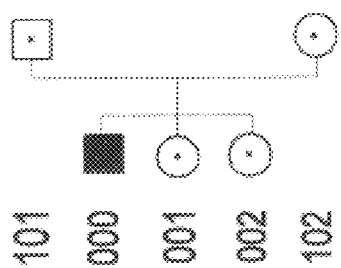
← 435 bp
← 241 bp

NEURONAL APOPTOSIS INHIBITOR PROTEIN, GENE SEQUENCE AND MUTATIONS CAUSATIVE OF SPINAL MUSCULAR ATROPHY

This application is a 371 of PCT/CA95/00581, filed Oct. 17, 1995, which claims priority to UK 9421019.2, filed Oct. 18, 1994 and CA 2,138,425, filed Dec. 29, 1994.

FIELD OF THE INVENTION

The gene for the neuronal apoptosis inhibitor protein (NAIP) has been identified in the q13 region of chromosome 5. Mutations in this gene have been diagnosed in individuals with Type I, II and III Spinal Muscular Atrophy. The amino acid sequence of the neuronal apoptosis inhibitor protein is provided and homology to viral apoptosis proteins demonstrated.

BACKGROUND OF THE INVENTION

In order to facilitate reference to various journal articles in the discussion of various aspects of this invention, a complete listing of the reference is provided at the end of the disclosure. Otherwise the references are identified in the disclosure by first author's name and publication year of the reference.

The childhood spinal muscular atrophies (SMAs) are a group of autosomal recessive, neurodegenerative disorders classified into three types based upon the age of onset and clinical progression (Dubowitz et al., 1978; Dubowitz et al., 1991). All three types are characterized by the degeneration of the alpha motor neurons of the spinal cord manifesting as weakness and wasting of the proximal voluntary muscles. Type I SMA is the most severe form with onset either in utero or within the first few months of life. Affected children are unable to sit unsupported and are prone to recurrent chest infections due to respiratory insufficiency, thus rarely surviving the first few years of life (Dubowitz et al., 1978; Dubowitz et al., 1991). This acute form, with a carrier frequency of 1/60 to 1/80, is one of the most frequent fatal autosomal recessive disorders. Affected children with Type II SMA never walk unaided and although the prognosis is variable, such children may die in adolescence. Those affected with Type III SMA maintain independent ambulation but develop weakness any time between the age of 3 to 17 years manifesting a mildly progressive course (Dubowitz et al., 1978; Dubowitz et al., 1991).

In 1990, all three childhood forms of SMA were genetically mapped to the long arm of chromosome 5 at 5q11.2–13.3 (Brustowitcz et al., 1990; Gilliam el al., 1990; Melki el al., 1990). Subsequent multi-point linkage analyses and the identification of recombinant events have further localized the genetic defect to the region flanked centromerically by D5S435/D5S629 (Soares et al., 1993; Wirth et al., 1993, Clermont et al., 1994)) and telomerically by MAP1B/D5S112 (Wirth et al., 1994; MacKenzie et al., 1993; Lien et al., 1991). This interval has been refined by the more recent identification of recombination events indicating that the SMA gene lies distal to CMS-1 (Yaraghi et al., submitted to *Human Genetics*; van der Steege, et al., submitted to *Human Genetics*) and proximal to D5S557 (Francis et al., 1993). We and others have detected chromosome 5-specific repetitive sequences with particular abundance in the D5S629/CMS-D5S557 region (Francis et al., 1993; Thompson et al., 1993) which has impeded the isolation and ordering of both clones and simple tandem repeats. An array of cosmid clones spanning the 200 kb CMS-1 (Kleyn et al., 1993)/CATT-1 (Burghes et al., 1994, McLean et al., in press)/D5F150/D5F149/D5F153 (Melki et al., 1994) region within this interval has been constructed.

We established a contiguous array of YAC clones encompassing the SMA containing D5S435-D5S112 interval of 5q13.1. We then discovered a gene within this interval of 5q13.1 which coded for a neuronal apoptosis inhibitor protein (NAIP). Further studies demonstrated that a deletion in this gene was found in Type I, II and III Spinal Muscular Atrophy.

SUMMARY OF THE INVENTION

A gene encoding a neuronal apoptosis inhibitor protein (NAIP) was discovered in the q13 region of human chromosome. According to an aspect of the invention, the cDNA sequence coding of the neuronal apoptosis inhibitor protein is provided and set out in Table 4 (SEQ ID NO: 1). According to another aspect of the invention, the predicted amino acid sequence of the neuronal apoptosis inhibitor protein is provided from the cDNA sequence.

According to another aspect of the invention, a deletion of the neuronal apoptosis inhibitor protein gene was discovered in persons with Type I, II and III Spinal Muscular Atrophy disease. The discovery of the neuronal apoptosis inhibitor protein gene deletion provides a diagnostic indicator for use in the diagnosis of Spinal Muscular Atrophy.

In order to facilitate a further description of various aspects of the invention, reference will be made to various Figures of the drawings. A brief description of the drawings follows this invention summary section.

According to a further aspect of the invention, a human gene is provided which maps to the SMA containing region of chromosome 5q13. The gene comprises exons 1 through 17 of approximately 5.5 kb and having a restriction map for exons 2 through 11, as shown in FIG. 8.

According to a further aspect of the invention, exons 1 through 17 have a restriction map for exons 2 through 16, as shown in FIG. 9D.

According to another aspect of the invention, a human gene of the above aspects wherein exons 5 through 16 code for the NAIP protein having an amino acid sequence biologically functionally equivalent to the amino acid sequence of (SEQ ID NO: 2).

According to another aspect of the invention, the human gene of the above aspects have exons 5 through 16 with a cDNA sequence biologically functionally equivalent to the cDNA sequence of (SEQ ID NO: 1).

According to another aspect of the invention, a purified nucleotide sequence comprises genetic DNA, cDNA, mRNA, anti-sense DNA or homologous DNA corresponding to the cDNA sequence of SEQ ID NO: 1.

According to another aspect of the invention, a DNA molecule sequence coding for the NAIP protein having SEQ ID NO: 2.

According to another aspect of the invention, a purified DNA sequence consists essentially of DNA SEQ ID NO: 1.

According to another aspect of the invention, a purified DNA sequence consists essentially of a DNA sequence coding for amino acid SEQ ID NO: 2.

According to another aspect of the invention, a purified DNA sequence comprises at least 18 sequential base of SEQ ID NO: 1. DNA probes, PCR primers, DNA hybridization molecules and the like may be provided by using the purified DNA sequence of at least 18 sequential bases.

According to another aspect of the invention, use of the DNA sequences of the above aspects in the construction of a cloning vector or an expression vector.

According to another aspect of the invention, NAIP protein encoded by the above DNA sequences.

According to another aspect of the invention, NAIP protein comprising an amino acid sequence biologically equivalent to the amino acid sequence of SEQ ID NO: 2.

According to another aspect of the invention, NAIP protein consisting essentially of the amino acid sequence of SEQ ID NO: 2.

According to another aspect of the invention, NAIP protein fragment comprises at least 15 sequential amino acids of SEQ ID NO: 2.

According to another aspect of the invention, use of the above amino acid sequences in the production of hybridomas.

According to another aspect of the invention, a method is provided for analyzing a biological sample to determine the presence or absence of a gene encoding NAIP protein.

The method comprises:
i) providing a biological sample derived from the SMA containing region q13 of chromosome 5;
ii) conducting a biological assay to determine presence or absence in the biological sample of at least a member selected from the group consisting of:
a) NAIP DNA SEQ ID NO: 1, and
b) NAIP protein SEQ ID NO: 2.

DESCRIPTION OF DRAWINGS

The original numbering of exons for the NAIP gene begin with exon 0 and progressed through exon 16. This is identified in drawings as sequence numbering Scheme #1. However, for conventional exon numbering, it is preferable to begin with exon 1 and progress through to exon 17. This is now identified as sequence numbering Scheme #2.

FIGS. 9A, 9B, 9C, and 9D is a single page alignment of the information of FIGS. 6, 1, 7 and 8, respectively. FIG. 9(A) is a correlation of the degree of linkage disequilibrium observed in type I SMA families between the disease phenotype and six 5q13.1 markers with the physical map. The SMA containing interval defined by the key recombinations described in the text is shown. Note the proximity of the disequilibrium peak with the centromeric end of the recombinant defined SMA interval.

FIG. 9(B) is a YAC contiguous array covering the SMA region of 5q13.1. For both YAC and PAC contigs, STSs are denoted by solid triangles, polymorphic tandem repeat polymorphisms by empty triangles, single copy clones by solid squares. Note that our physical map places the CMS sub locus containing allele 9, marked with an asterisk telomeric to the other CMS subloci, while the reverse was observed with genetic recombination data, reflecting, we believe, the variation that exists in this region of 5q13.1.

FIG. 9(C) is a PAC contiguous array covering the SMA region of 5q13.1.

FIG. 9(D) is the gene structure of NAIP as provided in more detail in FIG. 8.

FIG. 11A, 11B, 11C and 11D: Structure of intact and internally deleted/truncated versions of the NAIP gene as found in the indicated PACs. In FIG. 11A, exons under Scheme #2 are marked as numbered black boxes. N refers to NotI sites, B to BamHI and E to EcoRI sites. The EcoRV clone that detects the 3 and 9.4 kb EcoRI bands referred to in the text is denoted by EV in FIG. 11B. The 4.8 kb EcoRI/BamHI band deleted in FIG. 14 is also depicted. The 6 kb region containing exons 5 and 6 (Scheme #2) and the 23 kb BamHI fragment resulting from this deletion are both shown in FIGS. 11C and 1D. The location of primers utilized to identify deletions of exon 5 and 6 as well as those that identify the truncated fragment in the deleted NAIP gene are shown above the NAIP structure.

FIG. 12; Intron/exon splice sequences of the NAIP gene.

FIG. 15: Results of PCR amplification in type 3 families 21470 and 24561 using primers 1864 and 1863 which amplify exon 5 (Scheme #2). The reactions were multiplexed with exon 13 (Scheme #2) primers 1258 and 1343 to rule out PCR failure obscuring the results. Failure of amplification in keeping with the homozygous absence of exon 5 (Scheme #2) can be seen to co-segregate with the disease phenotype.

Figure 1:
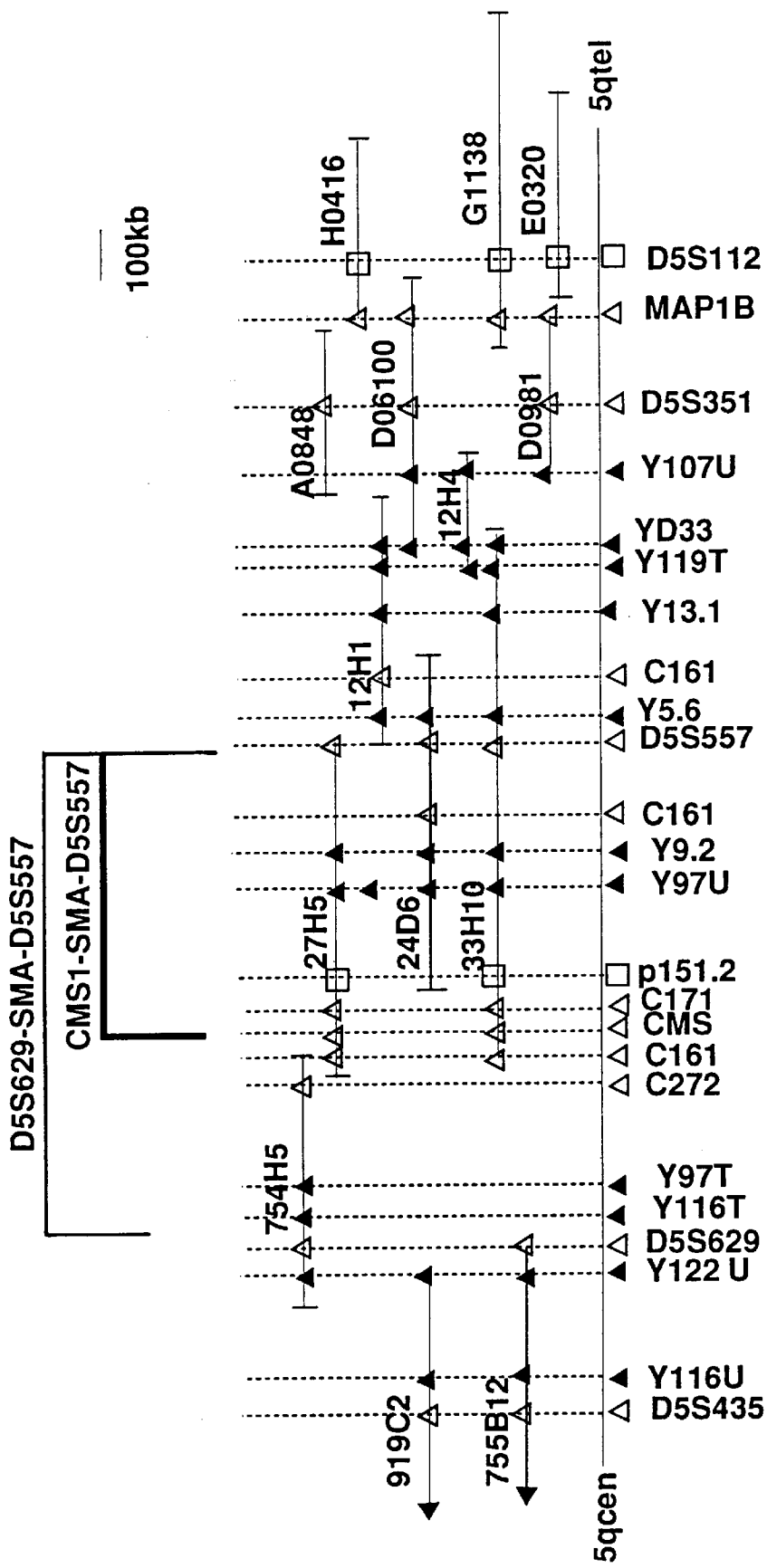
FIG. 1: YAC contiguous assay of the SMA gene region. YACs are represented by solid lines. Open triangles represent polymorphic STRS, solid triangles represent STSS, open squares represent single copy probes. The genetically defined SMA interval, CMS-1-SMA-D5S557 and the previous D5S629-SMA-D5S557 interval, are indicated above the YACS.

RNA was reverse transcribed from exon 13 (Scheme #2). Primary PCR of products shown in panels A and B was with exon 1 primer 1884 and exon 13 primers 1285 or 1974 and those in panel C with exon 6 primer 1919 and exon 13 primer 1285. Secondary PCR reactions for panel A used exon 4 primer 1886 and exon 13 primer 1974; for panel B, exon 5 primer 1864 and exon 11 primer 1979 and for panel C, exon 9 primer 1844 and exon 13 primer 1974.

Failure or amplification of reduced products can be seen in panel A for spinal cord and lymphoblast tissue for samples a2, a3, a4, a5, a6 and a7. Panel B also shows amplification of reduced size bands in a2 and a3, and in a7 a larger product in keeping with an insertion. Panel C shows reduced band size in keeping with deletions of exons 11 and 12 (Scheme #2) in a2, a3, a9 and a11.

DETAILED DESCRIPTION OF THE PREFERRED EMBODIMENTS

Unless indicated otherwise, reference to exons in this detailed description of the invention will be based on exon numbering Scheme #2.

Figure 8:
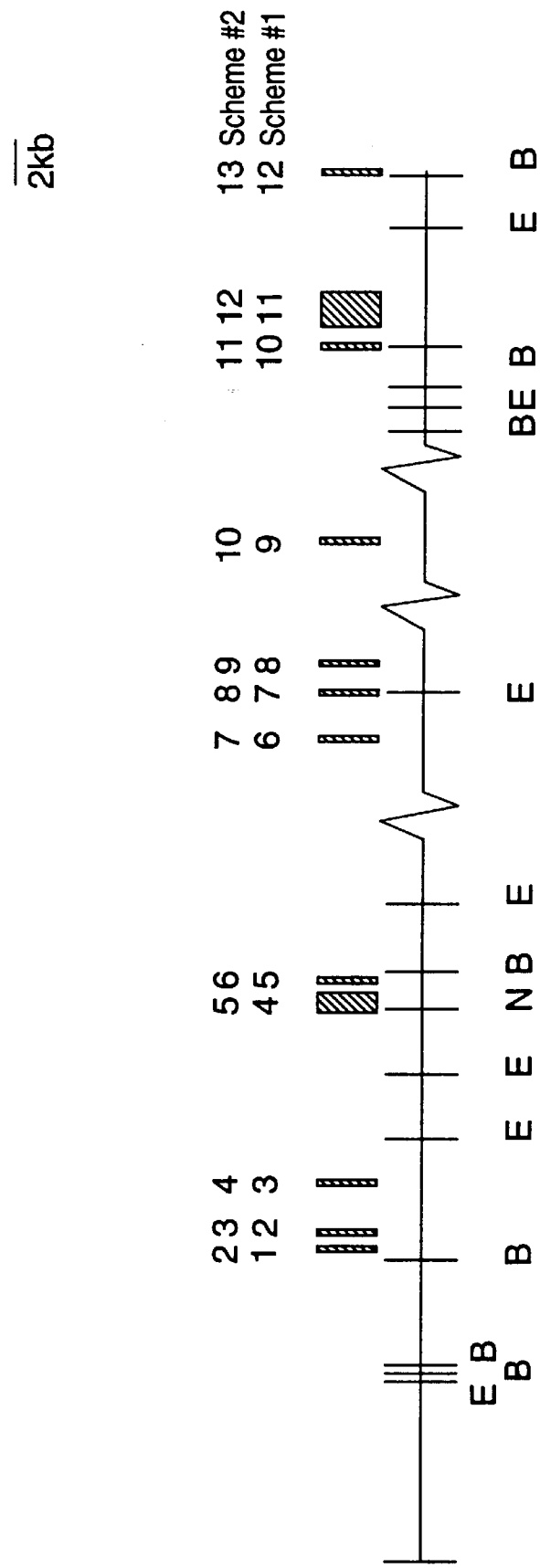
FIG. 8: Structural organization of the SMA gene. The exons are represented by black boxes and numbered above. The positions of restriction sites are shown: B, BamHI; E, EcoRI; N, NotI, Exons 4 and 5 (Scheme #1) or Exons 5 and 6 of Scheme #2 are frequently deleted in all types of SMA.
Figure 11A:
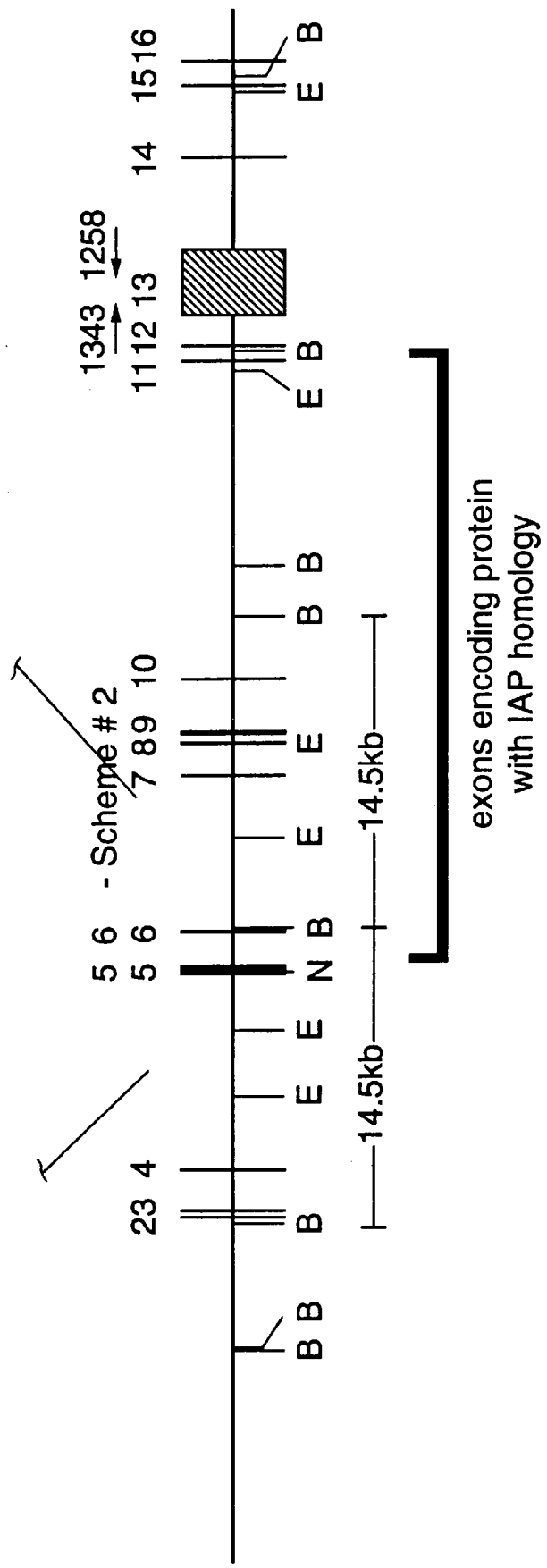

Throughout the specification, various letter abbreviations will be used to identify various components or techniques. The following glossary is provided to reference these items.
CTR—complex tandem repeat
DNA—deoxyribonucleic acid
PCR—polymerase chain reaction
PFGE—pulsed field gel electrophoresis
PAC—P1 artificial chromosome
RNA—ribonucleic acid
RT-PCR—reverse transcriptase-polymerase chain reaction
STR—simple tandem repeat
STS—sequence tag site
YAC—yeast artificial chromosome This invention is directed to the identification, location and sequence characteristics of a gene which encodes Neuronal Apoptosis Inhibitor Protein (NAIP). We have established that mutations in this gene are causative of the previously discussed types I, II and III of Spinal Muscular Atrophies (SMA). It is believed that mutations in this gene result in the lack in the production of normal NAIP protein which is believed to be physiologically involved in the normal human process of maintaining neurological cells and preventing their early death common to affected individuals. The subject gene maps to the SMA containing region of chromosome 5q13.1. Unless indicated otherwise, reference to exons in this detailed description of the invention will be based on exon numbering Scheme #2. The gene comprises exons 1 through 17 of approximately 5.5 kb and has a restriction map for exons 2 through 11, as shown in FIG. 8. An updated restriction map for exons 2 through 16 is provided in FIGS. 9D and 11A. As is appreciated, the gene is considerably longer than the sequence for exons 1 through 17. Considerable intron information exists between the exons which has not yet been sequenced. From the standpoint of diagnosing SMA, the sequence information of exons 1 through 17 is very valuable. The normal sequence is provided in Table 4, as well as being listed under SEQ ID NO: 1. Any genetic mutation, that is, changes in the DNA sequence, whether they be due to deletion, entire absence of gene substitution or polymorphisms and the like, are or can be causative of the disease. The most common mutations are thought to be:
  i) deletion of exons 5, 6 of the gene; or
  ii) absence or marked reduction in the copy number of this gene in the chromosome 5 can be causative, if the remaining genes are defective.

Any form of biological assay may be employed to diagnose a person's susceptibility to SMA by virtue of conducting a biological assay to determine the normal sequence or absence or presence of mutations in the normal sequence. Such biological assays may include DNA hybridization by use of DNA probes and the like, restriction enzyme analysis, PCR amplification of the relevant portions of the sequence, messenger RNA detection and DNA sequencing of the relevant portions of the sequence, as isolated from chromosome 5 of the human biological sample. It is appreciated that a variety of the above generally identified biological assay procedures may be conducted where the preferred techniques are as follows:

SMA diagnoses will be conducted in two ways. Initially, the genome of the human at risk will be assayed for the absence of NAIP exons 5 and 6. These exons are found to be absent with a frequency of 0.05% in the general population and 50% in Type 1 SMA. The second approach will be to assess the number of copies of the NAIP gene in the individuals being tested. We have observed that there is a general depletion of both deleted and intact forms of the NAIP gene, in individuals with SMA. By using a densitometric approach to assess the number of gene copies, an accurate assessment of the risk having SMA can be established. The best correlation is observed for exons 2 through 4 and exon 13.

In practical terms, the two steps outlined above will be conducted in the following manner:

(i) two concurrent PCR reactions will be carried out upon the same aliquot of DNA (0.1 micrograms) from the human in question. One primer pair will map into exons 5 and 6 (e.g. primers 1863 SEQ ID NO: 7 and 1864 SEQ ID NO: 8) and one pair will be homologous to a region outside of exons 5 and 6 (primers 1343 SEQ ID NO: 5 and 1258 SEQ ID NO: 4). The latter reaction will be performed to ensure that the PCR is functioning. Two additional controls will be (i) PCR performed on genomic DNA known to contain exons 5 and 6 employing the appropriate primers to ensure that this particular reaction is working, (ii) negative controls using water as a template to ensure absence of contamination. All PCR products will be placed in an agarose gel, separated electrophoretically and analyzed visually.

(ii) Densitometric assessment of SMA risk will be carried out by using PCR primers tagged with fluorescent dyes. PCR reactions employing primers for exons 2 through 4, exons 13 as well as exons 5, 6 and exons 11, 12 will be performed on genomic DNA from the individual being assessed. PCR products will be separated electrophoretically on a gel and the intensity of the individual bands assessed fluorometrically. These values will be correlated with normative values and SMA risk thus ascertained.

It is apparent that one's level of NAIP correlates with the risk for other neurodegenerative disorders such as amyotrophic lateral sclerosis and Alzheimers. Consequently, the tests outlined above serve as predictors of risk for these disorders as well. As is described in more detail in the section under heading Baculoviral IAPs, the NAIP protein has significant homology with proteins for inhibiting cell apoptosis. Hence, any neurodegenerative disease which is based on neuronal cell apoptosis can now be predicted by use of the DNA sequence information of the NAIP gene. Such neuronal cell apoptosis is most likely linked to mutations in the NAIP gene similar to the mutations associated with SMA or other mutations in the gene which affect the biological activity of the NAIP protein inhibiting neuronal apoptosis.

As to mRNA detection we propose the following:

RT-PCR is a rapid technique for the analysis of RNA transcripts which is a crucial part of several molecular biology applications. This method is much more sensitive and efficient than traditional Northern blot, RNA dot/slot blots, and in situ hybridization assays. The sensitivity of such a technique allows one to study RNA transcripts of low abundance or RNA isolated from small amounts of cells. In addition, an entire panel of transcripts can be analyzed simultaneously.

Protocol Summary: RNA is first isolated from tissues or cells and then is used as a template for reverse transcription to complimentary DNA (cDNA). The reverse transcription (RNA-directed synthesis of DNA), is catalyzed by the enzyme reverse transcriptase. The cDNA is then used as the template for PCR using primers designed to amplify a selected cDNA region. Following PCR, the product is analyzed by agarose gel electrophoresis. The amplified cDNA is identified by the size of the PCR product which is predicted from knowledge of the cDNA nucleotide sequence. The PCR product can be further validated by restriction digestion, hybridization or nucleotide sequencing.

Enzymatic Amplification of RNA by PCR (RT-PCR)

This method is used to enzymatically amplify RNA using PCR.

Detailed Protocol: First the primer is annealed to the RNA. The RNA and cDNA primer are coprecipitated by adding together poly(A)$^+$RNA, cDNA primer, and water. Sodium acetate is added and ethanol. This is precipitated overnight over $-20°$ C. The pellet is collected after microcentrifugation. The pellet is washed with ethanol. Then water, Tis-HCl, and KCl are added and the mixture is heated to $90°$ C. and then cooled slowly to $67°$ C. Microcentrifuge and incubate 3 hours at $52°$ C. This final annealing temperature may be adjusted according to base composition of primer. Alternatively, the primer can be annealed to the RNA by mixing poly(A)$^+$RNA, cDNA primer, and water. This mixture is heated 3 to 15 minutes at $65°$ C. To the cooled mixture, add reverse transcriptase buffer.

The cDNA is now synthesized. Add reverse transcriptase buffer and AMV reverse transcriptase. This is mixed and incubated 1 hour at $42°$ C. (depending on the base composition of primer and RNA). Add Tris-Cl/EDTA, mix then buffered phenol and vortex. Microcentrifuge and add chloroform to the aqueous phase and vortex. Microcentrifuge. Add sodium acetate and ethanol to aqueous phase. Mix and precipitate overnight at $-20°$ C. Microcentrifuge, dry pellet, and resuspend in water.

The cDNA is then amplified by PCR. The mixture contains prepared cDNA, amplification, dNTP mix, amplification buffer, and water. Usually one of the amplification primers is the same as cDNA primer. If a different amplification primer is used, the cDNA primer should be removed from the cDNA reaction. The reaction mixture is then heated 2 minutes at $94°$ C., and microcentrifuged to collect condensate. Add Taq DNA polymerase, mix, centrifuge, overlay with mineral oil. Set up amplification cycles. The number of cycles is varied depending upon the abundance of RNA. Forty cycles are usually sufficient. The products are then analyzed by gel electrophoresis in agarose or nondenaturing polyacrylamide gels. The cDNA can also be introduced directly into the amplification step.

In referencing the gene, its cDNA sequences, other DNA sequences and RNA sequences, it is understood that any specifically referenced sequence includes any and all biologically functional equivalence thereof. Similarly, with listed protein sequences, it is understood that such terminology includes any and all biologically functional equivalence thereof insofar as the intended purpose is concerned. In the above identified biological assays it is understood that the full length or partial length sequences of the DNA or protein may be used. Generally it is contemplated that at least 18 sequential bases of the DNA sequence are useful as hybridization probes, PCR primers and the like. Similarly, with protein sequences, at least 15 sequential amino acid sequences may be correspondingly useful in developing protein receptors such as monoclonal antibodies. Such monoclonal antibodies may be made in accordance with the standard techniques by developing hybridomas for producing monoclonals specific to certain antigenic determinants of the protein structure.

With reference to Table 4, it would appear that in view of the significant homology of exons 5, 6, 7, 8, 9, 10 11 and 12 with the IAP domains, such homology may well mean that any deletions or other forms of mutations in these exons may result in the carrier being susceptible to the disease. For example, this is evidenced by the deletion of exons 5 and 6 in low copy numbers in humans being causative of the disease. Hence, any of the sequence information in this region of the gene will be important from a diagnosis standpoint so that any sequential 18 bases of DNA or 15 sequential amino acid residues in this region may be relied on in the diagnosis of SMA in suspected humans. It is of course also understood that other forms of deletions, mutations, polymorphisms and the like in other regions of the gene may be causative of the disease or may be used for other purposes in conjunction with disease analysis, prognosis and perhaps treatment.

Although the restriction maps are useful in identifying the characterizing features of the subject gene the specific cDNA sequence of exons 1 through 17 has been provided in SEQ ID NO: 1. The encoding portion of the sequence commences at the ATG codon of base 396 of exon 5. The encoding portion ends at the stop codon TAA of exon 16 at base position 4092. Exons 1 through 4 are at the 5' untranslated region and exon 17 is at the 3' unstranslated region. As with some genetic related diseases, mutations or polymorphism in the untranslated regions may as well be causative of the disease so that sequence portions in the form of probes and the like in regions other than the region of significant IAP homology may be valuable in the diagnosis of SMA. It is also understood that the sequence information of SEQ ID NO: 1 may be used in the construction of suitable cloning vectors for purposes of producing multiple copies of the gene or expression vectors for purposes of transfecting a host to produce significant quantities by recombinant techniques of the NAIP protein. Sections or fragments or full-length sequence information may be used in the construction of the cloning vectors or expression vectors depending upon the end use of such vectors. With this understanding, the details in respect of the identification of the SMA disease gene its characteristics, the corresponding protein sequence and their uses in diagnosis are explained.

A YAC contig of the Spinal Muscular Atrophy (SMA) disease gene region along chromosome 5q13 was produced which incorporated the D5S435-D5S12 interval and encompassed 4 Megabases. The CATT-40G1 subloci on the cosmid array showed significant linkage disequilibrium with Spinal Muscular Atrophy indicating close proximity to the gene. However, delineation of the precise region containing the SMA gene was not possible based on this information alone. A PAC contiguous array containing the CATT region comprised of 9 clones and extending approximately 400 kb was constructed. The genetic analysis combined with the physical mapping data indicated that the 154 kb PAC clone 125D9 (FIG. 7) which contained the CMS allele 9 and the 40G1 CATT sublocus had a good probability for containing the SMA locus. Through further analysis as will be described, PAC 125D9 was found to contain the gene encoding neuronal apoptosis inhibitor protein.

pYAC (yeast artificial chromosome plasmids) allow direct cloning into yeast of contiguous stretches of DNA ≦400 kb. Circular pYAC plasmids (without inserts) can replicate in *E. coli*. In vitro digestion of pYAC, ligation to exogenous DNA, and direct transformation of the subsequent linear molecules (with telomeric sequences at each termini) into yeast generates a library that can be screened by standard techniques.

Large YAC constructs are as stable as natural chromosomes. They are good vectors for the construction of libraries from complex genomes such as the human genome. In addition, sequences which are unclonable in *E. coli* cosmid and lambda vectors are successfully cloned in YAC vectors.

YAC vectors are normally propagated in bacteria as circular plasmids. Restriction enzyme target sites are arranged to produce two arms upon digestion, each of which contains a different selectable marker and terminates at one end in a telomere, the other in a blunt end. In addition, one of the arms contains an ARS element. The two arms are purified away from a linking fragment and ligated with donor DNA fragmented so as to leave blunt ends. The ligation mixture is used to transform yeast cells, and the selection conditions are such as to require the presence of both arms, the insert interrupts a third selectable marker which allows non-recombinant structures to be recognized.

Construction of YAC Contig

YAC clones were isolated from three libraries, constructed at the National Centers of Excellence(NCE, Toronto), the Imperial Cancer Research Fund (ICRF, London) (Larin et al., 1991) and the Centre d'Etude du Polymorphisme Humaine (CEPH, Paris) (Albertson et al., 1990), all of which were prepared from partial EcoRI digests of total DNA ligated into the YAC vector pYAC4. ICRF YAC clones were identified by probing library filters with 5q13.1 probes. YAC DNA from the NCE library was screened by PCR amplification, electrophoresed, immobilized onto Southern blots and hybridized with the radiolabelled STS product to identify positives. Numerous positives were obtained repeatedly in both the initial round of PCR of pooled plates, and the second round with the plate(s) thought to contain the clone of interest many of which proved to be false positives. The number of false positives obtained, which appeared to be primer dependent, was reduced by radiolabelling PCR products and resolving these on 6% polyacylamide gels. The true positives could then be sized accurately without interference from spurious products.

Yeast strains with YACs positive for 5q13.1 STSs were grown on selective plates and examined for stability in the following manner: 4 colonies of each were grown for preparation in agarose blocks, yeast chromosomal DNA was separated by pulsed field gel electrophoresis and transferred to filters and the size and number of YAC clones contained within each yeast colony was determined by hybridization with radiolabelled total human genomic DNA. Positive clones were confirmed either by hybridization or PCR amplification with the original probe. Only YAC 24D6-2 contained some colonies with more than one YAC.

YAC end clones and inter-Alu products were isolated by vector-Alu PCR and inter-Alu PCR respectively. The location of these products within 5q11-13 was confirmed by hybridization to Southern filters of the somatic cell hybrids HHW105 (Dana et al., 1982), containing the entire chromosome 5, and HHW1064 (Gilliam et al., 1989), a derivative containing chromosome 5 with a deletion at 5q11.2-13.3. Many of these probes demonstrated hybridization profiles indicative of locations both within the 5q11-13 region and elsewhere on chromosome 5. In some cases primers specific for the ends of each YAC were generated from the sequences of YAC end clones isolated by vector-Alu-PCR. The mapping of each new STS to 5q11-13 was determined by PCR amplification of DNA from the somatic cell hybrids HHW105 and HHW1064. In a few cases it was found that a primer pair contained a chromosome 5 repetitive sequence as the PCR amplified products from both HHW1064 and HHW105 were positive. Formulation of new STS primers resulted in the amplification of products specific to the 5q11-13 region. End clone hybridization and STS analysis performed on all YACs confirmed the orientation and location of each YAC.

The assembly of a contiguous array of YACs covering the SMA interval was initiated from two markers which flank SMA; D5S125 (Mankoo et al., 1991), which lies centromeric to D5S435 and the more telomeric marker D5S112 (Lien et al., 1991) (see FIG. 1). Six YACs were identified in the ICRF library by the telomeric marker pJK53 (D5S112).

One of these YACs, D06100, was shown to extend the furthest centromerically based on end clone STS analysis. The centromeric end of this YAC identified two YACs from the NCE library, 1281 and 1284. YACs positive for the D5S125 or D5S435 markers were not found in the ICRF or NCE library thus the CEPH library was screened, from which clones containing D5S435 were isolated. A microsatellite polymorphism mapping into the center of the gap, CATT-1 (Burghes et al., 1994), was utilized to detect three YACS, 24D6-2, 27H5 and 33H10. These YACs were shown to be linked to both the centromeric and the telomeric YACs (1281, 1284) by STS analysis. Internal YAC products generated by AluPCR were utilized to probe all YACs establishing the degree of overlap. STS sequences (Kleyn et al., 1993) mapping between JK348 and D5S112 were utilized to confirm the degree of overlap and the orientation of YACs in the contig. Concurrently the order of each STS along 5q13 was confirmed. In all a total of 14 YACs were identified, anchored by the genetic markers D5S435, D5S629, CMS-1, CATT-1, D5F153, D5F149, D5F150, D5F151, D5S557 and D5S112.

Long Range Restriction Map and Estimation of Long range Physical Distance

Figure 2:
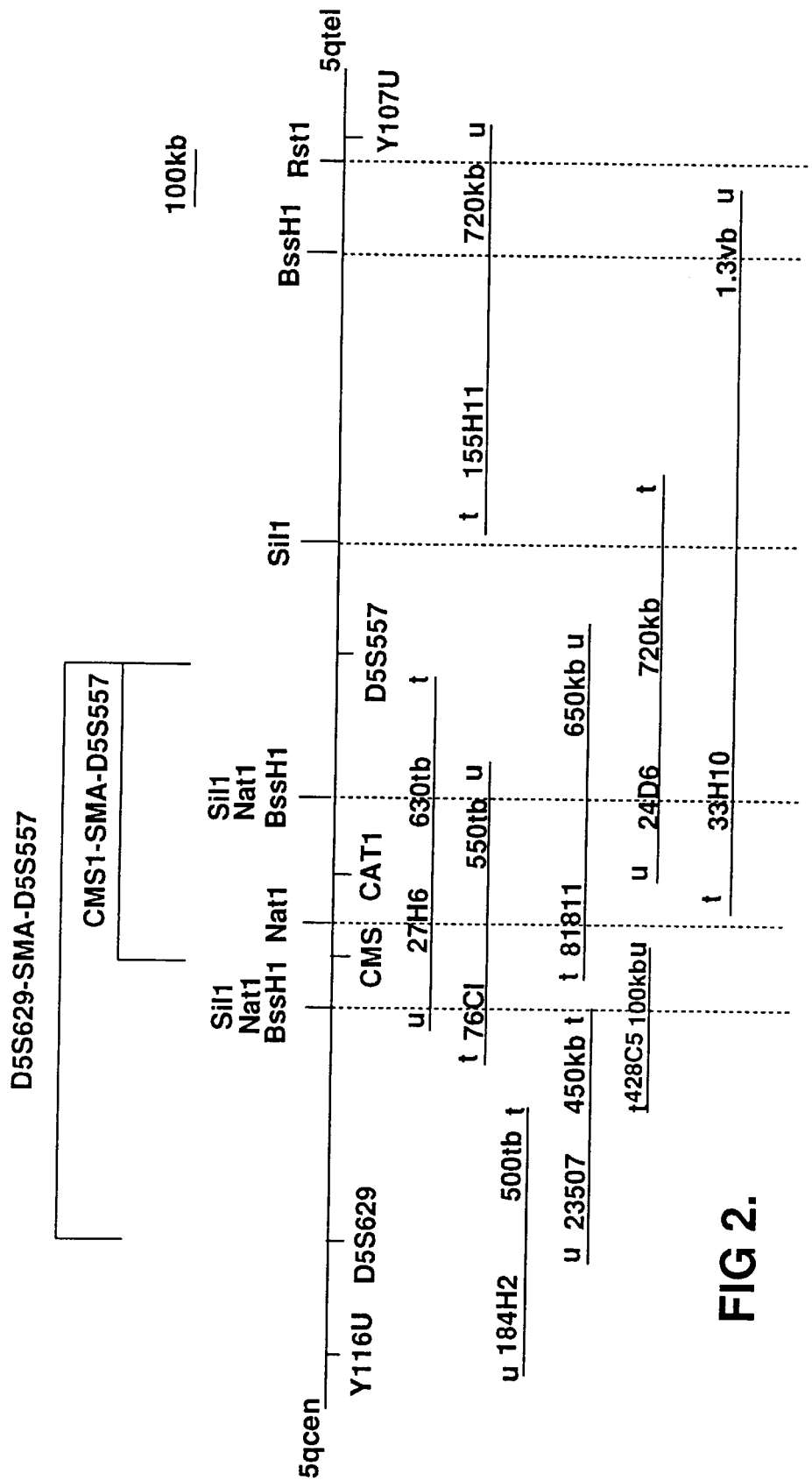
FIG. 2: Long range restriction map of the SMA region. Rare cutter sites are indicated above the solid line. A minimal set of markers are indicated below the solid line t corresponds to the pYAC4 tryptophan or left end. u corresponds to the pYAC4 uracil or right end. The genetically defined CMS-1-SMA-D5S557 and the D5S629-SMA-D5S557 interval are estimated at 550 kb and 1.1 Mb respectively.

A restriction map of the critical SMA region was constructed from the STS Y116U (Kleyn et al., 1993), approximately 100 kb proximal to D5S629, to the STS Y107U (Kleyn et al., 1993), which lies approximately 500 kb distal to D5S557 (see FIG. 2). In order to detect any possibility of deletions or rearrangements in our YACS, additional YACs isolated from the CEPH library (Kleyn et al., 1993), mapping within this region were included in the analysis. YACs 24D62, 27H5, 33H10, 155H11, 76C1, 235B7, 184H2, 428C5, and 81B11 (Kleyn et al., 1993) were partially digested utilizing the rare cutter restriction endonucleases NotI, BssHII, SfiI, and RsrI. Southern blots of the Pulse Field Gel Electrophoresis (PFGE) separated restriction products were hybridized with YAC left arm and right arm specific probes which revealed the positions of cleavage sites from both ends of each YAC. The orientation and overlap of the YACs had been previously determined based on STS analysis, therefore the position of the rare cutter sites among the overlapping YACs were compared. By aligning the overlapping YACs at their common rare cutter sites, the degree of overlap could be more precisely determined. The long range restriction map of the overlapping YACs derived from different sources was mostly in agreement with the exception of 33H10 and 428C5. 428C5 has previously been documented to contain a deletion (Kleyn et al., 1993), evident by comparison of its STS content and its size of only 300 kb, indicating that it lies further centromeric than its placement in FIG. 2. YAC 33H10, based on STS analysis contains an internal deletion and YAC 155H11 is chimeric at its telomeric end therefore rare cutter sites at the telomeric end of the map which could not be confirmed were not included. The results indicate the distance from the centromeric boundary D5S435 to the telomeric boundary D5S557 to be 1.4 Mb in marked contrast to 400 kb as previously reported (Francis et al., 1993) but in agreement with one other estimate (Wirth et al., 1993). Furthermore, the D5S629-D5S557 interval can be estimated at 1.1 Mb and the distance of the genetically defined CMS1-SMA-D5S557 interval is approximately 550 kb.

Cosmid Contig Assembly from the Chromosome 5 Library

Figure 3A:
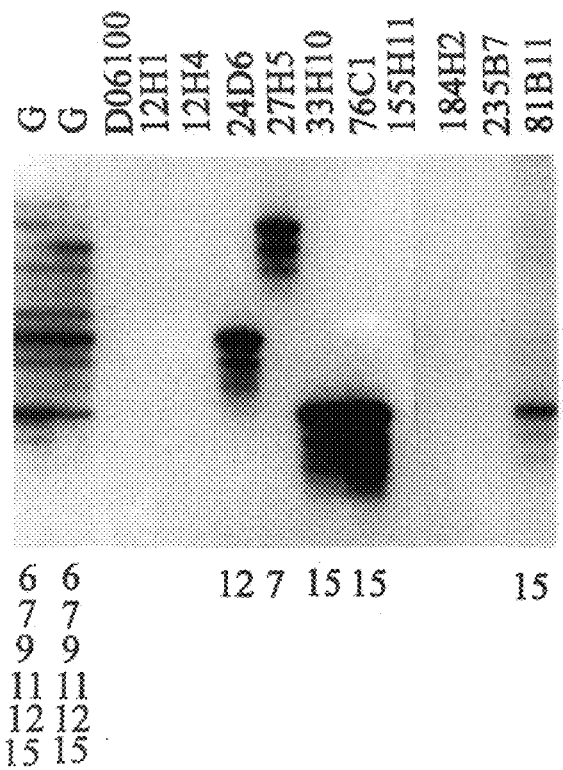
FIGS. 3A and 3B: Amplification of the CATT-I locus. Allele sizes are shown below each lane. (A) Amplification of YACS. G: genomic DNA. (B) Amplification of cosmids derived from the chromosome 5 flow sorted library. The 4 distinct alleles are represented by cosmids 40G1 (allele 15), 58G12 (allele 12), 192F7 (allele 10) and 250B6 (allele 7).
Figure 3B:
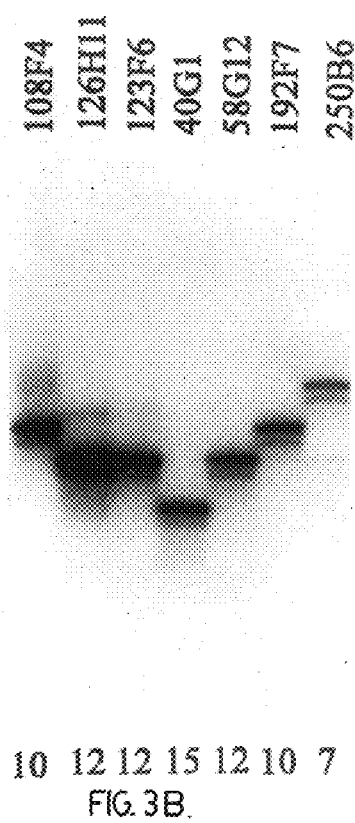
Figure 4:
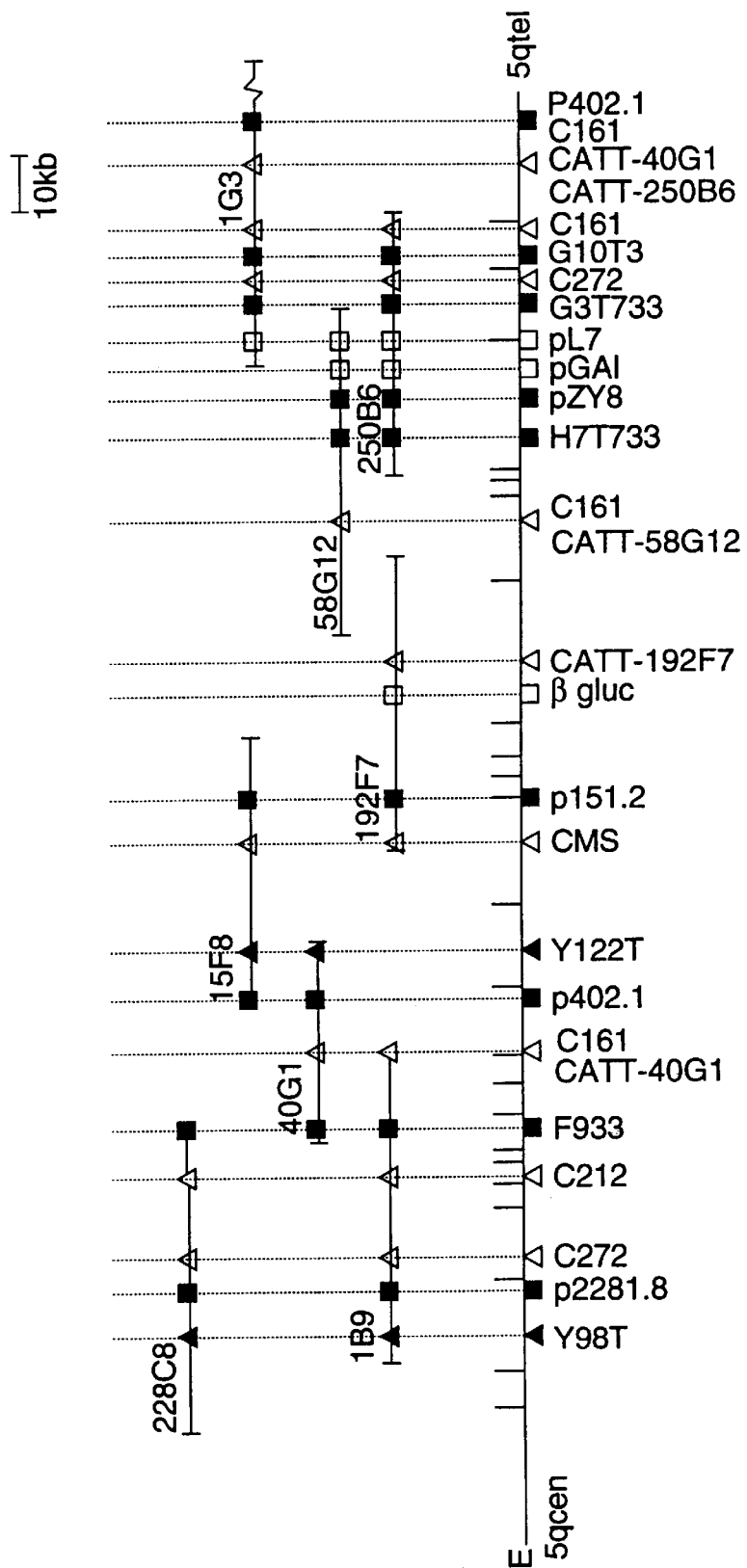
FIG. 4: A representative subset of mapped cosmids from our contiguous array. Vertical lines above the solid line are the positions of EcoRI sites. Open triangles represent polymorphic STRS, filled triangles represent STSS, filled squares represent single copy probes and open squares represent transcribed sequences. The STRs which demonstrate strong linkage disequilibrium with Type I SMA are indicated by stars. Cosmids IG3 and IB9 are from the YAC 76CI cosmid library.

Although the isolation of cosmids utilizing whole YACs as probes could be an expeditious method of constructing a cosmid contig, in this case the presence of chromosome 5 specific repeats would likely result in the isolation of cosmids mapping elsewhere on chromosome 5. A directed cosmid walking strategy was thus adopted. The CATT-1 STR, which has been shown by irradiation hybrid analysis to map approximately midway between the two flanking markers D5S435 and D5S351 (Hudson et al., 1992), was utilized as the initiation point for the construction of a cosmid clone array. The complex pattern of amplification seen on genomic DNA, with two to eight alleles per individual (see FIG. 3), suggested a variable number of copies or loci of the CATT-1 sequence in this region. Thirty CATT-1 positive cosmids were identified which upon PCR analysis were seen to contain one of four distinct alleles (see FIG. 3). As the cosmid library was derived from a monochromosomal source, this confirmed that the CATT STR exists at least in four locations, which we refer to as subloci. These subloci are referred to as CATT-40G1, CATT-192F7, CATT-58G12 and CATT250B6-based on the cosmid addresses of the first cosmids identified containing alleles of 12, 19, 15 and 20 cytosine adenosine (CA) dinucleotides respectively. Bi-directional walking was initiated from these 4 cosmid subloci. Positive hybridization was observed for cosmid 250B6 with one end of 58G12 and for 192F7 with the other end resulting in the ordering of cen-192F7-58G12-250B6-tel (FIG. 4). All cosmids which contained the CATT-192F7 allele were mapped to this location based on the size of their CATT-1 allele and their restriction enzyme profiles. As shown in FIG. 4 the CATT-192F7 sublocus is telomeric to the STR CMS-1, which itself lies telomeric to the CATT-40G1 sublocus.

Due to the presence of chromosome 5 specific repetitive sequences, resulting in the identification of cosmids from another region of chromosome 5, the integrity of the contig was verified with each step taken. Cosmid end clones generated by vector-Alu-PCR were hybridized to somatic cell hybrid panels as described above. As repetitive sequences which map solely to the region of chromosome 5 that is deleted in the hybrid cell line HHW1064 have been observed, cosmids identified by end products which did not hybridize to HHW1064 were analyzed further. Proof of overlap was shown by hybridization of end clones, single copy probe hybridization, STS content, and restriction enzyme profile comparison. Cosmids identified by end clones which hybridized to HHW1064 were eliminated and walking was continued by utilizing a different inter-Alu product from the clone of origin, which was verified in the same manner. Cosmid sizes were calculated by the addition of EcoRI restriction fragments and the extent of overlap was determined by the addition of those fragments in common.

Cosmid Contig Assembly of YAC 76C1 Cosmids

As extension of the cosmid contiguous array was prevented by the presence of chromosome 5 specific repeats, a 5× cosmid library was produced from YAC 76C1. The STSs CATT-1, CMS-1, Y122T (Kleyn et al., 1993), Y97T (Kleyn et al., 1993) and Y98T (Kleyn et al., 1993), which are distributed along the YAC were utilized to identify cosmids to assemble the contig. As well, the previously developed markers, pZY8, pL7, pGA-1, p15.1, p402.1, p2281.8 and β-glucuronidase (Oshima et al., 1987) (Table 2, FIG. 4) from the established cosmid contig were hybridized to the library providing an effective method of ordering the cosmids. Cosmids demonstrating irregular hybridization patterns and thought to contain deletions and/or rearrangements were excluded.

The STS Y98T identified three cosmids including one previously identified by the probe p2281.8, derived from a chromosome 5 library clone, 228C8, also containing the STS Y98T. An end product of this cosmid hybridized to ten cosmids. Concurrently, an end fragment of a CATT40G1 sublocus was shown to hybridize to four of these ten cosmids thus linking CATT-40G1 and CMS-1 with the more centromeric STS Y98T (FIG. 4). We were unable to identify any clones containing the YAC end STS Y97T. Filter hybridization and STS mapping experiments indicated a second more telomeric location of the CATT40G1 sublocus. A duplication of this sublocus would agree with genotype data in our SMA kindreds (McLean et al., in press).

An EcoRI restriction map was generated utilizing a minimal set of cosmids necessary to span the region. To ensure the reliability of the contig, we sought to integrate it with the contig constructed from the chromosome 5 specific library. Concordance of the contigs was evident by comparison of the restriction maps, the position of probes and STSs on the map and Alu-PCR fingerprinting. In this manner the size of the contig was estimated to be 210 kb. A directed walking strategy has thus resulted in the generation of a single contiguous set of cosmids containing the CATT-1 cluster of subloci with known centromere/telomere orientation.

Duplications/Deletions

Several lines of evidence suggested the presence of genomic sequence duplications within our cosmid array. We provide evidence for the duplication of the CATT-40G1 sublocus in cosmids derived from a single chromosome 5. A centromeric location for this sublocus established as the CATT-40G1 sublocus was found to be contiguous with the STSs Y122T, Y88T and CMS-1 in several cosmids, and the centromeric YAC 428C5 is positive for probes isolated from the CATT-40G1 containing cosmids. Although YAC 428C5 does not contain the CATT40G1 sublocus upon PCR amplification, this may be explained either by a null allele in the chromosome from which the YAC was derived or a deletion in the YAC. We have previously observed null alleles in individuals at distinct CATT-1 subloci. A second more telomeric location of CATT-40G1 was determined by the hybridization to CATT40G1 cosmids of the probes pGA-1, pL7, and pZY8 all of which bind the more telomeric YACs 33H10, 24D62. The hybridization of p402.1, derived from cosmid 40G1, to cosmids at both locations would indicate that the duplication is not restricted to the CATT-40G1 subloci and likely encompasses a larger region. Southern blot analysis revealed distinct profiles of cosmids for the two locations however common bands were detected by Alu-PCR fingerprinting supporting a duplication.

Correlation of our YAC contig with the cosmid contig revealed that YACs 76C1, 81B11, and 27H5 span the 150 kb CATT region of 5q13. Despite this, CATT-1 genotyping of these YACs revealed only one allele size, raising the possibility that the chromosomes from which these YACs were derived (4 in all) contain null alleles at their remaining CATT-1 subloci. Our experience, however, with CATT linkage analysis of SMA families indicated that such a scenario is highly unlikely as none of the approximately 300 individuals genotyped had fewer than 2 alleles. We consequently believe it is more likely that these CATT subloci are unstable and have been deleted during YAC construction and/or propagation.

Sequence comparison between the CATT-1 and D5F153 primer sequences indicated that these two STRs were similar and possibly the same as one primer is identical and the other primer sequences overlap by eight nucleotides. However, the centromeric YACs 428C5, 232F12, 235B7, 184H2, and the telomeric YACs 12H1, 155H11, 269A6 which were CATT-1 negative yielded D5F153 amplification products indicating that CATT-1 may be a derivative of D5F153. These data, in combination with D5F153 analyses of the cosmid contig, which contains three D5F153 loci (FIG. 4), indicated that at least five D5F153 subloci exist.

In addition to the CATT-1 and D5F153 STRs, the STRs CMS-1 and D5F150 were present in a variable number of copies per chromosome 5. STS analysis localized CMS-1 to YACs 428C5, 76C1, 81B11 and 27H5 with allele sizes of 5, 4, 4 and 3, and 4 respectively. PCR amplification of genomic DNA revealed up to four alleles per individual indicating as many as two copies per chromosome. D5F150 was present at two locations within the cosmid array yet only one location was detected in the YAC contig. D5F151 was not detected within our cosmid array nevertheless it was placed at the centromeric end of YAC 33H10, which encompasses the cosmid array, based on the positive amplification of YAC 428C5. One location of D5F149 was detected on both our cosmid and YAC clones. Our data suggested, as with CATT-1, the existence of null alleles and/or instability of the CMS-1, D5F150, D5F151, D5F149 sequences in YACS.

A deletion event was observed in hybridization with an 800 bp EcoRI fragment isolated as a single copy probe from the CATT-40G1 containing cosmid 234A1 from the chromosome 5 specific cosmid library. Probings of YAC DNA failed to detect this fragment in any of our YACs. Hybridization to genomic DNA of several individuals did not identify any deletion events thus this sequence may be susceptible to instability in the YACS. Sequencing of this fragment did not reveal any exons or coding region.

Figure 5A:
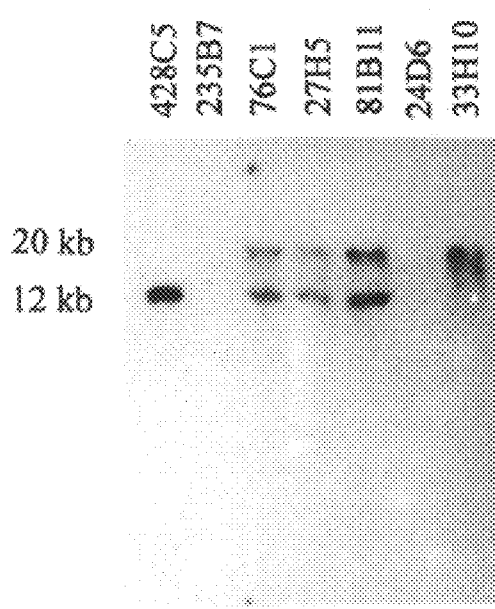
FIG. 5: Sequence duplication in the SMA region identified by p151.2. Hybridization of YACs with (A) the 700 bp fragment and (C) the 500 bp fragment. YACs are arranged from left to right, centromeric to telomeric. Hybridization of cosmids with (B) the 700 bp fragment and (D) the 500 bp fragment. (B) The 12 kb fragment is detected in the cosmids however the 20 kb fragment is not present. The 2.5 kb and 600 bp fragments detected in 3B3 and IEI respectively are end fragments.(D) Only the 3 kb fragment is detected in the cosmids. Note the absence of the 20 kb band in 24D6 in (A) but its presence in (C). The 700 bp fragment may be deleted in 24D6.
Figure 5C:
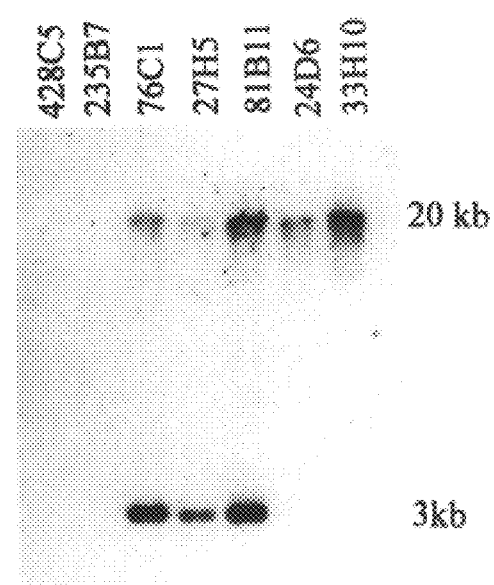

Further evidence of sequence duplication in the SMA region was identified with a 1.2 kb internal Alu-PCR product (p151.2) from cosmid 15F8 (FIG. 4). The probe identified three EcoRI fragments in YAC clones 76C1, 81B11 and 27H5 (20 kb, 12 kb and 3 kb) but only one in 33H10and 24D6 (20 kb) and one in 428C5 (12 kb). An internal EcoRI site divided this marker into 500 bp and 700 bp probes. The larger probe identified the 12 kb and 20 kb fragments while the smaller probe identified the 3 kb and 20 kb fragments (FIG. 5). We ruled out instability of this sequence in YACs as they are from different libraries and the hybridization patterns reflected their physical location. The 12 kb and 3 kb fragments were localized on the EcoRI restriction map, however we were unable to position the 20 kb fragment. Taken together these findings suggest the 12 kb and 3 kb lie in tandem with a centromeric/telomeric orientation respectively. A location of the 20 kb fragment distal to our contiguous array of cosmids may be inferred from the data. The duplication was confirmed by hybridization to genomic DNA digests revealing all three fragment sizes.

YAC Contig and Cosmid Contig Characteristics

We established a YAC contig of the SMA disease gene region, incorporating the D5S435-D5S112 interval and encompassing 4 Mb. Orientation of the contig along 5q13 was confirmed by analysis of seven genetic markers and STSs in combination with PFGE analysis. The long range restriction map revealed neither major deletions nor rearrangements among the YACs within our contig, and was utilized to refine the estimates of the size of the contig. Our YAC map establishes physical linkage of the markers D5S629, D5F153, D5F151, D5F150, D5F149, CMS-1, CATT-1 and D5S557 to a 1.1 Mb region, a region of the genome characterized by low copy repetitive sequences and multilocus STRS. Furthermore, we estimated the new genetically defined CMS1-SMA-D5S557 to be 550 kb. Estimates of the physical distance of the D5S435-D5S557 interval ranging from 400 kb (Francis et al., 1993) to 1.4 Mb (Wirth et al., 1993) have been reported. In contrast to these studies our estimation of 1.4 Mb for the D5S435-SMA-D5S557 interval and 550 kb for the CMS11-SMA-D5S557 interval, employs clones derived from three sources, comprised of 6 chromosomes. Moreover, the determination of both the size of clones and the position of rare cutter sites has enabled us to determine more precisely the extent of overlap of the YACs and the size of the contig providing a reliable estimation.

We also assembled a single contiguous array of cosmid clones derived from both a chromosome 5 specific library and a YAC (76C1) specific library in conjunction with a restriction map of the CMS-1/CATT-1/D5F153/D5F150/ D5F149 region encompassing 210 kb. The repetitive sequences prevented extension of the cosmid contig when utilizing a chromosome 5 specific library necessitating construction of a cosmid library YAC 76C1 in the critical region. The contiguous cosmid array was constructed by a directed walking strategy with validation of cosmid overlap established by restriction fragment enzyme overlap, Alu fingerprinting, and analyses involving STSs, cosmid end clones and single copy probes.

Physical and genetic mapping analyses revealed a complex region of genomic DNA comprising duplications and the presence of repetitive sequences. Genotyping of genomic DNA with complex STRs from this region revealed the presence of a polymorphic number of bands ranging as high as eight per individual. This suggested the presence of multiple copies, or subloci, for the STRs CATT-1, CMS-1, D5F153, D5F150. Our physical mapping data confirmed the presence of these subloci except in the case of D5F151 and D5F149 which revealed only one location. Four of the CATT-1 subloci map to our cosmid array within a 140 kb region; at least one of these subloci, CATT-40G1, is duplicated. D5F153 and CATT-1 are related STRs which appear to have diverged from a common ancestor. We had localized one CMS-1 sublocus to our cosmid array, however, we were unable to determine from our data whether other subloci exist on other chromosomes within this 200 kb interval, as the chromosomes from which the YAC/cosmid libraries were derived may either contain null alleles at the remaining subloci or have sustained deletions.

The CATT-1, D5F153, D5F150 and D5F149 STR, although present in multiple copies on chromosomes in the population were observed as single sublocus markers on all YACS, as evidenced by single allele PCR products for each, suggesting instability and deletion of these sequences. This is supported by the absence in our YACs of an 800 bp fragment, derived from the chromosome 5 cosmid library based contiguous array. Instability of these sequences does not appear to result in large deletions as additional unique sequence probes located between the multiple subloci are retained in the YACs.

In summary, we have produced the first high resolution physical map of the critical SMA region. However, delineation of the precise region which contained the SMA gene was not possible based on this information alone.

Figure 9B:
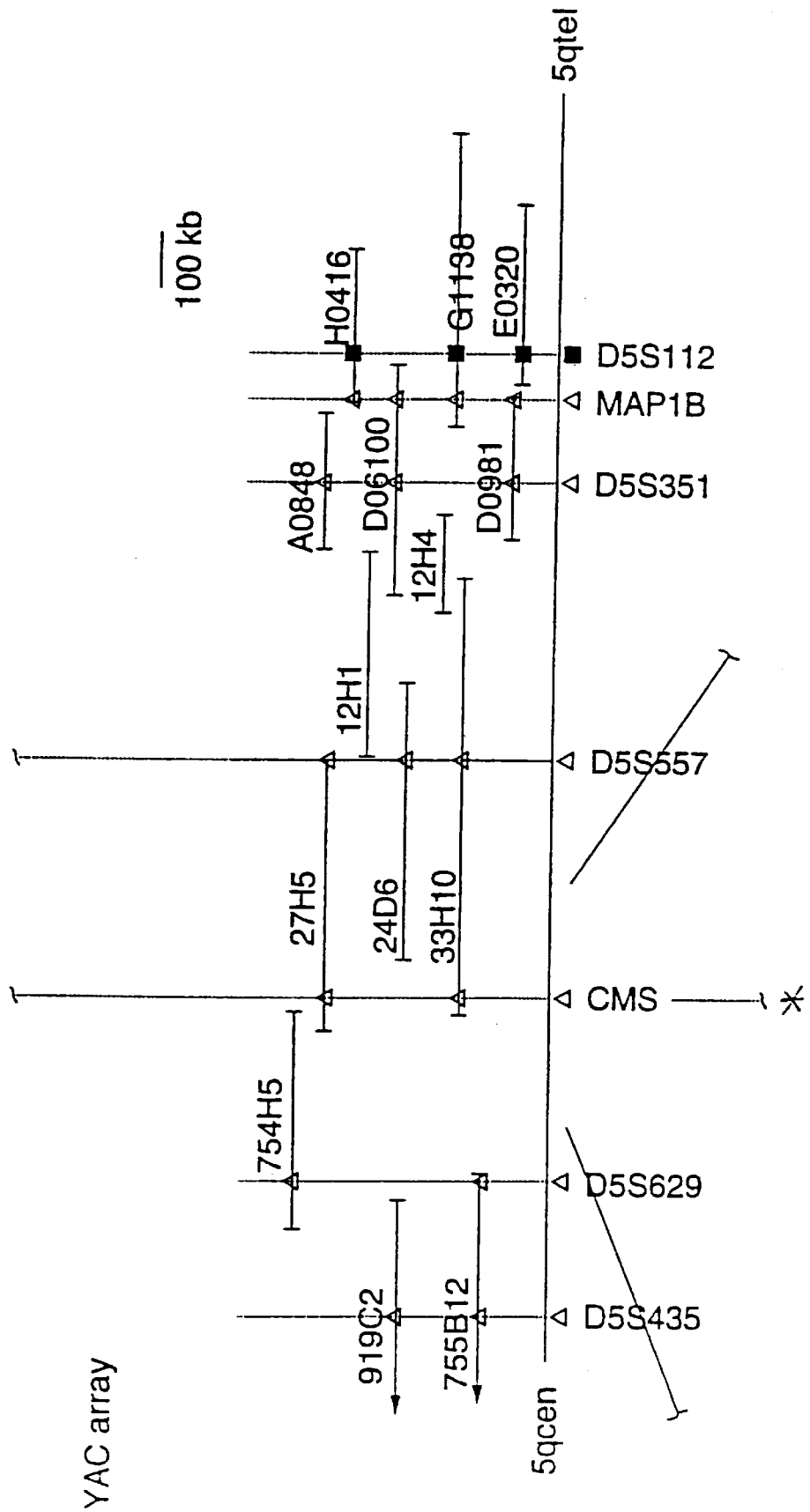

Concurrent with our genetic analysis, we constructed a YAC contiguous array employing clones from three different YAC libraries (Roy et al., 1994). A minimal representation from this array, which was correlated with extensive pulsed field gel electrophoresis (PFGE) analysis, is shown in FIG. 9B.

Figure 9C:
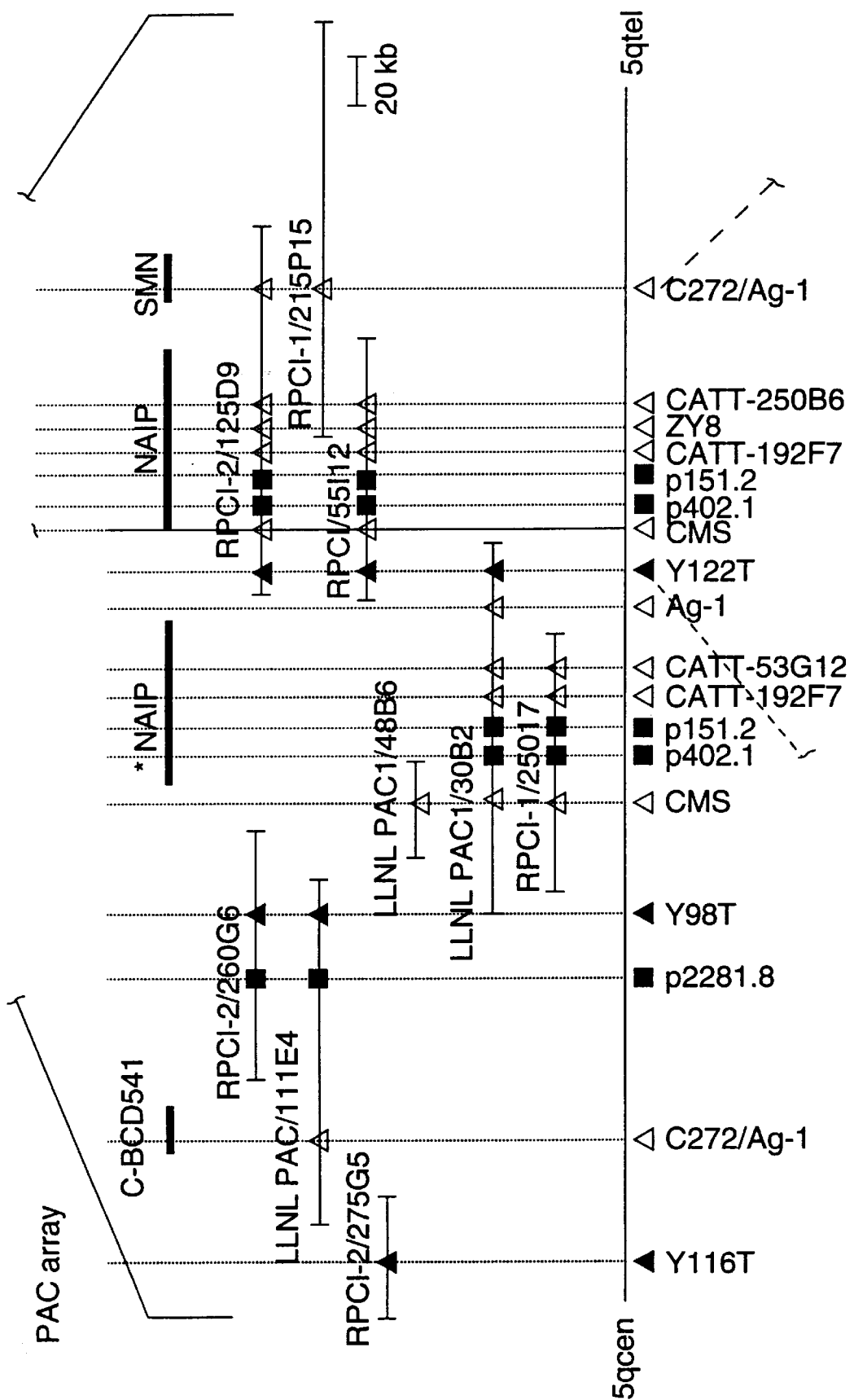
Figure 9D:
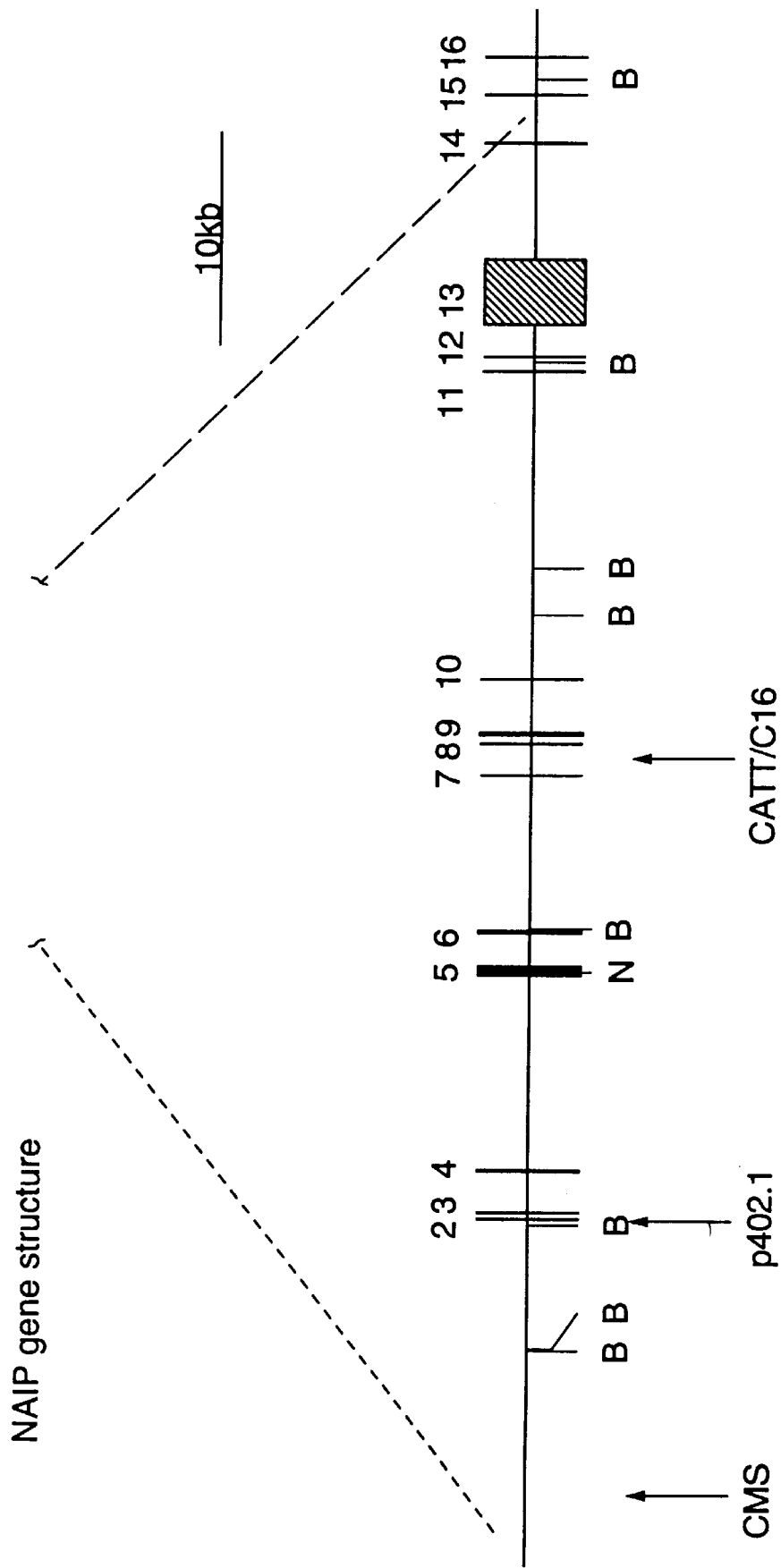

With the initial suggestion of linkage disequilibrium of the general CATT marker and SMA (Burghes et al., 1994), the construction of a cosmid contiguous array incorporating the extended CATT region was undertaken. The presence of extensive and polymorphic genomic repetitive elements mapping both to 5q13 and elsewhere on chromosome 5 interfered with a straightforward assembly of a contiguous array. However, the integrity of the array was established by restriction enzyme analyses, Alu-PCR fingerprinting, STS content determination and nucleic acid hybridization using cosmid end clones and other single copy probes. This resulted in the generation of an array encompassing 220 kb that contained the five CATT subloci contained in a monochromosomally derived flow sorted chromosome 5 genomic library (Roy et al., 1994). More recently, a P1 artificial chromosome (PAC, Ioannou et al., 1994) contiguous array containing the CATT region, comprised of 10 clones and extending approximately 550 kb, was constructed (FIG. 9C).

Linkage Disequilibrium Analysis

Figure 6:
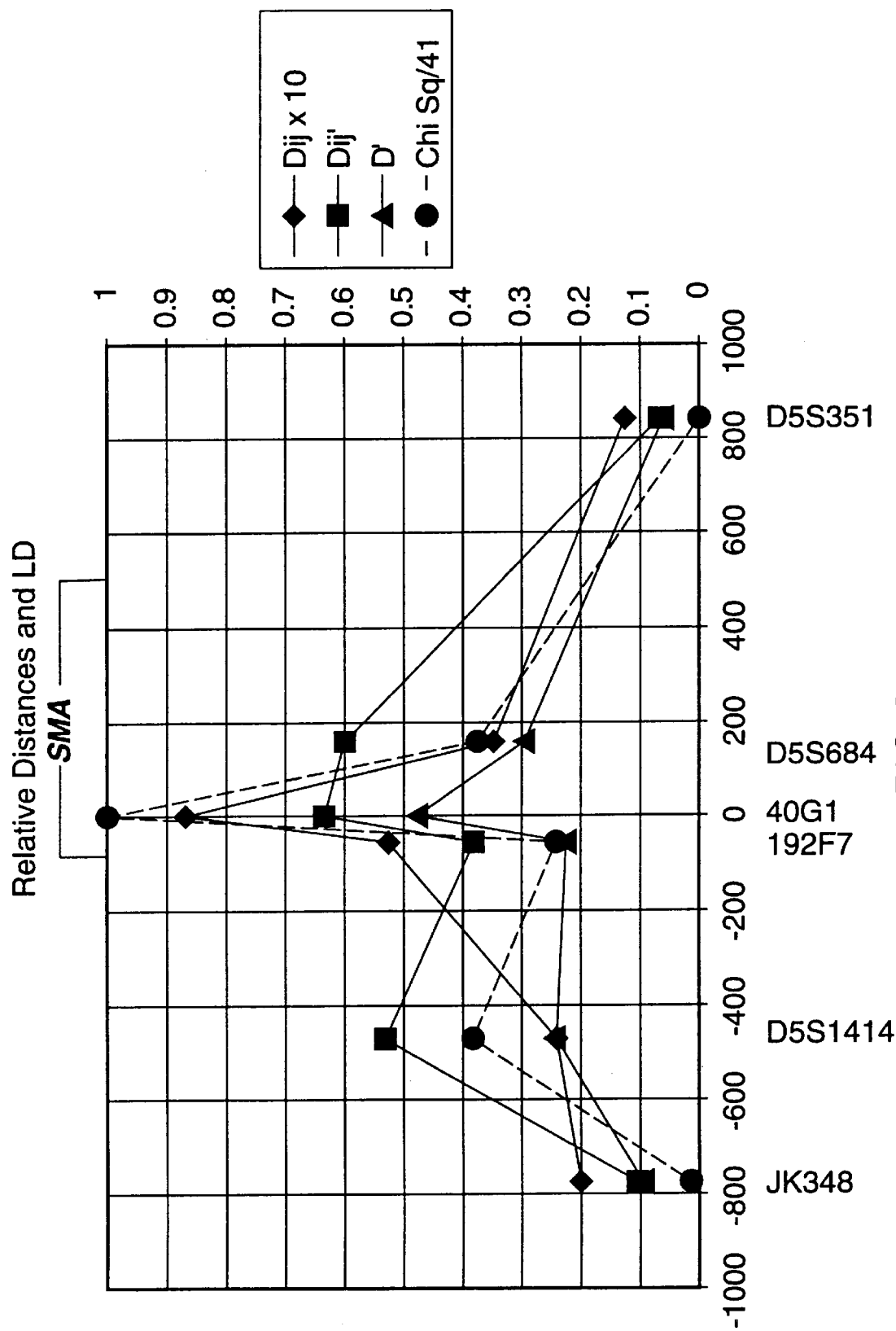
FIG. 6: Degree of linkage disequilibrium observed between Type I SMA and various polymorphic 5q13.1 markers giving a disequilibrium peak at 40G1.

A linkage disequilibrium analysis employing 5 complex and simple tandem repeats mapping to the SMA region was conducted. Two of the polymorphisms employed in this analysis were the CATT-40G1 and CATT-192F7 subloci which we mapped to our cosmid array. Specific amplification of the two individual subloci was achieved by constructing primers ending on sequence polymorphisms in the region flanking the CA repeat. A clear linkage disequilibrium peak was observed at the CATT-40G1 sublocus as shown in FIG. 6.

PAC Contig Array

Figure 7:
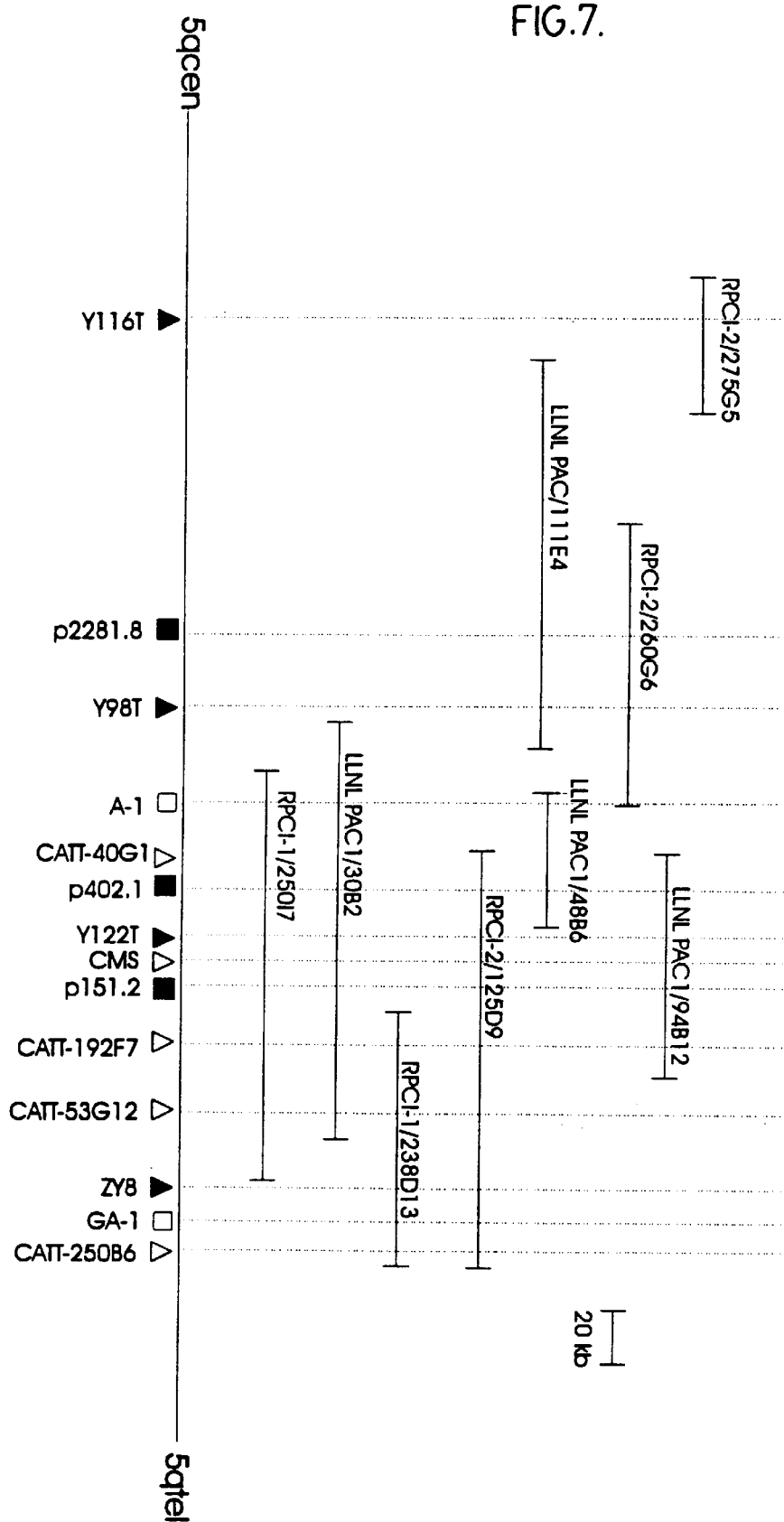
FIG. 7: A PAC contiguous array containing the CATT region comprised of nine clones and extending approximately 400 kb. The 2.2 kb transcript referred to as GA1 is shown.

Since the 40G1 CATT subloci demonstrated linkage disequilibrium, a PAC contiguous array containing the CATT region was constructed. This PAC contig array comprised 9 clones and extended approximately 400 kb (FIG. 7). Our genetic analysis combined with the physical mapping data indicated that the 40G1 CATT subloci marker which showed the greatest disequilibrium with SMA was duplicated and was localized at the extreme centromeric of the critical SMA interval. Consequently the 154 kb PAC clone 125D9 which contained within 10 kb of its centromeric end the SMA interval defining CMS allele 9 and extended telomerically to incorporate the 40G1 CATT sublocus was chosen for further examination.

Two genomic libraries were constructed by performing complete and partial (average insert size 5 kb) Sau3A1 on PAC 125D9 and cloning the restricted products into BamH1 digested Bluescript plasmids. Genomic sequencing was conducted on both termini of 200 clones from the 5 kb insert partial Sau3A1 library in the manner of (Chen et al., 1993) permitting the construction of contiguous and overlapping genomic clones covering most of the PAC. This proved instrumental in the elucidation of the neuronal apoptosis inhibitor protein gene structure.

PAC 125D9 is cleaved into 30 kb centromeric and 125 kb telomeric fragments by a NotI site (which was later shown to bisect exon 7 of the PAC 125D9 at the beginning of the apoptosis inhibitor domain. The NotI PAC fragments were isolated by preparative PFGE and used separately to probe fetal brain cDNA libraries. Physical mapping and sequencing of the NotI site region was also undertaken to assay for the presence of a CpG island, an approach which rapidly detected coding sequences. The PAC 125D9 was also used as a template in an exon trapping system resulting in the identification of the exons contained in the neuronal apoptosis inhibitor protein gene.

The multipronged approach, in addition to the presence of transcripts identified previously by hybridization by clones from the cosmid array (such as, GA1 and L7), resulted in the rapid identification of six cDNA clones contained in neuronal apoptosis inhibitor protein gene. The clones were arranged, where possible, into overlapping arrays. Chimerism was excluded on a number of occasions by detection of co-linearity of the cDNA clone termini with sequences from clones derived from the PAC 125D9 partial Sau3A1 genomic library.

Cloning of Neuronal Apoptosis Inhibitor Protein Gene

In the meantime, a human fetal spinal cord cDNA library was probed with the entire genomic DNA insert of cosmid 250B6 containing one of the 5 CATT subloci. This resulted in a detection of a 2.2 kb transcript referred to as GA1 which location is shown in FIG. 7. Further probings of fetal brain libraries with the contiguous cosmid inserts (cosmids 40G1) as well as single copy subclones isolated from such cosmids were undertaken. A number of transcripts were obtained including one termed L7. No coding region was detected for L7 probably due to the fact that a substantial portion of the clone contained unprocessed heteronuclear RNA. However, we later discovered that L7 proved to comprise part of what is believed to be the neuronal apoptosis inhibitor protein gene. Similarly, the GA1 transcript ultimately proved to be exon 13 of the neuronal apoptosis inhibitor protein. Since GA1 was found to contain exons indicating that it was an expressed gene, it was of particular interest. The GA1 transcript which was contained within the PAC clone 125D9 was subsequently extended by further probing in cDNA libraries.

The extended GA1 transcript was compared to other known sequences to reveal that its amino acid sequence had significant homology to the inhibitor apoptosis polypeptides of *Orgyia Pseudotsugata* and *Cydia Pomonella* viruses (Table 3). This sequence analysis revealed the presence of inhibitor apoptosis protein homology in exons 5 and 6.

The remaining gaps in the cDNA were completed and the final 3' extension was achieved by probing a fetal brain library with two trapped exons. A physical map of the cDNA with overlapping clones was prepared. The entire cDNA sequence (SEQ ID NO: 1) is shown in Table 4 and contains sixteen exons. The amino acid sequence (SEQ ID NO: 2) starts with methionine which corresponds to the nucleotide triplet ATG. FIG. 8 demonstrates the structural organization of the SMA gene.

The cDNA sequence of NAIP (SEQ ID NO: 1) shown in Table 4 allows one skilled in the art to develop from this gene, primers, probes and also antibodies against the protein product. The cDNA sequence (SEQ ID NO: 1) of Table 4 may be used in recombinant DNA technology to express the sequence in an appropriate host in order to produce the neuronal apoptosis inhibitor protein. In this manner, a source of neuronal apoptosis inhibitor protein is provided. Given the sequence of NAIP and the probes and primers therein, deletions in the sequence may also be detected, for instance, in the disorder Spinal Muscular Atrophy.

NAIP Structure

The NAIP gene contains 17 exons comprising at least 5.5 kb and spans an estimated 80 kb of genomic DNA. The NAIP coding region spans 3698 nucleotides resulting in a predicted gene product of 1233 amino acids (SEQ ID NO: 2). NAIP contains two potential transmembrane regions and an intracellular inhibitor of apoptosis domain immediately contiguous with a GTP binding site. Searches of the protein domain programs generated the following results:

(i) residues 9–91: an N terminal domain with no recognizable motifs.

(ii) residues 94–118: hydrophobic potential membrane spanning domain.

(iii) residues 169–485: a domain which shows homology with apoptosis inhibitors and is immediately before the next hydrophobic domain, GTP/ATP binding site.

(iv) residues 486–504: a hydrophobic potential membrane spanning domain.

(v) residues 505–1005: possible receptor domain containing 4 N-linked glycosylation sites and a lipoprotein binding domain Neuronal Apoptosis Inhibitor Protein Gene Mutational Analysis A cDNA20.3 probe was found by using the entire PAC 125D9 as a probe to screen cDNA libraries. Probing of genomic southerns with cDNA probe 20.3 revealed the absence of a 9 kb EcoRI band in a Type III consanguineous family. This information mapped the NAIP gene deletions to exons 5 and 6. Thus the deletion covers the exon containing the rare NotI restriction site and the exon immediately downstream. Primers in and around these exons were constructed revealing the absence of amplification from 3 Type I and 3 Type III SMA individuals. Genomic DNA was isolated from PAC and cosmid subclones in and around exons 4 and 5 and sequenced in an effort to generate primers which would amplify the junction fragment generated by the causative deletions as depicted. A junction fragment was detected in the Type III individual. A similar product was observed in two other French Canadians with no history of consanguinity. The 3 Type I and 3 Type III SMA individual's chromosomes had identical CATT/CMS haplotypes strongly suggesting that this is a common mild SMA mutation and comparatively frequent in the French Canadian population. Cosegregation of this pattern was demonstrated. We have conducted analysis of 110 parents of SMA individuals and have failed to find a similar product. Sequencing of the genomic DNA in this region revealed an approximately 10 kb deletion resulting in an in frame deletion. This deletion spans intron regions and exons 5 and 6. Southern blot analysis of two generation SMA families was performed. A cDNA probe encompassing the first eight exons was performed on EcoRI-digested DNA from peripheral blood leukocytes. SMA affected members show an absence of hybridization to a 10 kb EcoRI band which was shown to contain exons 5 and 6 (FIG. 9).

Initial isolation of the NAIP transcript was achieved by probing a human fetal brain cDNA library with the entire 28 kb genomic DNA insert of cosmid 250B6 that contains one of five CATT subloci present in the cosmid library. This resulted in the detection of a 2.2 kb transcript that ultimately proved to be exon 14 of the NAIP gene. Further probing of fetal brain libraries with the contiguous cosmid inserts (cosmid 40G1), as well as single copy subclones isolated from such cosmids identified a number of transcripts including the L7 transcript that ultimately proved to contain exon 13 of the NAIP locus. No coding region was detected for L7, probably due to the fact that a substantial proportion of the clone contained unprocessed heteronuclear RNA, obscuring its true nature.

At this stage, the completed genetic and linkage disequilibrium analyses and construction of the PAC contiguous array identified PAC 125D9 as having a good probability of containing the SMA locus. Four PAC 125D9 genomic libraries were constructed by performing complete and partial (average insert size 5 kb) Sau3AI, BamHI and BamHI/NotI digests on the PAC insert and cloning the restricted products into plasmid vector. High through put genomic sequencing was conducted on both termini of 200 clones from the 5 kb insert partial Sau3AI digestion library in the manner of (Chen et al., 1993), permitting the construction of contiguous and overlapping genomic clones covering most of PAC 125D9 (data not shown). This has proven instrumental in elucidating the gene structure of the NAIP locus.

Figure 11B:
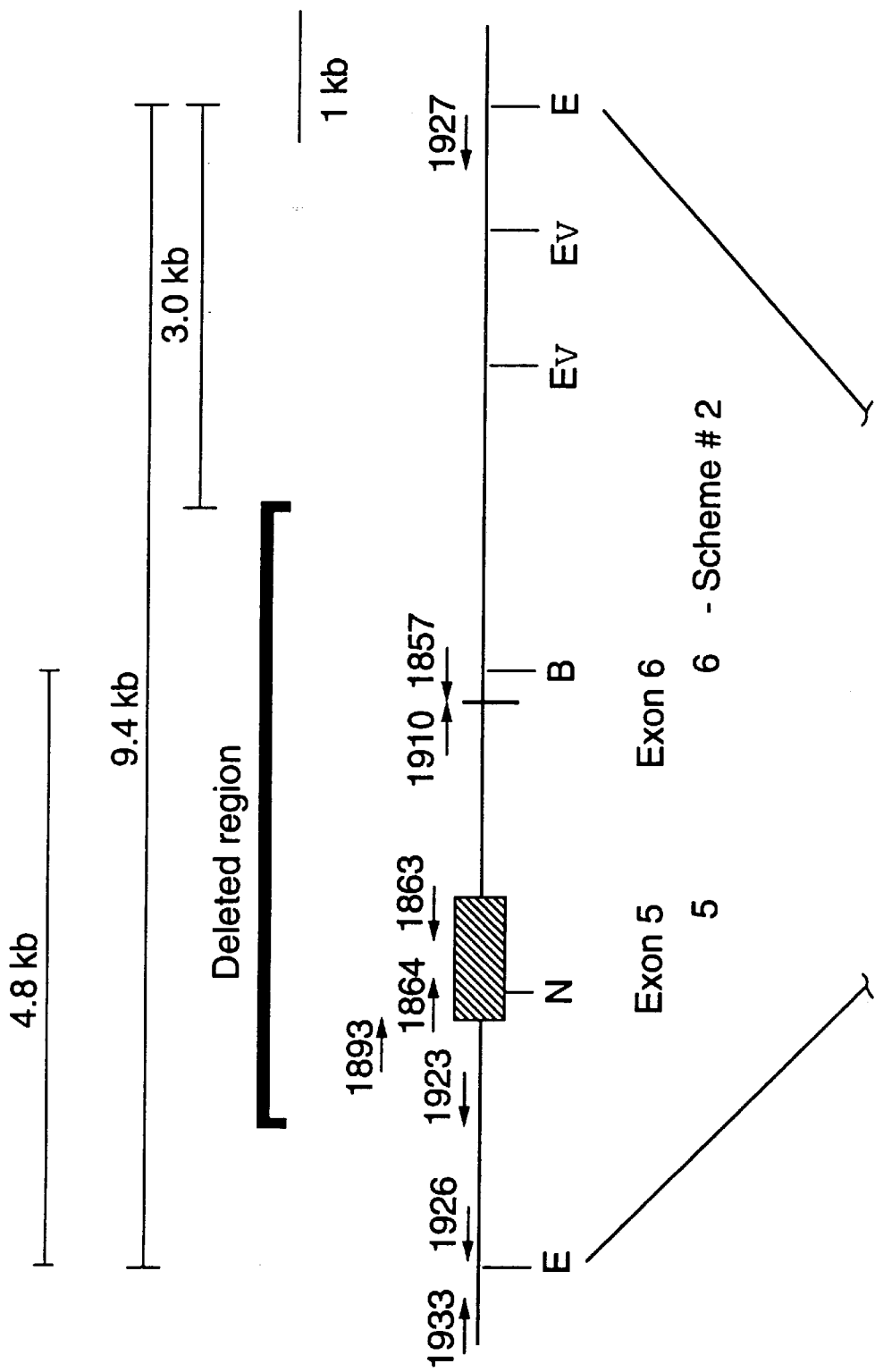
Figure 13:
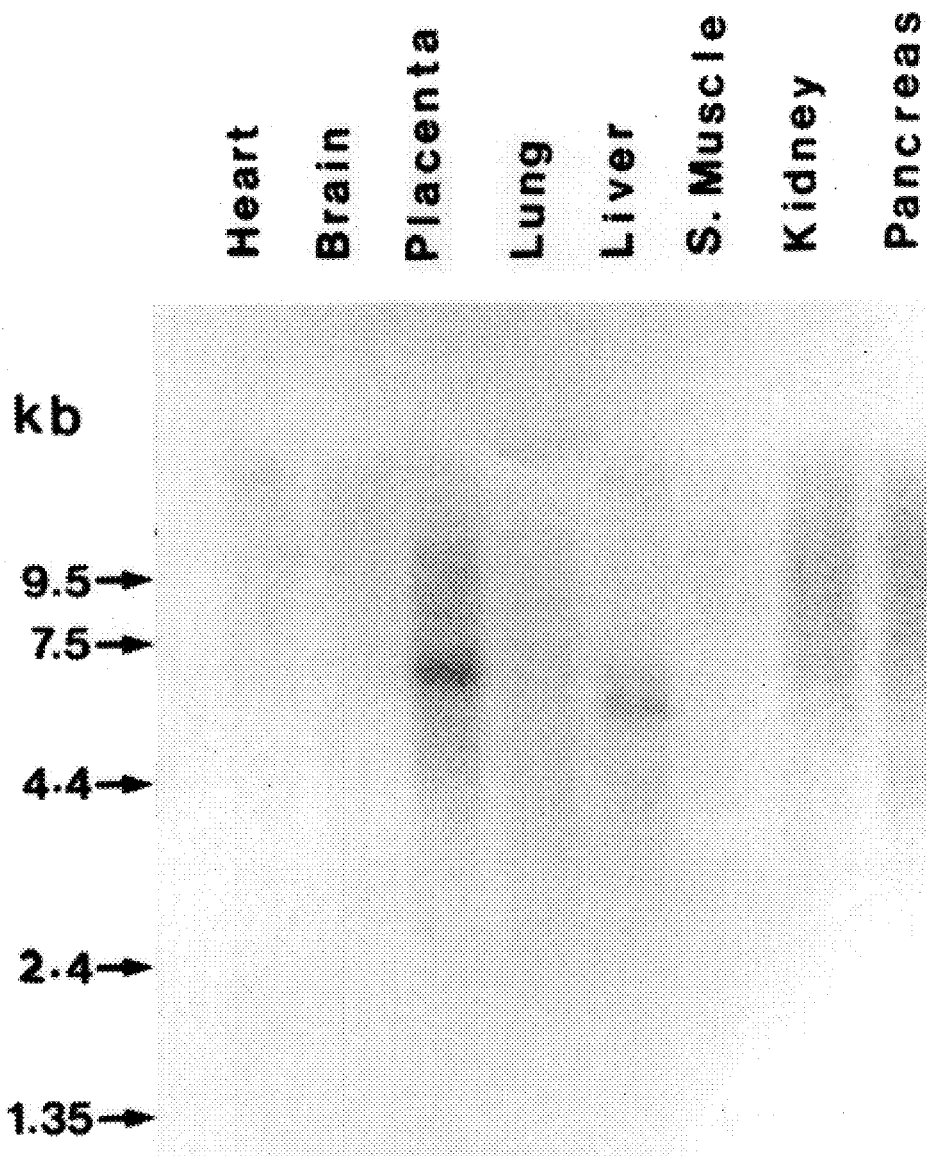
FIG. 13: Northern blot of adult tissues probed with exon 13 (Scheme #2) of the NAIP locus. Tissues are as marked and the filter were washed at 50° C., 0.2× SSC and exposed for 4 days. Bands can seen in liver and placenta in the 6–7 kb range.

PAC 125D9 is divided into 24 kb centromeric and 130 kb telomeric fragments by NotI digestion, bisecting exon 6 of the NAIP gene at the beginning of the first potential transmembrane domain mapping upstream of the inhibitor of apoptosis homologous domains (FIG. 11 and Table 4). The NotI PAC fragments were isolated by preparative PFGE and used separately to probe human fetal brain cDNA libraries. Physical mapping and sequencing of the NotI site region was also undertaken to assay for the presence of a CpG island, an approach that rapidly detected coding sequence. The PAC was also used as a template in an exon trapping system (Church et al., 1994) resulting in the identification of the NAIP gene exons 5, 12, 16 and 17.

Figure 10:
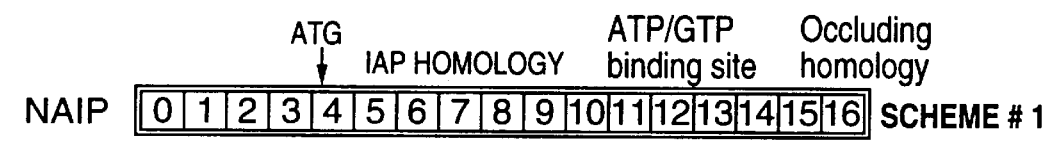
FIG. 10: Exon content of PAC, fetal brain cDNA clones from non-SMA individuals and RT-PCR clones from SMA affected individuals. E158 refers to the deletion of a glutamate residue. The RT-PCR products was only performed between exons 13 and 4 (Scheme #2); additional, undetected deletions may exist outside of this region.

This multi-pronged approach resulted in the identification of cDNA clones spanning the NAIP gene (FIG. 10). Overlapping clones were identified and chimerism of cDNA clones was excluded on a number of occasions by the detection of co-linearity of the cDNA clone termini with sequence from clones of the PAC 125D9 partial Sau3AI digestion genomic library. At this time, sequence analysis revealed the similarity between the protein sequence encoded by the NAIP gene exons 7 through 13 with two baculoviral inhibitor of apoptosis proteins (IAPs). Shortly thereafter, probing of Southern blots containing DNA from consanguineous SMA families with cDNA probes revealed deleted bands.

Both IAPs contain in their amino terminus an 80 amino acid BIR (baculovirus IAP repeat) motif that, after an intervening sequence of approximately 30 residues, is duplicated with 33% identity (Clem and Miller, 1993). The same phenomenon is observed in NAIP; amino acids 185–250 encoded by exons 6, 7 and 8 are 35% homologous to amino acids 300–370 encoded in exon 10, 11 and 12. The greatest stretch of homology is observed over a 53 amino acid region with 29 identical amino acids.

In addition to the NH2 terminal IAP domain, there exists cysteine and histidine rich zinc finger-like motifs in the carboxy terminus of both CpIAP and OpIAP. These motifs, which are proposed to interact with DNA (Birnbaum et al., 1994), are not seen in NAIP (Table 4). NAIP contains two potential transmembrane regions that bracket an inhibitor of apoptosis domain and a contiguous GTP binding site. Additional searches of protein domain programs generated the following more specific results than the aforementioned protein domain evaluation.

1. Residues 1–91: an N terminal domain with no recognizable motifs;
2. Residues 92–110: a hydrophobic domain predicted by the MEMSAT program (Jones et al., 1994) to be a membrane spanning domain;
3. Residues 163–477: a domain that shows homology with baculoviral inhibitors of apoptosis proteins followed by, and immediately upstream of the next hydrophobic domain, a GTP/ATP binding site;
4. Residues 479–496: hydrophobic domain predicted by MEMSAT to be a membrane spanning domain;
5. Residues 497–1232: a possible receptor domain containing four N-linked glycosylation sites and a procaryotic lipid attachment site.

We know of at least three exons that comprise 400 bp of 5' untranslated region (5'UTR); it is possible that more exist. A striking feature of this region is the presence of a perfect duplication of a 90 bp region in the 5' UTR before exon 2 and in the region bridging exons 2 and 3 (Table 4). In addition, the 3' untranslated region comprising exon 17 has been found to contain a 550 bp interval that has potential coding region detected by the GRAIL program with high homology (P=1.1e-37) to the chicken integral membrane protein, occluding (Furuse et al., 1993). There exists, the possibility that this represents a chimeric transcript. Occluding homologous sequence has been detected in four different cDNA clones and two isoforms of the gene. The possibility of the occluding sequence representing a coding exon of the NAIP gene with the putative 3' UTR actually being heteronuclear RNA is also unlikely given the consistency with which the 3' UTR is observed and the presence of in frame translational stop codons mapping upstream of the region of occluding homology. Preliminary RT-PCR analysis indicates that the occluding tract is transcribed.

Tissue Expression

Hybridization of a Northern blot containing adult tissue mRNA with an exon 14 probe detected bands only in adult liver (approximately 6 and 7 kb bands) and placenta (7 kb, FIG. 6). Although the level of expression in adult CNS is not sufficient to result in visible bands on Northern analysis, successful reverse transcriptase-PCR (RT-PCR) amplification of the NAIP transcript using spinal cord, fibroblast and lymphoblast RNA suggests transcriptional activity in these tissues.

Detection of Truncated and Internally Deleted Versions of the NAIP gene

In the analysis of the PAC contig, the clones 238D12 and 30B2 were noted to show significant sequence similarity with 125D9 but not to contain the NotI site in PAC 125D9 that is located in NAIP exon 6. This indicated the possibility of duplicated copies of the NAIP gene and so further analysis by hybridization of Southern blots containing PAC DNA with NAIP exon probes and PCR STS content assessment was undertaken. In this manner, two aberrant versions of the NAIP locus were detected, one with exons 2 to 7 deleted (PAC 238D12), and another with exons 6, 7 and 12 to 15 deleted (PACs 30B2 and 250I7). The presence of identical sized bands in both genomic and PAC DNA on Southern blot analysis as well as PCR results outlined below obviate the possibility that the deletions represent in vitro PAC artifacts rather than the in vivo situation. Thus, genomic DNA Southern blots hybridized with NAIP exon probes revealed more bands than would be expected with a single intact copy of the NAIP gene. For example, probing of blots containing BamHI restricted genomic DNA with NAIP exons 3–11 should lead to a single band comprised of equal sized contiguous 14.5 kb BamHI fragments in the intact NAIP locus (FIG. 11). Instead, two additional bands are seen at 9.4 and 23 kb (FIG. 14), fragments that are seen in PACs 238D12 and 30B2/250I7 respectively. The 9.4 fragment BamHI has been subcloned from a cosmid and found to contain exons 8–11 with a deletion incorporating exons 2 to 7 occurring just upstream of the 8th exon (FIG. 11). The 23 kb band is generated by a 6 kb deletion removing a BamHI site leading to the replacement of the two contiguous 14.5 kb BamHI fragments with a 23 BamHI fragment containing exons 2 to 5 and 8 to 11 and lacking exons 5 and 6 as depicted in FIG. 11. The left side of this deletion was mapped by the fact that amplification with primers 1933 and 1926 generated a product whereas PCR with 1933 and 1923 did not (data not shown). PCR employing primers 1927 and 1933, constructed to amplify a 4.2 kb junction fragment spanning the 6 kb deletion (FIG. 11), generated the appropriate product as shown by size and sequencing in both genomic DNA and PACs 30B2/250I7. The variable dosage of both the 9.4 and 23 kb bands seen in genomic DNA from different individuals indicates that the two partially deleted versions of the NAIP gene are present in multiple and polymorphic number in the general population.

A further level of complexity was detected with the identification of clones from a non-SMA human fetal brain cDNA library deleted for exons 11 and 12 (Scheme #1), some of which also had exons 15 and 16 (Scheme #1) absent (FIG. 10). The fact that these deletions result in frame shifts and premature protein truncation indicates that they are, rather than normal splicing variants, more likely the result of transcription of the deleted and truncated version of NAIP gene that are present in the general population (FIG. 11). In all, a profile of a region containing a variable number of copies of internally deleted and truncated versions of the NAIP locus, some of which are transcribed, has emerged from our analysis.

Probings of blots containing DNA from the somatic cell hybrid HHW 1064 (Gilliam et al., 1989) with NAIP exonic probes indicates that all forms of the NAIP gene are confined to the 30 Mb deleted region of 5q11-13.3 contained in the derivative chromosome 5 of this cell line. This finding has been confirmed by FISH probings with NAIP exon 13 probe (unpublished data).

NMAP Gene Mutational Analysis

Figure 14:
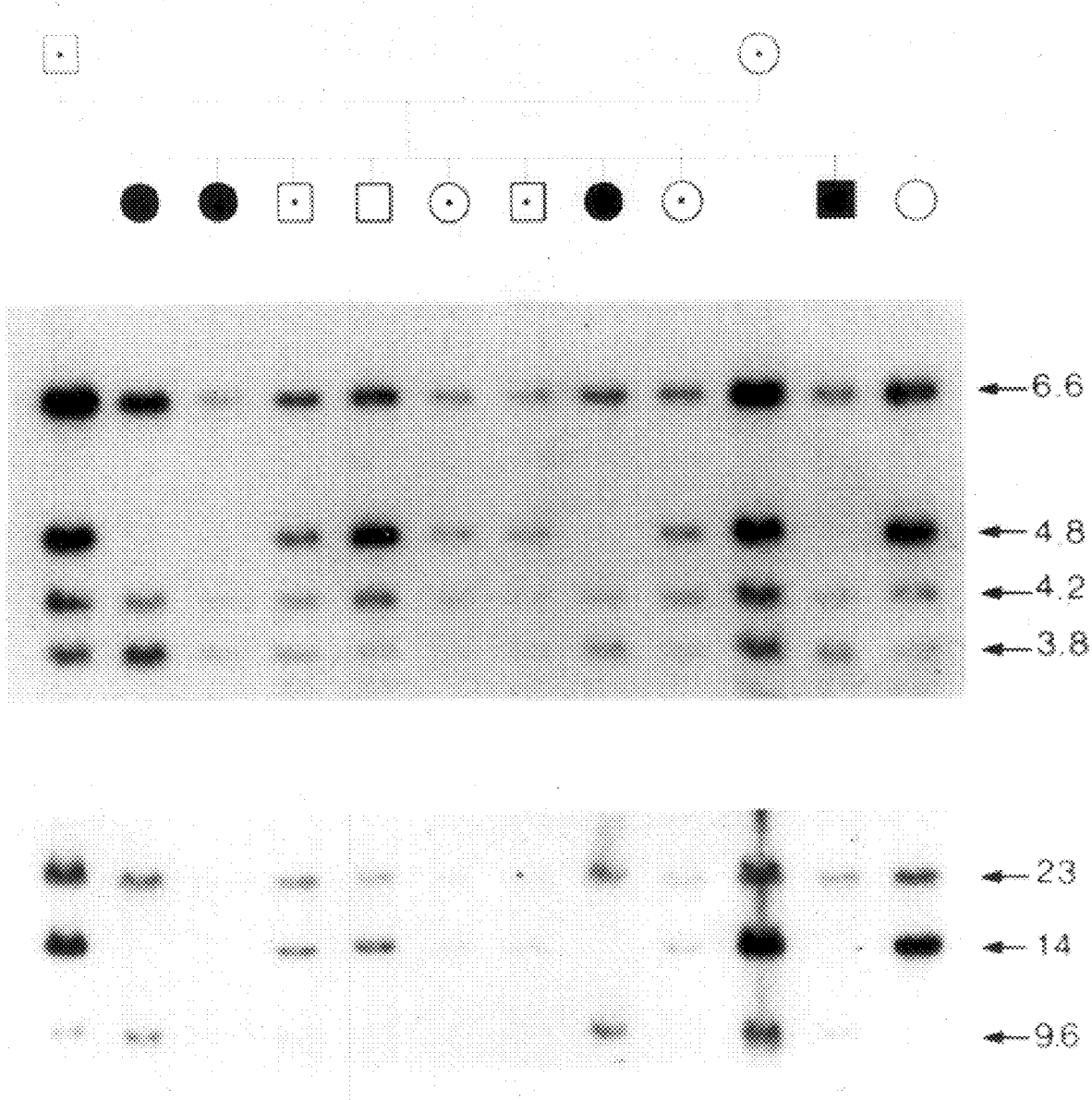
FIG. 14: Pedigree and Southern blot analysis of consanguineous French-Canadian type III SMA families. Upper panel: probing of a filter containing BamHI/EcoRI digested genomic DNA with a cDNA probe encompassing exons 2 through 9 (Scheme #2) of NAIP reveals the loss of the 4.8 kb fragment that contains exons 5 and 6 (Scheme #2) in all affected individuals resulting in an in-frame deletion. All others, save for the homozygous normal sister and brother show half dosage for this band. The lower panel shows a BamHI digest of the same family. In affected individuals two superimposed 14.5 kb contiguous fragments have sustained the 6 kb deletion of sequence containing a BamHI site resulting in the generation of a 23 kb band (see FIG. 11). Note the existence of the 23 kb BamHI band in all individuals in the pedigree in keeping with its general dispersion in the population. Similarly, the 9.6 kb BamHI band representing the deletion of exons 1 through 6 (Scheme #2) which is contained in PAC 238D12 and depicted in FIG. 11 can be seen in all individuals including non-SMA carriers.

Probing of genomic Southern blots with PCR amplified NAIP exons 3 to 10 revealed the absence of a 4.8 kb EcoR1/BamHI fragment containing exons 5 and 6 in the four affected individuals of consanguineous Type III SMA family 24561 (FIGS. 11 and 14). The same probing of BamHI digested DNA from this family revealed the absence of a 14.5 kb band also in keeping with a loss of exons 5 and 6 as outlined above (FIGS. 11 and 14). Similar results were observed in two other French Canadian SMA families that were also believed consanguineous.

In order to confirm the proposed deletion of exons 5 and 6, primers homologous to these exons were made (primers 1893, 1864, 1863, 1910 and 1887 identified by arrow in FIG. 11. Results of a representative PCR amplification of DNA from the family 24561 and a second Type III SMA consanguineous family using exon 5 specific primers (primer 1864 and 1863) along with a simultaneous reaction of an exon 13 sequence included to rule out a failure of the PCR are shown in FIG. 15. Absence of amplification of exon 5 can be seen to cosegregate with the SMA phenotype.

In order to determine if the exon 5 and 6 NAIP gene deletion was an SMA mutation, Southern blot analysis was conducted. An 800 bp EcoRV single copy probe that mapped immediately to the 3' side of the 6 kb exon 5 and 6 deletion was employed (FIG. 11). Hybridization of this marker to. EcoRI Southern blots detected both a 9.4 kb EcoRI fragment containing exons 5 and 6 from the intact NAIP locus as well as a 3 kb EcoRI band from the exon 5 and 6 deleted copy of the NAIP gene. Analysis was conducted on EcoRI Southern blots containing DNA from over 900 unrelated members of myotonic dystrophy, ADPKD and cystic fibrosis families obtained from our DNA diagnostic laboratory. The 9.4 kb band was seen in all individuals in keeping with the presence of at least one copy of exons 5 and 6 in each of the approximately 900 individuals tested. In addition, the 3 kb band was observed in every individual reflecting a virtually complete dispersion of some form of the exon 5 through 6 deleted NAIP gene in the general population. Moreover, the variable band dosage observed for the 3 kb band suggested that the number of copies of the exon 5-6 deleted NAIP gene is polymorphic possibly ranging as high as 4 or 5 copies per genome.

PCR analysis was then extended to 110 SMA families, employing exon 5 and 6 primers. Seventeen of 38 (45%) Type I SMA individuals and 13 of 72 (18%) Type II and III SMA individuals were homozygously deleted for these exons. Assuming random assortment of chromosomes and therefore taking the square of the observed frequency of homozygous exon 5 through 6 deleted individuals yields estimated frequencies for exon 5 through 6 deleted chromosomes of 67% in Type I SMA and 42% in Type II/III SMA. PCR analysis was next conducted on 168 parents of SMA children revealed failure of amplification suggesting homozygous deletion of exon 5 and 6 in three individuals. This finding was confirmed by Southern analysis in the two cases with sufficient DNA for this assay. The two individuals, aged 28 and 35 and both parents of Type I SMA children, when interviewed by telephone described themselves to be physically well, reporting no symptoms suggestive of SMA. It was thus concluded that the deletion of NAIPs exons 5 through 6 in isolation, while possibly reflecting more severe deletions in individuals with SMA as outlined below, can be clinically innocuous associated either with an exceedingly mild SMA or even normal phenotype. Clinical assessment of these individuals is currently being undertaken.

Judging both by the cDNA clones detected from fetal brain libraries as well as the make-up of RT-PCR NAIP products (FIG. 2), many and possibly all truncated copies of the NAIP gene appear to be transcribed. Given the apparently unaffected status of the three parents of individuals with SMA who do not have a copy of exons 4 and 5 in their genome we believe that the exon 5 through 6 deleted version of NAIP is also translated. In keeping with this model, removal of exons 5 and 6 results in an in-frame deletion that extends the longest NAIP open reading frame upstream to a start methionine in exon 3 at nucleotide 211 (Table 4).

Furthermore, the protein sequence encoded by the deleted exon 5 and 6 IAP motif is approximately 35% homologous to the IAP motif encoded in exons 10 and 11 possibly accounting for the absence of discernible phenotype in the three exon 5 through 6 deleted individuals. One possible model is that a single copy of exon 5 through 6 deleted NAIP on each chromosome results in the mild SMA phenotype, while individuals with greater than 3 or 4 copies of the exon 4–5 deleted NAIP locus are clinically unaffected. The possibility that duplication of the SMA gene underlies the disease has recently been proposed by DiDonato et al. (1994).

RT-PCR amplification of RNA from SMA and non-SMA tissue. The results of RT-PCR amplification using RNA from both non-SMA and SMA individuals as template are shown in FIG. 16.

We have established that at least some of the internally deleted and truncated NAIP versions are transcribed. In order to distinguish between transcripts from the intact NAIP gene which would produce a functional protein from those that would not, an effort was made to RT-PCR amplify transcripts that were as large as possible. Given the 2.2 kb size of exon 14, this was found to be one which encompassed exon 2 and the 5' end of exon 13. No product was detected at the level of ethidium bromide staining after first round PCR. Therefore, second round nested amplification was undertaken as described in respect of the previous description of FIG. 16.

Figure 16A:
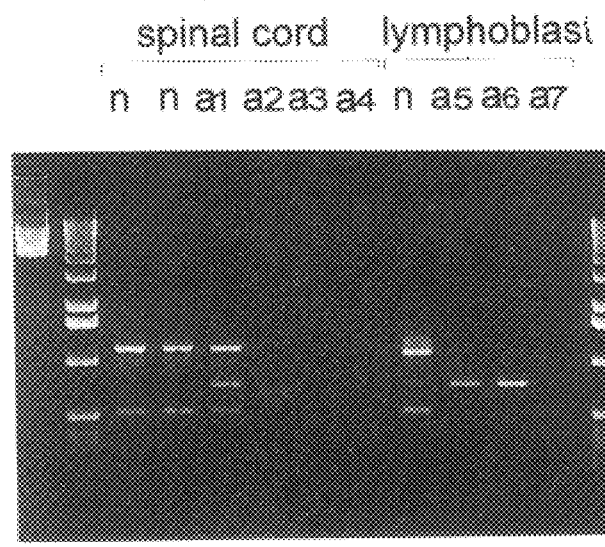
FIG. 16: RT-PCR amplification of RNA from SMA and non-SMA tissues. The letter n refers to RNA from non-SMA tissue and a to RNA from SMA affected tissue. The tissue source is shown above each panel. Lym refers to lymphoblast and fib to fibroblast. All samples were from type 1 SMA patients with the exception of a5 which is from an affected member of the consanguineous type 3 SMA family 24561 shown in FIG. 15.

A representative subset of RT-PCR experiments are shown in FIG. 16. PCR of reverse transcribed product using RNA from non-SMA tissues as template and reverse transcribing from exons 10 or 13 consistently amplified product of the expected size. In contrast, similar RT-PCR experiments on RNA from SMA tissue revealed no amplification in five cases in keeping with the marked down regulation or complete absence of the intact transcript in such individuals (FIG. 16A). The RNA obtained from the SMA tissues was no more than 12 hours post-mortem. As we have no difficulty in amplifying intact NAIP transcript from normal tissue which is 24 hr post mortem, we do not believe the difficulty in amplification arises from RNA degradation. Furthermore, difficulty with amplification was seen for all SMA tissues which suggests against the possibility that NAIP is transcribed solely in the motor neuron with depletion of this cell type in SMA resulting in RT-PCR failure in spinal cord tissue.

Figure 16B:
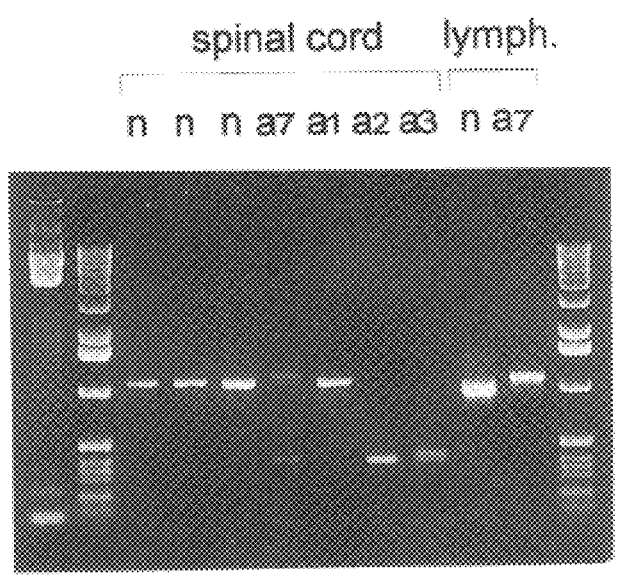
Figure 16C:
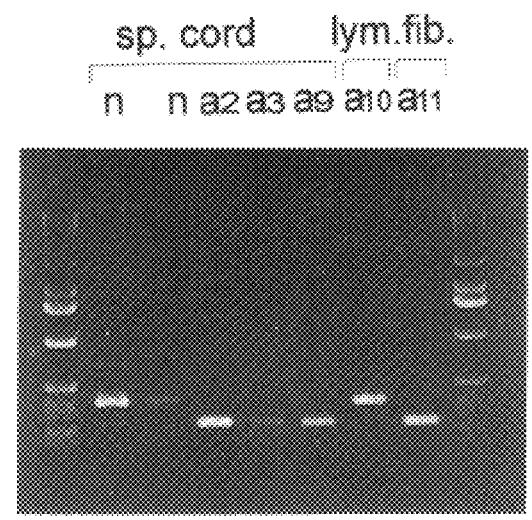

In the cases where amplification was observed, sequencing of RT-PCR products has revealed the following findings, as shown in FIGS. 16A, 16B and 16C:

(i) an in-frame deletion of codons 153 and 190 from the 3' end of exon 5 from sample a9.

(ii) deletion of exon 6 resulting in a frame shift with a stop codon occurring 73 nucleotides into exon 7 in a product amplified by exon 5 primer 1864 and exon 13 primer 1974 from sample a2.

(iii) an approximate 50 nucleotide insertion in a product amplified by exon 4 primer 1886 and exon 13 primer 1974 from sample a7.

(iv) deletion of a glutamic acid codon number 158 in exon 5 in association with deletion of exon 11 and 12 in a product amplified by exon 5 primer 1864 and exon 13 primer 1974 from sample a3.

(v) deletion of exons 11 and 12 introducing a frame shift and a stop codon 14 nucleotides into exon 13 in a product amplified by exon primer 9 primer 1844 and exon 13 primer 1974 in sample a2, a3, a9 and all.

In all, employing PCR on material reverse transcribed from exon 13, we have observed successful amplification of the appropriate product from all 12 non-SMA tissues attempted and in only one of 12 SMA tissues. In the latter case, sample a12, amplification was from exons 13 to 4 only, whether the transcript also incorporates exons 2 to 3 or 14 to 17 is unknown. We believe that these data provide strong evidence for NAIP being the SMA gene.

Role of NAIP Protein

The discovery of a neuronal apoptosis inhibitor protein gene in the SMA region of chromosome 5 demonstrates that the SMA condition is a result of deletions in the apoptosis inhibitor protein domains. The long time survival of motorneurons is dependent on the production of complete neuronal apoptosis inhibitor protein. The deletion of the apoptosis inhibitor protein domain compromises the protein activity. We have demonstrated that approximately 70% of all SMA affected individuals have deletions of exons 5 and 6 of chromosome 5.

The identified region of 5q13.1 contains a variable number of copies of intact and partially deleted forms of the NAIP gene. While we cannot rule out the presence of additional loci in 5q13.1 that when mutated contribute to the SMA phenotype, we believe that mutations of NAIP gene are necessary and possibly sufficient for the genesis of SMA. In contrast to most autosomal recessive diseases where causal mutations are usually detected in the single copy of a given gene, we propose that an SMA chromosome is characterized by a paucity or, for severe SMA mutations, an absence of both the intact NAIP gene as well as that version which has had exons 3 and 4 deleted. The genesis of such chromosomes may involve unequal crossovers leaving the chromosome depleted for these loci with the resulting absence of the NAIP gene product leading to SMA.

Diagnosis of SMA

The delineation of an SMA genotype in a given individual is complicated by the unusual amplification of the NAIP gene in the 5q13.1 region. Probings of Southern blots containing genomic DNA with NAIP exon probes invariably reveal bands resulting from copies of internally deleted and truncated versions of the NAIP gene. The presence of variable numbers of the different forms of the NAIP loci in the general population is therefore the norm and not diagnostic of an SMA mutation per se, complicating the mutational analysis of the NAIP gene. If the detection of genomic DNA containing altered NAIP loci affords no proof of an SMA chromosome then, by default, the search must be for the absence of the normal NAIP gene. However, we have detected rare individuals with no copies of exons 3–4 in their genome who are clinically unaffected, an observation that is in keeping with what we know of NAIP gene structure. Consequently, the identification of an SMA chromosome is contingent on the absence of both the intact as well as the exons 3–4 only deleted forms of NAIP. Assaying for their absence is complicated by the presence of segments of normal NAIP gene in each of the other, more extensively deleted, forms of the NAIP locus. One can see, for example, that if a given SMA individual had in their genome only the deleted versions of NAIP found on PACs 238D12 and 30B2, that is exons 1–6 deleted and exons 5,6 and 11–14 deleted, respectively (FIGS. 10 and 11) in their genome, they would appear by PCR and Southern analysis to have the exons 5–6 only deleted version of NAIP and therefore to have non-SMA chromosomes. We believe that many and perhaps most of the numerous exon 5–6 deleted SMA individuals we have observed actually have chromosomes with such a configuration, containing neither the intact NAIP loci nor the exons 5–6 only deleted version but rather, some other combination of more severely truncated/deleted versions of the locus with resultant absence of intact NAIP translation. Support for this interpretation comes from our inability to amplify normal NAIP transcripts employing RT-PCR on RNA from Type I SMA tissue.

In all, the evidence in support of mutations in or the absence of the NAIP gene causing SMA includes the following:

(i) The strong possibility that the NAIP, given its homology with baculoviral IAPs, functions as an inhibitor of apoptosis. This characteristic is wholly compatible with the pathology of SMA. It is noteworthy that mutations in a regulator of apoptosis have been previously suggested as a speculative cause of SMA (Oppenheim 1991, Sarnat, 1992).

(ii) The mapping of the NAIP locus within the recombination defined critical SMA interval and the fact that the three polymorphic markers that have been shown to be in strong linkage disequilibrium with type I SMA; CATT-40GI (McLean et al., 1994), C272 (Melki et al., 1994) and AG-1 (DiDonato et al., 1994) all map to PAC 125D9 and are present on NAIP introns (FIG. 9C).

(iii) The nature of linkage disequilibrium observed between the type 1 SMA phenotype and the 5q13.1 markers. We have shown that the CATT-40G1 CTR sublocus which is frequently duplicated on non-SMA chromosomes (Roy et al., 1994), is deleted in 80% of type 1 SMA chromosomes compared with 45% of non-SMA chromosomes (McLean et al., 1994). This finding is in keeping with a depletion of the number of NAIP genes on SMA chromosomes. In a similar fashion, Melki et al., 1994, have observed "a heterozygote deficiency" consisting of a reduced number of bands for the C272 CTR in Type I SMA, reflecting, they propose, chromosomal deletions. DiDonato et al., (1994) have also seen a striking reduction in the number of AG1 CTR sub-loci in Type I SMA individuals when compared with non-SMA individuals. We believe that the observation by three groups of the depletion of these intraNAIP markers on Type I SMA chromosomes fits well with the proposed model of a lack or absence of both the intact and exon 5–6 deleted form of the NAIP gene underlying the disease.

(iv) The markedly increased frequency of NAIP exon 5–6 deletions observed in SMA chromosomes (approximately 67% of type 1 SMA chromosomes and 42% of type 2/3 SMA chromosomes) compared with that detected for non-SMA chromosomes (2–3%). As outlined above, we believe that this phenomenon reflects the rarity or absence of both the intact NAIP gene as well as the NAIP version with only exons 5 through 6 deleted in the SMA chromosomes, leaving only the more significantly internally deleted and truncated forms of the NAIP gene present.

(v) Our consistent inability to RT-PCR amplify appropriate size transcripts from RNA obtained from 11 of 12 SMA individuals despite success with 12 of 12 RNAs from non-SMA individuals. Furthermore, sequencing of those RT-PCR products that could be obtained from type 1 SMA material revealed a variety of mutations and deletions.

(vi) The presence of a variable number of copies of truncated and internally deleted versions of the NAIP gene is similar to the situation reported in the autosomal dominant polycystic kidney disease gene (ADPKD, European Polycystic Kidney Disease Consortium, 1994). In this case portions of unprocessed pseudogenes corresponding to the causative gene were found to map elsewhere on chromosome 16p. The key difference, is that with the NAIP locus the mutated form of the gene is amplified.

In this regard the NAIP region of 5q13.1 has more similarity to the area of chromosome 6 containing CYP21, the gene that encodes steroid 21-hydroxylase (Wedell and Luthman, 1993). CYP21, which when mutated causes an autosomal recessive 21-hydroxylase deficiency, has been observed in 0–3 copies in individuals. There also exists in the region a variable number of inactive pseudogene copies of CYP21 known collectively as CYP21P. The majority of the CYP21 mutations that have been observed in 21-hydroxylase deficiency can also be found in some form of CYP21P and it is thought that the pseudogenes act as a source of the mutations observed in CYP21. The truncated and internally deleted NAIP genes are analogous to CYP21P only instead of the gene conversion postulated for CYP21/CYP21P it is possible that unequal crossing over results in chromosomes deleted for forms of the NAIP gene that encode functional protein. The existence of a polymorphic number of mutated NAIP genes on 5q13.1 is a credible mechanism for generation of SMA chromosomes in this fashion.

Baculoviral IAPs

NAIP shows significant homology with the two baculoviral gene products, CpIAP and OpIAP, that are capable of inhibiting insect cell apoptosis (Table 4). Insect cell apoptosis following baculoviral infection has been well documented and is postulated to be a defence mechanism. Premature death of infected insect cells result in an attenuation of viral replication (Clem and Miller, 1994a). CpIAP and OpIAP are thought to represent baculoviral responses to this apoptotic mechanism. Both act independently of other viral proteins to inhibit host insect cell apoptosis, thereby permitting increased viral proliferation (Clem and Miller, 1994a, 1994b). They are known to be strongly similar only to each other; until now no sequences similarities with cross phyla proteins have been reported. Their mode of action is unknown, although some interaction with DNA has been postulated.

The role and cellular localization of NAIP has not yet been established. However, we believe that the significant sequence similarity between NAIP and the baculoviral IAPs, especially over such a considerable phylogenic distance, combined with the previously postulated role of inappropriate apoptosis in the pathogenesis of SMA make it likely that NAIP serves as an apoptosis inhibitor in the motor neuron. Transfection assays employing NAIP both in insect and mammalian neuronal cells will help in this regard.

One possibility is that specific ligand binding of the carboxy terminus of the NAIP activates the GTP binding site which in turn activates the IAP domain. The survival of a motor neuron might, therefore, be dependent on the presence of the ligand(s): should the concentration drop below a critical threshold, the IAP domains cease to function with ensuing cell death. This represents a possible mechanism for the natural winnowing of motor neurons observed in embryogenesis. The source of the ligand might be postulated to be either muscle cells or Schwann cells. The embryogenesis of motor neurons might, therefore, be viewed as a competition between the cells with only those that make sufficient contacts to maintain the NAIP occupancy rate surviving.

If, as postulated, NAIP does inhibit apoptosis, it is unclear whether NAIP is a constituent of a previously uncharacterized mammalian apoptotic pathway or a (presumably) upstream component of the pathway involving the human inhibitor of apoptosis, Bcl-2 (Vaux et al., 1988; Hockenberry et al., 1990; Garcia et al., 1992). Assays employing apoptosis inhibition deficient baculoviral strains have revealed that Bcl-2 does not complement the deficiency in such assays (Clem and Miller, 1994b). If NAIP is a functional homolog of the baculoviral IAPs, then this observation might suggest a role in a previously uncharacterized eucaryotic apoptotic pathway. One possibility is that NAIP represents an intersection of a novel apoptotic mechanism with the neurotrophic cytokine, ciliary neurotrophic factor (CNTF, Raff et al., 1993; Meakin and Shooter, 1993) or one of the downstream components of this pathway (Stahl et al., 1994). CNTF null mice show a pathologic picture that is similar to that of SMA with normal development of the neurons initially followed by their progressive apoptotic depletion (Masu et al., 1993). Moreover, although deprivation of neurotrophins under the right conditions may result in apoptosis of cultured neurons, it is noteworthy that CNTF is alone among these agents in not having such apoptosis rescued by Bcl-2. This finding led the workers who made the observation to suggest the presence of a second eucaryotic apoptotic pathway (Allsopp et al., 1993). The existence of such distinct pathways may underlie the synergistic effect observed with the marked retardation of motor neuron loss in the wobbler mouse mutant following treatment with brain derived neurotrophic factor (BDNF) and CNTF (Mitsumoto et al., 1994).

The role of the lipid attachment site in NAIP is unknown. Similar sites have been known to serve as procaryotic protein leader sequences usually situated in the protein's amino terminus. We have detected the consensus pattern in 218 human sequences in the Swiss-Protein Database (release 28). These sequences are present in a variety of functional settings; transmembrane regions, signal sequences, extracellular and cytoplasmic domains. One possibility is that the lipoprotein attachment site is extracellular and binds a constituent of the Schwann cell proteolipid in a manner that has been postulated for the apoptosis inhibiting interaction of integrin with the extracellular matrix (Meredith et al., 1993; Frisch and Francis, 1994). Furthermore, the site may play a more active role in the hepatic form of the NAIP that we have observed on Northern blot analysis. It is noteworthy that serum fatty acid abnormalities have been detected in children with SMA (Kelley and Sladky, 1986).

The identified region of 5q13.1 contains, in addition to the NAIP gene, a variable number of copies of internally deleted and truncated forms of the gene. We believe that a lack or absence of both the intact NAIP gene and the NAIP locus with exons 5 and 6 deleted from a given individual's genome are likely to cause SMA. In this regard, the identification of NAIP has allowed us to develop accurate molecular based diagnoses of SMA as well as directing the formulation of conventional and genetic therapies for these debilitating conditions. Furthermore, the identification of genes showing homology with the NAIPlocus and proteins that interact with NAIP may help in the continuing elucidation of apoptotic mechanisms in mammalian cells.

EXAMPLES

Family Material

Clinical diagnoses conducted as described in MacKenzie et al. (1993) with all patients fulfilling the diagnostic criteria given therein. DNA was isolated from peripheral leukocytes as described (MacKenzie et al., 1993).

Genetic and Linkage Disequilibrium Analyses

Genotyping with microsattelite markers was as outlined in MacKenzie et al. (1993) and McLean et al. (1994). The following 5q13.1 loci were used as described: D5S112 (Brzustowitcz et al., 1990), D5S351 (Hudson et al., 1992), D5S435 (Soares et al., 1993), D5S557 (Francis et al., 1993), D5S629 and D5S637 (Clermont et al., 1994), D5S684 (Brahe et al, 1994), Y98T, Y97T, Y116T, Y122T and CMS (Kleyn et al., 1993), CATT (Burghes et al., 1994, McLean et al., 1994) and MAP1B (Lien et al., 1991).

Linkage disequilibrium analyses were conducted using parameters that can accommodate the multiple alleles seen with microsatellite repeats. Given the complexities inherent in disequilibrium analyses, a total of 4 different parameters for which multiple alleles may be used were employed. These were Dij', Dij' and D' as defined in Hedrick (1987) as well as the chi square test. Two of these, Dij and Dij' have given the best a posteriori positional information in a previous study on myotonic dystrophy (Podolsky et al., 1994). The patient and control population is as outlined in McLean et al. (1994).

Cosmid, YAC and PAC Arraying

Cosmid and YAC contig assembly was as outlined in Roy et al. (1994). PACs were constructed as outlined in Ioannou et al. (1994). Using these procedures three PAC libraries have been constructed with a combined total of 175,000 clones and propagated as individual clones in microtiter dishes (Ioannou et al., unpublished results). Pools derived from the three libraries (designated LLNL PAC1, RPCI1 and RPCI2) were screened with 5q13.1 STS's. Positive PACs were arranged into a contiguous and overlapping arrays by further analysis with additional STSs combined with probings of Southern blots containing PAC DNA by single copy genomic DNA and cDNA probes.

DNA Manipulation and Analysis

Four genomic libraries containing PAC 125D9 insert were constructed by BamHI, BamHI/NotI, total and partial Sau3aI (selected for 5 kb insert size) digestions of the PAC genomic DNA insert and subcloned into Bluescript vector. Sequencing of approximately 400 bp of both termini of 200 five kb clones from the partial Sau3AI digestion library in the manner of Chen et al. (1993) was undertaken.

Coding sequences from the PACs were isolated by the exon amplification procedure as described by Church et al. (1994). PACs were digested with BamHI or BamHI and BglII and subcloned into pSPL3. Pooled clones of each PAC were transfected into COS-1 cells. After a 24 h transfection total RNA was extracted. Exons were cloned into pAMP10 (Gibco, BRL) and sequenced utilizing primer SD2 (GTG AAC TGC ACT GTG ACA AGC TGC).

DNA sequencing was conducted on an ABI 373A automated DNA sequencer. Two commercial human fetal brain cDNA libraries in lambda gt (Stratagene) and lambda ZAP (Clontech) were used for candidate transcript isolation. The Northern blot was commercially acquired (Clontech) and probing was performed using standard methodology.

In general, primers used in the paper for PCR were selected for $T_m$s of 60° C. and can be used with the following conditions: 30 cycles of 94° C., 60s; 60° C., 60s; 72° C., 90s. PCR primer mappings are as referred to in the figure legends and text. Primer sequences are as follows:

```
1258 ATg CTT ggA TCT CTA gAA Tgg  - SEQ ID NO: 3

1285 AgC AAA gAC ATg Tgg Cgg AA   - SEQ ID NO: 4

1343     CCA gCT CCT AgA gAA AgA Agg A - SEQ ID NO: 5

1844     gAA CTA Cgg CTg gAC TCT TTT - SEQ ID NO: 6

1863     CTC TCA gCC TgC TCT TCA gAT - SEQ ID NO: 7

1864     AAA gCC TCT gAC gAg Agg ATC - SEQ ID NO: 8

1884     CgA CTg CCT gTT CAT CTA CgA - SEQ ID NO: 9

1886     TTT gTT CTC CAg CCA CAT ACT - SEQ ID NO: 10

1887     CAT TTg gCA TgT TCC TTC CAA g - SEQ ID NO: 11
```

-continued

| | | |
|---|---|---|
| 1893 | gTA gAT gAA TAC TgA TgT TTC ATA ATT | - SEQ ID NO: 12 |
| 1910 | TgC CAC TgC CAg gCA ATC TAA | - SEQ ID NO: 13 |
| 1919 | TAA ACA ggA CAC ggT ACA gTg | - SEQ ID NO: 14 |
| 1923 | CAT gTT TTA AgT CTC ggT gCT CTg | - SEQ ID NO: 15 |
| 1926 | TTA gCC AgA TgT gTT ggC ACA Tg | - SEQ ID NO: 16 |
| 1927 | gAT TCT ATg TgA TAg gCA gCC A | - SEQ ID NO: 17 |
| 1933 | gCC ACT gCT CCC gAT ggA TTA | - SEQ ID NO: 18 |
| 1974 | gCT CTC AgC TgC TCA TTC AgA T | - SEQ ID NO: 19 |
| 1979 | ACA AAg TTC ACC ACg gCT CTg | - SEQ ID NO: 20 |

RT-PCR cDNA was synthesized in a 20 μl reaction utilizing 7 μg of total RNA. The RNA was denatured for 5 minutes at 95° C. and cooled to 37° C. Reverse transcription was performed at 42° C. for 1 hour after addition of 5 μl 5× reverse transtriction buffer, 2 μl 0.1 M DTT, 41 2.5 mM dNTPs, 8 units RNasin, 25 ng cDNA primer (1285) and 400 units of MMLV (Gibco, BRL). 1 μl of cDNA was utilized as template in subsequent 50 μl PCR reactions. 1 μl of this primary PCR was utilized as template for secondary PCR amplifications.

Sequence Analysis

Primary DNA sequence data was edited with the TED program (Gleeson and Hillier, 1991). As many of the partially sequenced 200 five kb clones from the partial Sau3AI digestion library as possible were arranged into overlapping arrays using the XBAP Staden package (Dear and Staden, 1991). Sequence data was also assembled and analyzed using the GCG Sequence analysis (Genetics computer group, 1991). Protein domain homologies were found by searching the Prosite Protein database (Bairoch and Bucher, 1993). The MEMSAT program was also used to search for transmembrane domain regions (Jones et al., 1994).

TABLE 1

The YACs isolated in this study, their size and library of origin are listed. NCE: National Centers of Excellence, Toronto, Ontario, Canada. ICRF: Imperial Cancer Research Fund, CEPH: Centre d'Etude du Polymorphisme Humaine.

| YAC | SIZE | LIBRARY |
|---|---|---|
| 12H1 | 560 kb | NCE |
| 12H4 | 270 kb | NCE |
| 24D6 | 750 kb | NCE |
| 27H5 | 630 kb | NCE |
| 33H10 | 1.3 Mb | NCE |
| H0416 | 390 kb | ICRF |
| E0320 | 440 kb | ICRF |
| G1138 | 850 kb | ICRF |
| A0848 | 350 kb | ICRF |
| D06100 | 580 kb | ICRF |
| D0981 | 450 kb | ICRF |
| 919C2 | 800 kb | CEPH |
| 755B12 | 1 Mb | CEPH |
| 754H5 | 500 kb | CEPH |

TABLE 2

| PROBE | SOURCE/REFERENCE | PROBE | SOURCE/REFERENCE |
|---|---|---|---|
| YD33 | STS developed from, Alu-5'-trp PCR product of YAC D06100 | Y13.1 | STS developed from inter Alu-5' PCR product of YAC 12H1 (this study) |
| Y14.1 | STS developed from Alu-3'-ura PCR product of YAC 12H4 (this study) | Y15.1 | STS developed from Alu-5'-ura PCR product of YAC 12H4 (this study) |
| Y9.2 | STS developed from inter-Alu-5' PCR product of YAC 27H5 (this study) | Y5.6 | STS developed fron inter-Alu-3'PCR product of YAC 24D6 (this study) |
| Y11.2 | STS developed from Alu-3'-trp PCR product of YAC 33H10 (this study) | pZY8 | subcloned 1.3 kb HindIII fragment from cosmid 250B6 (this study) |

TABLE 2-continued

| PROBE | SOURCE/ REFERENCE | PROBE | SOURCE/ REFERENCE |
|---|---|---|---|
| H7T733 | Alu 33-T7 PCR product from cosmid 1H7 (this study) | p151.2 | subcloned 1.2 kb inter-Alu PCR product of cosmid 15F8 (this study) |
| G10T333 | Alu 33-T3 PCR product of cosmid IG10 (this study) | p402.1 | subcloned 2.1 kb Bam HI/HindIII fragment of cosmid 40GI (this study) |
| G3T733 | Alu 33-T3 PCR product of cosmid IG3 (this study) | pL7 | liver transcript isolated with subcloned 1.1 kb BamHI/SalI fragment from 58G12 (this study) |
| p2281.8 | subcloned 1.8 kb HindIII fragment of cosmid 228C8 (this study) | F933 | inter-Alu PCR product of cosmid 1F9 (this study) |
| pGA1 | fetal brain transcript isolated with cosmid 250B6 (Lien et al. 1991) | β-glucuronidase | (Oshima et al. 1987) |
| MAP1B | (Lien et al. 1991) | Y122T | (Kleyn et al., 1993) |
| D5S351 | (Yaraghi et al., in press) | CMS-1 | (Kleyn et al., 1993) |
| D5S557 | (Francis et al, 1993) | Y98T | (Kleyn et al., 1993) |
| D5S112 | (Brzustowitcz et al., 1990) | Y97T | (Kleyn et al., 1993) |
| Y112U | (Kleyn et al., 1993) | Y88T | (Kleyn et al, 1993) |
| Y119T | (Kleyn et al, 1993) | Y116U | (Kleyn et al., 1993) |
| CATT-1 | (Burghes et al., 1994; McLean et al., in press) | Y55U | (Kleyn et al., 1993) |
| D5S127 | (Sherrington et al., 1991) | Y38T | (Kleyn et al., 1993) |
| D5S435 | (Soares et al., 1993) | D5S125 | (Hudson et al., 1992) |
| Y107U | (Kleyn et al., 1993) | Y97U | (Kleyn et al., 1993) |
| D5F149 (C212) | (Melki et al., 1994) | D5F151 (C171) | (Melki et al., 1994) |
| D5F150 (C272) | (Melki et al., 1994) | D5F153 (C161) | (Melki et al., 1994) |
| D5S637 | (Clermont et al., 1994) | D5S629 | (Clermont et al., 1994) |

TABLE 3

The homology of the GA1 component of neuronal apoptosis inhibitor protein gene (SEQ ID NO: 23) compared for homology with the inhibitor apoptosis polypeptides of the viruses Cydia pomenella (SEQ ID NO: 21) and Orgyia pseudotsugata (SEQ ID NO: 22).

```
                    1                                                50
Cydia pomonella     .......... .......... .......... .......... ..........
Orgyia pseudots     .......... .......... .......... .......... ..........
cGA1-concensus      TRTVDKPQKM ATQQKASDER ISQFDHNLLP ELSALLGLDA VQLAKELEEE 51                                               100
Cydia pomonella     .......... .......... .......... .......... ..........
Orgyia pseudots     .......... .......... .......... .......... ..........
cGA1-concensus      EQKERAKMQK GYNSQMRSEA KRLKTFVTYE PYSSWIPQEM AAAGFYFTGV 101                                              150
Cydia pomonella     .......... .......... .......... .......... ..........
Orgyia pseudots     .......... .......... .......... .......... ........MS
cGA1-concensus      KSGIQCFCCS LILFGAGLTR LPIEDHKRFH PDCGFLLNKD VGNIAKYDIR 151                                              200
Cydia pomonella     .........M SDLR..LEEV RLNTFEKWP. .VSFLSPETM AKNGFYYLGR
Orgyia pseudots     SRAIGAPQEG ADMK..NKAA RLGTYTNWP. .VQFLEPSRM AASGFYYLGR
cGA1-concensus      VKNLKSRLRG GKMRYQEEEA RLASFRNWPF YVQGISPCVL SEAGFVFTGK 201                                              250
Cydia pomonella     SDEVRCAFCK VEIMRWKEGE DPAADHKKWA PQCPFVKGID VCGSI.....
Orgyia pseudots     GDEVRCAFCK VEITNWVRGD DPETDHKRWA PQCPFVRN.. ..........
cGA1-concensus      QDTVQCFSCG GCLGNWEEGD DPWKEHAKWF PKCEFLRSKK SSEEITQYIQ
```

TABLE 3-continued The homology of the GA1 component of neuronal apoptosis inhibitor protein gene (SEQ ID NO: 23) compared for homology with the inhibitor apoptosis polypeptides of the viruses Cydia pomenella (SEQ ID NO: 21) and Orgyia pseudotsugata (SEQ ID NO: 22).

```
                     251                                                         300
Cydia pomenella      .......VTT NNIQNTTTHD TIIGPA.... HPKYAHEAAR VKSFHNWPRC
Orgyia pseudots      ........NA HDTPHDRAPP ARSAAA.... HPQYATEAAR LRTFAEWPRG
cGA1-concensus       SYKGFVDITG EHFVNSWVQR ELPMASAYCN DSIFAYEELR LDSFKDWPRE 301                                                         350
Cydia pomenella      MKQRPEQMAD AGFFYTGYGD NTKCFYCDGG LKDWEPEDVP WEQHVRWFDR
Orgyia pseudots      LKQRPEELAE AGFFYTGQGD KTRCFCCDGG LKDWEPDDAP WQQHARWYDR
cGA1-concensus       SAVGVAALAK AGLFYTGIKD IVQCFSCGGC LEKWQEGDDP LDDHTRCFPN 351                                                         400
Cydia pomenella      CAYVQLVKGR DYVQKVI... TEACVLPGEN TTVSTAAPVS EPIPETKIEK
Orgyia pseudots      CEYVLLVKGR DFVQRVM... TEACVVRDAD N......... ....EPHIER
cGA1-concensus       CPFLQNMKSS AEVTPDLQSR GELCELLETT SESNLEDSIA VGPIVPEMAQ 401                                                         450
Cydia pomenella      .......EPQ VEDSKLCKIC YVEE...... .......CIV CFVPCGHVVA
Orgyia pseudots      PAV....EAE VADDRLCKIC LGAE...... .......KTV CFVPCGHVVA
cGA1-concensus       GEAQWFQEAK NLNEQLRAAY TSASFRHMSL LDISSDLATD HLLGCDLSIA 451                                                         500
Cydia pomenella      CAKCALSVDK CPMCRKIVTS VLKVYFS... .......... ..........
Orgyia pseudots      CGKCAAGVTT CPVCRGQLDK AVRMYQV... .......... ..........
cGA1-concensus       SKHISKPVQE PLVLPEVFGN LNSVMCVEGE AGSGKTVLLK KIAFLWASGC 501                                                         550
cGA1-concensus       CPLLNRFQLV FYLSLSSTRP DEGLASIICD QLLEKEGSVT EMCMRNIIQQ
cGA1-concensus       LKNQVLFLLD DYKEICSIPQ VIGKLIQKNH LSRTCLLIAV RTNRARDIRR
cGA1-concensus       VLETILEIQA FPFYNTVCIL RKLFSHNMTR LRKFMVYFGK NQSLQKIQKT
cGA1-concensus       PLFVAAICAH WFQYPFDPSF DDVAVFKSYM ERLSLRNKAT AEILKATVSS
cGA1-concensus       CGELALKGFF SCCFEFNDDD LAEAGVDEDE DLTMCLMSKF TAQRLRPFYR
cGA1-concensus       FLSPAFQEFL AGMRLIELLD SDRQEHQDLG LYHLKQINSP MMTVSAYNNF
cGA1-concensus       LNYVSSLPST KAGPKIVSHL LHLVDNKESL ENISENDDYL KHQPEISLQM
cGA1-concensus       QLLRGLWQIC PQAYFSMVSE HLLVLALKTA YQSNTVAACS PFVLQFLQGR
cGA1-concensus       TLTLGALNLQ YFFDHPESLS LLRSIHFSIR GNKTSPRAHF SVLETCFDKS
cGA1-concensus       QVPTIDQDYA SAFEPMNEWE RNLAEKEDNV KSYMDMQRRA SPDLSTGYWK
cGA1-concensus       LSPKQYKIPC LEVDVNDIDV VGQDMLEILM TVFSASQRIE LHLNHSRGFI
cGA1-concensus       ESIRPALELS KASVTKCSIS KLELSAAEQE LLLTLPSLES LEVSGTIQSQ
cGA1-concensus       DQIFPNLDKF LCLKELSVDL EGNINVFSVI PEEFPNFHHM EKLLIQISAE
cGA1-concensus       S
```

TABLE 4

Complete cDNA sequence and predicted amino acid sequence SEQ ID NO: 2 of NAIP. Nucleotide residues G are in lower case "g", to clearly delineate the residue C. Exon boundaries are as marked. Arrows underline the perfect 90 nucleotide tandem repeat in the 5' UTR region. The deleted exons 5 and 6 are shaded in gray. The regions of intra-protein repeated amino acid homology in the IAP domain are underlined. Sequence comparison with baculovirus IAPs is shown, identical residues are shaded dark grey and similar residues are shaded light grey. CpIAP and OpIAP refer to the IAPs encoded by the baculoviruses, *Cydia pomonella granulosis virus* (CpGV) and *orygia pseudotsugata nuclear polyhydosis virus* (OpMNPV), respectively. The sequence comparison has been extended to the cysteine/histidine putative DNA interacting region of the baculoviral IAPs, no NAIP homology can be seen. The region showing significant similarity to chicken occludin is shown in grey in the 3' UTR.

```
                10              30              50              70              90             110
                 .               .               .               .               .               .
  1  TTCCGGCTGGAGCTTGCCCTGTGTACCTCTTCGACTTCATCTGACTGACGTACTACGAACCCGGGTATTGACCCCAGACAACAATGCCACTTCATATTGCATGAAGACAAAAGGTCCTGTGC  120
                                                                                                        1

121  TCACCTGGGACCCTTCGTTGCCCTGTTGTCCCTGTTCTCGCCTGCCTGTCTTCATCTACGACGAACAACCCGGTATTGACCCCAGAGAACAACAATGCCACTTCATATTGGGGACTTCGTCTCGG  240

241  GATTCCAAGGTGCATTCATTGCAAAGTTCCTTAAATATTTTCTCACTGCTTCCTACTAAAGGACGACAGAGCATTTGTTCTTCAGCCACCACATACTTCCTTCCACTGGCCAGCATTCTCC  360
                                          2                      3
                                                                4
361  TCTATTAGACTAGAACCTGTGATAAACCTCAGAAATGGCCACCCAGCAGAAAGCGGCCTCACCAGCAGAAGCACCTCACAGTTCCCAGTTGATCACGAAAATGGCCAAGTTTGTGA  480
       1                                  M  A  T  Q  Q  K  A  S  D  E  R  I  S  Q  F  D  H  N  L  P  E  L  S  A  L  L  G  L   29

481  TAGATGCAGTTCAGTTGCAGCTCAGTTGCAAAGGAACTAGAAGCAGGAGCAGCCAAAGCGCCAAAATGCCAGCAGCAGAATGCCAAGCCTACAAACTTCCAAAATGCCGAAGCAGAAAACTTCCAGCAGAAGCAAAAGGGTAAAAATCGGGATTCAGTGCCTGCAAGTGCCTTTCCTTTCCTTTCCTCTTCCGCCGCC  600
       D  A  V  Q  L  A  K  E  L  E  E  E  Q  K  E  R  A  K  M  Q  K  G  Y  N  S  Q  M  R  S  E  A  K  R  L  K  T  F  V  T    69

601  CTATATGGCCGTACAGCTCAGATAACCCAGATGCCACAGAAGATGGGGCCCCTTGGTTTACTTCAGTGGTAAAATCTGGAATCCAGTGCTTCTGCTCCTTATCATCCTCTTCGCCGCT  720
       Y  E  P  Y  S  S  W  I  P  Q  E  M  A  A  A  G  F  Y  F  T  G  V  K  S  G  I  Q  C  F  C  C  S  L  I  L  F  G  A  G  L   109

721  TCACGGAGACTCCCCATAGAAGACCACAAGAGGTTTCATCCAGATGTGGGGTTTCTTTTGAACAAGGACGTTGGAAACATTGCCAAGTACGACATCAGAGTGAAGAATCTGAAGAGCAGGC  840
       T  R  L  P  I  E  D  H  K  R  F  H  P  D  C  G  F  L  L  N  K  D  V  G  N  I  A  K  Y  D  I  R  V  K  N  L  K  S  R  L   149

M  S  S  R  A  I  G  A  P  Q   10
                                                                                                          OpIAP
```

Deleted Exons (light grey)

repeat

TABLE 4-continued

TABLE 4-continued

TABLE 4-continued

```
3121  GCTTGTCATTGTTGAGGAGCATCCACTTCTCAATGAGACAGAGGAAATAAGACACATTTTCAGTTCTGAAACATGTTTGACAAATCACAGGTGCCAACTATAGATCAGG   3240
910    L  S  L  L  R  S  I  H  F  S  I  R  G  N  K  T  S  P  R  A  H  F  S  V  L  E  T  C  F  D  K  S  Q  V  P  T  I  D  Q  D   949

3241  ACTATGCTTCTGCCTTTGAACCTATGAATGAATGGGAGCCAAATTTACTGAAAAAGAGGATAAATGTAAAGAGCTATATGGATATGCAGCCCAGGCATCACCAGACCTTAGTACTGCT   3360
950    Y  A  S  A  F  E  P  M  N  E  W  E  R  N  L  A  E  K  E  D  N  V  K  S  Y  M  D  M  Q  R  R  A  S  P  D  L  S  T  G  Y   989

3361  ATTGGAAACTTTCTCCAAAGCAGTAGCAGTTCCCTGTCTAGAAGTCCATGTGAATGATATTGATGTTGTAGGCCAGGATATGCTTGAGATTCTAATGACAGTTTTCTCAGCTTCACAGC   3480
990    W  K  L  S  P  K  Q  Y  K  I  P  C  L  E  V  D  V  N  D  I  D  V  V  G  Q  D  M  L  E  I  L  M  T  V  F  S  A  S  Q  R   929

3481  GCAATCGAACTCCATTTAAACCACAGCAGGCTTTATAGAAAGCATCCGCCCAGCTCTTGAGCTGTCTAAGGCCTCCATAAGCCAAGTGCTCCATCAGCCAGCCG   3600
1030   I  E  L  H  L  N  H  S  R  G  F  F  I  E  S  I  R  P  A  L  E  L  S  K  A  S  V  T  K  C  S  I  S  K  L  E  L  S  A  A  E   969

3601  AACAGGAACTGCTTCTCACCCTGCCTTCCCTGGAATCTCTTGAAGTCTCAGGGACAATCCAGTCAGGATCAAATCTTCCCTAATCTGGATAAGTTCCTGTGCCTGAAAGAACTGTCTG   3720
1070   Q  E  L  L  L  T  L  P  S  L  E  S  L  E  V  S  G  T  I  Q  S  Q  D  Q  I  F  P  N  L  D  K  F  L  C  L  K  E  L  S  V   1009

3721  TGGATCTCGAGGCAATATAAATGTTTTTCAGTCATTCCTGAAGAATTTCCTGAAGAATTTCCAAACTTCAGCTGACTATGATCCTTCAAAGTTGGTGGCA   3840
1110   D  L  E  G  N  I  N  V  F  S  V  I  P  E  E  F  P  N  F  H  H  M  E  K  L  L  I  Q  I  S  A  E  Y  D  P  P  S  K  L  V  A   1049
                                                                                                                    13

3841  CCAGTTTGCCAAATTTTTATTTCTGAAGATATTAAATCTTGAAGGCCAGCAATTTCCTGATGAGGAATCAGAAAAATTTGCTTACATTTTAGGTTCTCTTAGTAATCTTGAGGAAT   3960
1150   S  L  P  N  F  I  S  L  K  I  L  N  L  E  G  Q  Q  F  P  D  E  E  T  S  E  K  F  A  Y  I  L  G  S  L  S  N  L  E  E  L   1089
                                                                                                                14

3961  TGATCCTTCCTACTGGGGATGGAATTTATCGAGTAGCAAAACTGATTATTCAGCAGTGTCAGCAGCTTCATTGCCTGAGAGTTCTGTCATTTTTCAAGACATTGAATGATGATAGTGTGG   4080
1190   I  L  P  T  G  D  G  I  Y  R  V  A  K  L  I  I  Q  Q  C  Q  Q  L  H  C  L  R  V  L  S  F  F  K  T  L  N  D  D  S  V  V   1129
                                                                                                        15

4081  TGGAAATTGGTAAAAATGTCTAAACACTTCAACTGAGAGATGGACAGAGCAGCTTCCTCCAATGGCAAAGTGAATGACAAAG   4200
1230   E  I  G    End                                                                                                         1232

4201  CGGTTTTATCCAGACTTCCAGACTGGTTCCCTGTGGAGGGTTCAGGAGTGGCATTAACTTCTGCCTCTGATGAGAGCTTCAGGCAGCCTCCTTTACAGCAGCGCGTAACTTT   4320
4321  CAGACACCTTCCAAAAGCACCTGCAAAAGGCAAAGACGAAAGCCAGGAGGCCGCAAACAGAAGAGCCATTGCAGCACAACTGGCCGCCGGCTCTGTATGAGCCCAGGAAA   4440
4441  CACTGGATCAGTAAGATGATCCACCCATCCTTTCAGCATCCCTATAGACAAAGATAACATTTTGCACACTGGCCTGCCCATCAAATACAATAGACATCAGAAGCTGACAGTTCACAGTAA   4560
4561  AAGAACTCTCCCGTTTGCAAAATCCCGGATGGAAAGACAAATTTCCATTCACTTCAGCATGCCTACATGCTGCTCTGAACCCATGAGCACCTGGAATTACAACACTGTCAAGACTACAAT   4680
4681  AGTAAGCAGAATCATTGCCAAGCAGTTAAACACGGTAAACACCAAATTGCTCCAGCCATCAAGAGAGCATAGAGCAAAGGCTGATGCCAAGCTGTTTGAGAATTAAGT   4800
4801  ATCTGACAATCTCTGCAATCTTCAGAGAGCAAATGACTTTTGAACACTTCAGAGGATTTATGCTTAAACATTGGTCTTGTATTAAGAAAATACGTTTAGCCTTAAGGAAGG   4920
4921  ATAAATCGCTTTGATAATCAACTGGGCTGAACACTCAATTAAAGACAGAGGCCTTCCAACGATGTCTTCATACCTACACGTATTTGTTGCATAGGTATTCATTTAACTCCTCAGATAACTGTTATTATAT   5040
5041  TTCTGGTGTGAACTAAACTTTCCACACCCAGGAAACTGGGTTCCTGCAATGAAGTCTCTCAATGAAACTCTCCACACACTTTTGTTTCCATCCATCCTGCTTCATAGTCTGTTTATGAGTCTGTATTTATATT   5160
5161  CACTTTTTTCCACATAAGGAAACTGGGTTCCTGCCAATGAAGTCTCTCAATGAAACTCTCCACACACTTTTGTTTCCATCCATCTGGCTTCATAGTCTGTTTATGACTTCATTAATAAATTCC   5280
5281  GGCATCATACAGCTACTCCTCCCACACCCCACATTATCTACAAACTGATGACTCCTAATTTACATCTCCAGCCTCCAGACCTCCAATCCCAACGCATACAC   5400
5401  GGTGATCCCTGAGTCTCCGAGTCTCCCCACACCCCACATTATCTACAAACTGATGACTCCTAATTTACATCTCCAGCCTCCAGACCTCCAATCCCAACGCATACAC   5502

ORF with homology to occludin
```

REFERENCES

1. Albertson, H. M., Abderrahim, H., Cann, H. M., Dausset, J., le Paslier, D. and Cohen, D. (1990). Construction and characterization of a yeast artificial chromosome library containing seven haploid genome equivalents. *Proc. Nat Acad. Sci. USA*. 87: 4256–4260.
2. Allsopp., T. E. Wyatt, S., Paterson, H. F., and Davies, A. M. (1993). The Proto-Oncogene bcl-2 Can Selectively Rescue Neutrophic Factor-Dependent Neurons from Apoptosis. *Cell* 3073, 295–307.
3. Bairoch, A., and Bucher, P., (1994) PROSITE: Recent Developments. *Nucl. Acids Res.* 22:3583–3589.
4. Birnbaum, M. J., Clem, R. J., and Miller, L. K. (1994). An apoptosis-inhibiting gene from a nuclear polyhedrosis virus encoding a polypeptide with Cys-His sequence Motifs. *J. Virol.* 68, 2521–2528.
5. Birnboim, H. C.,and Doly, J. (1979). A rapid alkaline extraction procedure for screening recombinanat plasmid DNA. *Nucleic Acids. Res.* 7: 1513–1523.
6. Boultwood, J., Fidler, C., Lewis, S., Kelly, S., Sheridan, H., Littlewood, T. J., Buckle, V. J. and Wainscoat, J. S. (1994). Molecular mapping of uncharacteristically small 5q deletions in two patients with the 5q- syndrome: delineation of the critical region on Sq and identification of a 5q- breakpoint. *Genomics* 19: 425–432,
7. Burghes, A. H. M., Ingraham, S. E., McLean, M., Thompson, T. G., McPherson, J. D., Kote-Jarai, Z., Carpten, J. D., DiDonato, C. J., Ikeda, J-E., Surh, L., Wirth, B., Sargent, C. A., Ferguson-Smith, M. A., Fuerst, P., Moysis, R. K., Grady, D. L., Zerres, K., Korneluk, R., MacKenzie, A. and Wasmuth, J. J. (1994). A multicopy dinucleotide marker that maps close to the spinal muscular atrophy gene. *Genomics* 21: 394–402.
8. Brzustowitcz, L. M., Lehner, T., Castilla, L. H., Penchaszadeh, G. K., Wilhelmsen, K. C., Daniels, R., Davies, K. E., Leppert, M., Ziter, F., Wood, D., Dubowitz, V., Zerres, K., Hausmanowa-Petrusewicz, I., Ott, J., Munsat, T. L. and Gilliam, T. C. (1990). Genetic mapping of chronic childhood-onset spinal muscular atrophy to chromosome 5q11.2–13.3. *Nature* 344: 540–541.
9. Church, D. M., Stotler, C. J., Rutter, J. L., Murrell, J. R., Trofatter, J. A., and Buckler, A. J. (1994). Isolation of genes from complex sources of mammalian genomic DNA using exon amplification. *Nature Genet.* 6, 98–105.
10. Clem, R. J., and Miller, L. K. (1994a). Induction and Inhibition of Apoptosis by Insect Viruses. Apoptosis II: The Molecular Basis of Apoptosis in Disease, Cold Spring Harbour Laboratory Press pp. 89–110.
11. Clermont, O., Burlet, P., Burglen, L., Lefebvre, S., Pascal, F., McPherson, J., Wasmuth, J., Cohen, D., Le Paslier, D., Weissenbach, J., Lathrop, M., Munnich, A., and Melki, J. (1994). Use of genetic and physical mapping to locate the spinal muscular atrophy locus between two new highly polymorphic DNA markers. *Am. J Hum, Genet.* 54: 687–694.
12. Dana, S., and Wasmuth, J. J. (1982). Linkage of the leuS, emtB, and chr genes on chromosome 5 in humans and expression of human genes encoding protein synthesis components in human-Chinese hamster hybrids. *Somatic Cell Genet.* 8: 245.
13. Davis, L. G., Dibner, M. D. and Battey, J. F. (1986). Basic Methods in Molecular Biology. Elsevier, New York.
14. Dear, S., and Straden, R. A. (1991). A Sequence Assembly and Editing Program for Efficient Management of Large Projects. *Nucl. Acids. Res.* 19, 3907–3911.
15. DiDonato, C. J., Morgan, J., Carpten, J. D., Fuerst, P., Ingraham, S. E., Prescott, McPherson, J. D., Wirth, B., Zerres, K., Hurko, O., Wasmuth, i.i., Mendell, J. R., and Burghes, A. H. M. (1994). Association between Agl-CA Alleles and Severity of Autosomal Recessive Proximal Spinal Muscular Atrophy. *Am. J. Hum. Genet.* (in press).
16. Dubowitz, V. (1978). Muscle Disorders in Childhood, W. B. Saunders Co. Ltd., East Sussex, pp. 146–190.
17. Dubowitz, V, (1991). Chaos in classification of the spinal muscular atrophies of childhood. *Neuromusc. Disord.* 1: 47–53.
18. Feinberg, A. P. and Vogelstein, B. (1983). A technique for radiolabeling DNA restriction endonuclease fragments to high specific activity, *Anal. Biochem.* 132: 6–13.
19. Francis, M. J., Morrison, K. E., Campbell, L., Grewal, P. K., Christodoulo, Z., Daniels, R. J., Monaco, A. P., Frichauf, A. M., McPherson, J., Wasmuth, J. and Davies, K. E. (1993). A contig of non-chimeric YACs containing the spinal muscular atrophy gene in 5q13. *Hum. "Mol. Genet.* 2: 1161–1167.
20. Frisch, S. M., and Francis, H., (1994) Disruption of Epithelial Cell-Matrix Interactions Induces Apoptosis. *J. Cell Biol.*, 124, 619–626.
21. Garcia I. Martinou I Tsujimoto, Y. Martinou J. C. (1992) Prevention of Programmed Cell Death of Sympathetic Neuron by the bcl-2 proto-oncogene. *Science* 258:302–304.
22. Gilliam, T. C., Freimer, N. B., Kaufmann, C. A., Powhik, P. P., Bassett, A.S., Bengtsson, U., and Wasmuth, J. J. (1989). Deletion mapping of DNA markers to a region of chromosome 5 that cosegregates with schizophrenia. *Genomics* 5: 940–944.
23. Gilliam, T. C., Brzustowitcz, L. M., Castillo, L. H., Lehner, T., Penchaszadeh, G. K., Daniels, R. J., Byth, B, C., Knowles, J., Hislop, J. E., Shapira, Y., Dubowitz, V., Munsat, T. L., Ott, J. and Davies, K. E. (1990). Genetic homogeneity between acute and chronic forms of spinal muscular atrophy. *Nature* 345: 823–825.
24. Gleeson, R., and Hillier, L. (1991). A Trace Display and Editing Program for Data from Fluorescence Based Sequencing Machines. *Nucl. Acids. Res.* 19, 6491–643, 47.
25. Hedrick, P. W. (1987). Gametic Disequilibrum Measures: Proceed with Caution. *Genetics* 117, 331–341.
26. Hockenberry, D., Nunez, G., Millman, C., Schreiber, R. D., and Korsmeyer, S. J. (1990) Bcl-2 is an Inner Mitochondrial Membrane That Blocks Programmed Cell Death. *Nature* 348, 334–336.
27. Hudson, T. J., Englestein, M., Lee, M. K., Ho, E. C., Rubenfield, M. J., Adams, C. P., Housman, D. E., and Dracopoli, N. C. (1992). Isolation and chromosomal assignment of 100 highly informative human simple sequence repeat polymorphisms. *Genomics* 13: 622–629.
28. Ioannou, P. A., Amemiya, C. T., Garnes, J., Droisel, P. M., Shizuya, H., Chen, C., Batzer, M. A., de Jong, P. J. (1994). A New Bacteriophage Pi-derived Vector for the Propogation of Large Human DNA Fragments. *Nature Genet.* 6, 84–89.
29. Jones, D. T., Taylor, W. R., and Thornton, J. M. (1994). A Model Recognition Approach to the Prediction of All-Helical Membrane Protein Structure and Topology. *Biochemistry* 33, 3038–3049.
30. Kleyn, P. W., Wang, C. H., Lien, L. L., Vitale, E., Pan, J., Ross, B. M., Grunn, A., Palmer, D. A., Warburton, D., Brzustowicz, L. M., Kunkel, L. M. and Gilliam, T. C. (1993). Construction of a yeast artificial chromosome contig spanning the spinal muscular atrophy disease gene region. *Proc. NaH Acad. Sci. USA* 90: 6801–6805.
31. Kouprina, N., Eldarov, M., Moyzis, R., Resnick, M. and Larionov, V. (1994). A model system to assess the integrity of mammalian YACs during transformation and propagation in yeast. *Genomics* 21: 7–17.
32. Larin, Z., Monaco, A. P. and Lehrach, H. (1991). Yeast artificial chromosome libraries containing large inserts from mouse and human DNA. *Proc. Natl. Acad Sci USA* 87: 4123–4127.
33. Lien, L. L., Boyce, F. M., Kleyn, P., Brzustowicz, L. M., Menninger, J., Ward, D. C., Gilliam, T. C., and Kunkel, L. M. (1991). Mapping of human microtubule associated protein 1B in proximity to the spinal muscular atrophy locus at 5q13.1 *Proc. Natl. Acad Sci.* 88: 7873–7876.
34. MacKenzie, A., Roy, N., Besner, A., Mettler, G., Jacob, P., Korneluk, R. and Surh, L. (1993). Genetic linkage analysis of Canadian spinal muscular atrophy kindreds using flanking microsatellite 5q13 polymorphisms. *Hum. Gen.* 90: 501–504.
35. Mankoo, B. S., Sherrington, R., De La Concha, A., Kalsi, G., Curtis, D., Melmer, G. and Gurling, H. M. D. (1991). Two microsatellite polymorphisms at the D5S39 locus. *Nucleic Acids Res.* 19: 1963.
36. McLean, M. D., Roy, N., MacKenzie, A. E., Salih, M., Burghes, A., Simard, L., Korneluk, R. G., Ikeda, J-E, and Surh, L. Two 5q13 simple tandem repeat loci are in linkage disequilibrium with type I spinal muscular atrophy. *Hum. Mol. Genet.*, In Press.
37. McLean M., Roy, N., Yaragi, G., Shutler, K., Tamai, Mahadevan S., Salih, M., Besner, A., Lefebvre, C., Kang, X., Aubry, H., Baird, S., Surh, L., Korneluk, R., MacKenzie, A. and Ikeda, J-E. 1994 Molecular genetics analysis of the spinal muscular atrophy region on 5Q13.1. Ikeda GenoSPERE Project. 31–35.
38. Melki, J., Abdelhak, S., Sheth, P., Bachelot, M. F., Burlet, P., Marcadet, A., Aicardi, J., Barois, A., Carriere, J. P., Fardeau, M., Fontan, D., Ponsot, G., Billsette, T., Angeline, C., Barbosa, C., Ferriere, G., Lanzi, G., Ottolini, A., Babron, M. C., Cohen, D., Hanauer, A., Colerget-Darpox, F., Lathrop, M., (1993) Refined Linkage Map of Chromosome 5 in the Region of the Spinal Muscular Atrophy Gene, *Genomics* 15:521–541.
40. Meredith, J. E., Fazeli, B., and Schwartz, M. A. (1993). The Extracellular Matrix as a Cell Survival Factor. *Mol. Biol. Cell* 4, 953–961.
41. Munnich, A. and Frezal, J. (1990). Gene for chronic proximal spinal muscular atrophies maps to chromosome 5q. *Nature* 344: 767–768.
42. Melki, J., Lefebvre, S., Burglen, L., Burlet, P., Clermont, O., Millasseau, P., Reboullet, S., Benichou, B., Zevianai, M., LePaslier, D., Cohen, D., Weissenbach, J, and Munnich, A. (1994). De novo and inherited deletions of the 5q13 region in spinal muscular atrophies. *Science* 264: 1474–1477.
43. Neil, D. L., Villasante, A., Fisher, R. B., Vetrie, D., Cox, B. and Tyler-Smith, C. (1990). Structural instability of human tandemly repeated DNA sequnces cloned in yeast artificial chromosome vectors. *Nucleic Acid Res.* 18: 1421–1428.
44. Nelson, D. L., Brownstein, B. H. (eds) (1993). YAC libraries: A users guide. W. H. Freeman and Company, New York pp. 86–89.
45. Meakin, S. O., and Shooter, E. M. (1992). The Nerve Growth Factor Family of Receptors. TINS 9, 32.3–331.
46. Oppenheim, R. W. (1991). Cell death during development of the nervous system. *Annu. Rev. Neurosci.* 14, 5453–501.
47. Oshima, A., Kyle, J. W., Miller, R. D., Hoffmann, Powell, P. P., Grubb, J. H., Sly, W. S., Tropak, M., Guise, K. S., and Gravel, R. A. (1987). Cloning, sequencing and expression of cDNA for human beta-glucuronidase. *Proc. Natl. Acad. Sci. USA*. 84: 685–689.
48. Podolsky, L., Tsilfidis, C., Baird, S., Korneluk, R. G., and MacKenzie, A. E. (1994). An Empiric Comparison of Linkage Disequilibrium Parameters in Disease Gene Localization: The Myotonic Dystrophy Experience. *Am. J. Hum. Genet.* 55, A932.
49. Raff, M. C., Barres, B. A., Burne, J. F., Coles, H. S., Ishizaki, Y., and Jacobson, M. D. (1993). Programmed Cell Death and the Control of Cell Survival: Lessons from the Nervous System. *Science* 262:695–698.
50. Roy, N., McLean, M., Johnston, A., Lefebvre, C., Salih M., Yaraghi, Z., Ikeda, J. E., Korneluk, R. G., MacKenzie, A. E. (1994) Refined physical map of the spinal muscular atrophy gene region at 5q13 based on YAC and cosmid contiguous arrays, *Genomics*, (submitted).
51. Sambrook, J., Fritsch, E. F., and Maniatis, T. (1989). "Molecular Cloning: A Laboratory Manual," 2nd ed., Cold Spring Harbor Laboratory Press, Cold Spring Harbor
52. Sarnat, H. B. (1992) Cerebral dysgenesis: Embryology and clinical expression, Oxford University Press, p. 107.
53. Scherer, S. and Tsui, L.-C. (1991). Adolph, K. W., ed Cloning and analysis of large DNA molecules. Advanced Techniques in Chromosome Research. Dekker, New York. pp.33–72.
54. Soares, V. M., L. M., Kleyn, P. W., Knowles, J. A., Palmer, D. A., Asokan, S., Penchaszadeh, G.K., Munsat, T. L. and Gilliam, T. C. (1993). Refinement of the spinal muscular atrophy locus to the interval between DSS435 and MAPIB. *Genomics* 15: 365–371.
55. Sherrington, R., Melmer, G., Dixon, M., Curtis, D., Mankoo, B., Kalsi, G. and Gurling, H. (1991). Linkage disequilibrium between two highly polymorphic microsatellites. *Ani. Hum. Genet.* 49: 966–971.
56. Shutler, G., Korneluk, R. G., Tsilfidis, C., Mahadaven, M., Bailly, J., Smeets, H., Jansen, G., Wieringa, B., Lohman, F., Asanidis, C., and de Jong, P. J. (1992). Physical mapping and cloning of the proximal segment of the Myotonic Dystrophy Gene Region. *Genomics* 13: 513–525.
57. Stahl, N., 3oulton, T. G., Farruggella, T., Ip. N.Y., Davis, Witthuhn, B. A., Quelle, F. W., Silvennoinen, O., Barbieri, G., Pellegrini, S., Ihle, J. N., and Yancopoulos, G. D. (1994). Association and Activation of Jak-Tyk Kinases by CNTF-LIF-OSM-IL-6 S Receptor Components. *Science* 263, 92–95.
58. Stallings, R. L., Doggett, N. A., Okumura, K. and Ward, D. C. (1992). Chromosome 16-specific repetitive DNA sequences that map to chromosomal regions known to undergo breakage/rearrangement in leukemia cells. *Genomics* 13: 332–338.
59. Tagle, D. A., Collins, F. S. (1992). An optimized Alu-PCR primer pair for human-specific amplification of YACs and somatic cell hybrids. *Hum. Molec. Genet.* 1: 121–122.
60. The European Polycystic Kidney Disease Consortium (1994). The polycystic kidney disease gene encodes a 14 kb transcript and lies within a duplicated region on chromosome 16. *Cell* 77: 881–894.
61. Thompson, T. G., Morrison, K. E., Kleyn, P., Bengtsson, U., Gilliam, T. C., Davies, K. E., Wasmuth, J. J. and McPherson, J. D. (1993). High resolution physical map of the region surrounding the spinal muscular atrophy gene. *Hum. Mol. Genet.* 2: 1169–1176.
62. van der Steege, G., Cobben, J-M., Osinga, J., Schaffer, H., van Ommen, G-J. B., and Buys, C. H. C. M. A sublocus of the multicopy microsatellite marker CMS1 maps proximal to SMA as shown by recombinant analysis. *Genomics*, submitted.
63. Wirth, B., Voosen, B., Röhrig, D., Knapp, M., Piechaczek, B., Rudnik-Schöneborn. and Zerres, K. (1993). Fine mapping and narrowing of the genetic interval of the spinal muscular atrophy region by linkage studies. *Genomics* 15: 113–118.
64. Wirth, B., Pick, E., Leuter, A., Dadze, A., Voosen, B., Knapp, M., Piechaczak-Wappenschmidt, B., Rudnik-Schoneborn, S., Schonling, J., Cox, S., Spurr, N.K. and Zerres, K. (1994). Large linkage analysis in 100 families with autosomal recessive spinal muscular atrophy (SMA) and 11 CEPH families using 13 polymorphic loci in the region 5q11.2–q13.3. *Genomics* 20: 84–93.
65. Warrington, J. A., Bailey, S. K., Armstrong, E., Aprelikova, O., Alitolo, K., Dolganov, G. M., Wilcox, A. S., Sikela, J. M., Wolfe, S. F., Lovett, M., and Wasmuth, J. J. (1992). A radiation hybrid map of 18 growth factor, growth factor receptor, hormone receptor, neurotransmitter receptor genes on the distal region of the long arm of chromosome 5. *Genomics*. 13: 803–808.
66. Yaraghi, Z., Kang, X, Ikeda, J-E. and MacKenzie, A. *Hum. Mol. Genet.*, In Press.
67. Yaraghi, Z., McLean, M., Roy, N., Surh, L., Ikeda, J-E., and MacKenzie, A. E. A recombination event occuring within the two complex 5q13.1 simple tandem repeat polymorphisms suggests a telomeric mapping of spinal muscular atrophy. *Genomics*. Submitted.

The embodiments of the invention in which an exclusive property or privilege is claimed are defined as follows:

1. A human gene isolated from the Spinal Muscular Atrophy containing region of human chromosome 5q13, said gene spanning approximately 80 kb of genomic DNA and comprising a cDNA sequence having exons 1 to 17 which encodes neuronal apoptosis inhibitor protein.

2. The human gene as claimed in claim 1, wherein a deletion in at least one of said exons is causative of type I, II and III spinal muscular atrophy.

3. The human gene as claimed in claim 2, wherein a deletion of exons 5 or 6 is causative of spinal muscular atrophy.

4. The human gene as claimed in claim 3, wherein exons 5 and 6 are identified by a NotI restriction site dissecting exon 6.

5. The human gene as claimed in claim 1, wherein said cDNA comprises 17 exons of at least 5.5 kb and having a restriction map for exons 2 through 11 of FIG. 8.

6. The human gene as claimed in claim 1, wherein said cDNA comprises 17 exons of at least 5.5 kb and having a restriction map for exons 2 through 16 of FIG. 9D.

7. A purified nucleotide sequence wherein said sequence comprising genomic DNA, cDNA, antisense DNA, homologous DNA, or mRNA, is selected from at least one of the exons of the cDNA sequence SEQ ID NO:1, shown in Table 4.

8. A purified nucleotide sequence comprising at least 18 sequential nucleotides which hybridizes to at least one nucleotide sequence of claim 7.

9. The purified nucleotide sequence comprising at least 18 sequential nucleotides which is complementary to the nucleotide sequence of claim 7.

10. The purified nucleotide sequence of claim 7, wherein said sequence comprises the nucleotide sequence of any one of exons 1 to 16 of Table 4.

11. A nucleotide probe, said probe comprising a sequence of at least 18 sequential nucleotides of the sequence of claim 10.

12. The nucleotide probe as claimed in claim 11, wherein said probe comprises DNA or RNA.

13. A PCR primer comprising a sequence of at least 18 sequential nucleotides of the sequence of claim 7.

14. A cloning or expression vector containing the nucleotide sequence of claim 10.

15. The human gene of claim 1, wherein said cDNA sequence of said gene hybridizes with the probe of claim 11.

16. The human gene as claimed in claim 1, wherein exons 5 to 12 share significant homology with baculoviral inhibitor of apoptosis protein domains.

17. The human gene as claimed in claim 1, wherein said gene has a 5' UTR having a perfect duplication of a 90 bp region before exon 2 and in the region bridging exons 2 and 3 of Table 4.

18. Neuronal apoptosis inhibitor protein encoded by the human gene of claim 1.

19. The protein of claim 18, wherein said protein has an inhibitor of apoptosis domain, two potential transmembrane regions bracketing the inhibitor of apoptosis domain and a contiguous GTP binding site.

20. The protein as claimed in claim 18, wherein said protein is encoded by the nucleotide sequence of exons 1 to 16 of Table 4.

21. The protein as claimed in claim 20, wherein amino acids 185–250 encoded by exons 6, 7 and 8 are 35% homologous to amino acids 300–370 encoded by exons 10, 11 and 12.

22. A neuronal apoptosis inhibitor protein fragment of said protein of claim 18, said fragment comprising at least 15 sequential amino acids of SEQ ID NO: 2.

23. A neuronal apoptosis inhibitor protein fragment of said protein of claim 18, said fragment comprising an amino acid sequence selected from the group of amino acid sequences encoded by exons 1 to 16 of Table 4.

24. A neuronal apoptosis inhibitor protein fragment, comprising an amino acid sequence encoded by any one of exons 1 to 16 of the nucleotide sequence of claim 10.

25. The neuronal apoptosis inhibitor protein fragment as claimed in claim 20, said protein fragment having a deletion of the amino acids encoded by exons 5 or 6 causative of spinal muscular atrophy.

26. A monoclonal or polyclonal antibody which recognizes the protein as claimed in claim 20.

27. A monoclonal or polyclonal antibody which recognizes the neuronal apoptosis inhibitor protein responsible for spinal muscular atrophy.

28. A method for analyzing a biological sample to diagnose the presence or absence of at least a portion of the gene encoding neuronal apoptosis inhibitor protein or the protein, said method comprising:

i) providing a biological sample containing the Spinal Muscular Atrophy region q13 of human chromosome 5 or the neuronal apoptosis inhibitor protein;

ii) conducting a biological assay to determine the presence or absence in said biological sample of at least a member selected from the group consisting of:
a) the nucleotide sequence of exons 1 to 16 of Table 4; and
b) the amino acid sequence of exons 4 to 16 of Table 4.

29. The method of claim 28 for diagnosing the risk for a human of developing spinal muscular atrophy, said method additionally comprising assaying for mutations in the sequences of step ii).

30. The method of claim 27, wherein the presence or absence of exons 5 or 6 of group (a) are assayed.

31. The method of claim 28, said method further comprising determining the intact gene copy number of chromosome 5 which encodes neuronal apoptosis inhibitor protein.

32. The method of claim 28, wherein said biological assay comprises an assay selected from the group consisting of DNA hybridization, restriction enzyme digest, PCR amplification, mRNA detection and DNA sequencing.

33. The method of claim 32, wherein said biological assay comprises PCR amplification of exon 5 and exon 6 using PCR primers selected from the 5' region of exon 5 and the 3' region of exon 6.

* * * * *

UNITED STATES PATENT AND TRADEMARK OFFICE
CERTIFICATE OF CORRECTION

PATENT NO. : 6,020,127
DATED : February 1, 2000
INVENTOR(S) : MacKenzie et al.

It is certified that error appears in the above-identified patent and that said Letters Patent is hereby corrected as shown below:

Title page, insert the following:

--Foreign Application Priority Data

Oct. 18, 1994    United Kingdom    9421019.2

Dec. 19, 1994    Canada    2138425--.

Column 74, line 28 ,"claim 27" shoulf read --claim 29--.

Signed and Sealed this

Thirteenth Day of February, 2001

Attest:

NICHOLAS P. GODICI

Attesting Officer    Acting Director of the United States Patent and Trademark Office

SEQUENCE LISTING

<160> NUMBER OF SEQ ID NOS: 23

<210> SEQ ID NO 1
<211> LENGTH: 5502
<212> TYPE: DNA
<213> ORGANISM: Homo sapiens

<400> SEQUENCE: 1

```
ttccggctgg acgttgccct gtgtacctct tcgactgcct gttcatctac gacgaacccc      60
gggtattgac cccagacaac aatgccactt catattgcat gaagacaaaa ggtcctgtgc     120
tcacctggga cccttctgga cgttgccctg tgttcctctt cgcctgcctg ttcatctacg     180 acgaacccg ggtattgacc ccagacaaca atgccacttc atattgggga cttcgtctgg      240
gattccaagg tgcattcatt gcaaagttcc ttaaatattt tctcactgct tcctactaaa     300
ggacggacag agcatttgtt cttcagccac atactttcct tccactggcc agcattctcc     360
tctattagac tagaactgtg gataaacctc agaaaatggc cacccagcag aaagcctctg     420
acgagaggat ctcccagttt gatcacaatt tgctgccaga gctgtctgct cttctgggcc     480
tagatgcagt tcagttggca aaggaactag aagaagagga gcagaaggag cgagcaaaaa     540
tgcagaaagg ctacaactct caaatgcgca gtgaagcaaa aaggttaaag acttttgtga     600
cttatgagcc gtacagctca tggataccac aggagatggc ggccgctggg ttttacttca     660
ctggggtaaa atctgggatt cagtgcttct gctgtagcct aatcctcttt ggtgccggcc     720
tcacgagact ccccatagaa gaccacaaga ggtttcatcc agattgtggg ttccttttga     780
acaaggatgt tggtaacatt gccaagtacg acataagggt gaagaatctg aagagcaggc     840
tgagaggagg taaaatgagg taccaagaag aggaggctag acttgcatcc ttcaggaact     900
ggccatttta tgtccaaggg atatcccctt gtgtgctctc agaggctggc tttgtcttta     960
caggtaaaca ggacacggta cagtgttttt cctgtggtgg atgtttagga aattgggaag    1020
aaggagatga tccttggaag gaacatgcca aatggttccc caaatgtgaa tttcttcgga    1080
gtaagaaatc ctcagaggaa attcccagt atattcaaag ctacaaggga tttgttgaca    1140
taacgggaga acattttgtg aattcctggg tccagagaga attacctatg gcatcagctt    1200
attgcaatga cagcatcttt gcttacgaag aactacggct ggactctttt aaggactggc    1260
cccgggaatc agctgtggga gttgcagcac tggccaaagc aggtctttc tacacaggta    1320 taaaggacat cgtccagtgc tttcctgtg gagggtgttt agagaaatgg caggaaggtg    1380
atgacccatt agacgatcac accagatgtt ttcccaattg tccatttctc caaaatatga    1440
```

```
agtcctctgc ggaagtgact ccagaccttc agagccgtgg tgaactttgt gaattactgg    1500
aaaccacaag tgaaagcaat cttgaagatt caatagcagt tggtcctata gtgccagaaa    1560
tggcacaggg tgaagcccag tggtttcaag aggcaaagaa tctgaatgag cagctgagag    1620
cagcttatac cagcgccagt ttccgccaca tgtctttgct tgatatctct tccgatctgg    1680
ccacggacca cttgctgggc tgtgatctgt ctattgcttc aaaacacatc agcaaacctg    1740
tgcaagaacc tctggtgctg cctgaggtct ttggcaactt gaactctgtc atgtgtgtgg    1800
agggtgaagc tggaagtgga aagacggtcc tcctgaagaa aatagctttt ctgtgggcat    1860
ctggatgctg tccctgtta aacaggttcc agctggtttt ctacctctcc cttagttcca    1920
ccagaccaga cgaggggctg ccagtatca tctgtgacca gctcctagag aaagaaggat    1980
ctgttactga aatgtgcatg aggaacatta tccagcagtt aaagaatcag gtcttattcc    2040
ttttagatga ctacaaagaa atatgttcaa tccctcaagt cataggaaaa ctgattcaaa    2100
aaaaccactt atcccggacc tgcctattga ttgctgtccg tacaaacagg gccagggaca    2160
tccgccgata cctagagacc attctagaga tccaagcatt tccctttttat aatactgtct    2220 gtatattacg gaagctcttt tcacataata tgactcgtct gcgaaagttt atggtttact    2280
ttggaaagaa ccaaagtttg cagaagatac agaaaactcc tctctttgtg gcggcgatct    2340
gtgctcattg gtttcagtat cctttttgacc catcctttga tgatgtggct gttttcaagt    2400
cctatatgga acgcctttcc ttaaggaaca aagcgacagc tgaaattctc aaagcaactg    2460
tgtcctcctg tggtgagctg gccttgaaag gttttttttc atgttgcttt gagtttaatg    2520
atgatgatct cgcagaagca ggggttgatg aagatgaaga tctaaccatg tgcttgatga    2580
gcaaatttac agcccagaga ctaagaccat tctaccggtt tttaagtcct gccttccaag    2640
aatttcttgc ggggatgagg ctgattgaac tcctggattc agataggcag gaacatcaag    2700
atttgggact gtatcatttg aaacaaatca actcacccat gatgactgta agcgcctaca    2760
acaatttttt gaactatgtc tccagcctcc cttcaacaaa agcagggccc aaaattgtgt    2820
ctcatttgct ccattagtg gataacaaag agtcattgga gaatatatct gaaaatgatg    2880
actacttaaa gcaccagcca gaaatttcac tgcagatgca gttacttagg ggattgtggc    2940
aaatttgtcc acaagcttac ttttcaatgg tttcagaaca tttactggtt cttgccctga    3000
aaactgctta tcaaagcaac actgttgctg cgtgttctcc atttgttttg caattccttc    3060
aagggagaac actgactttg ggtgcgctta acttacagta cttttttcgac cacccagaaa    3120 gcttgtcatt gttgaggagc atccacttct caatacgagg aaataagaca tcacccagag    3180 cacattttc agttctggaa acatgttttg acaaatcaca ggtgccaact atagatcagg    3240
actatgcttc tgcctttgaa cctatgaatg aatgggagcg aaatttagct gaaaaagagg    3300
ataatgtaaa gagctatatg gatatgcagc gcagggcatc accagacctt agtactggct    3360
attggaaact ttctccaaag cagtacaaga ttccctgtct agaagtcgat gtgaatgata    3420
ttgatgttgt aggccaggat atgcttgaga ttctaatgac agttttctca gcttcacagc    3480
gcatcgaact ccatttaaac cacagcagag gctttatagaa aagcatccgc ccagctcttg    3540
agctgtctaa ggcctctgtc accaagtgct ccataagcaa gttggaactc agcgcagccg    3600
aacaggaact gcttctcacc ctgccttccc tggaatctct tgaagtctca gggacaatcc    3660
agtcacaaga ccaaatcttt cctaatctgg ataagttcct gtgcctgaaa gaactgtctg    3720
tggatctgga gggcaatata aatgtttttt cagtcattcc tgaagaattt ccaaacttcc    3780
accatatgga gaaattattg atccaaattt cagctgagta tgatccttcc aaactagttg    3840
```

-continued

```
ccagtttgcc aaattttatt tctctgaaga tattaaatct tgaaggccag caatttcctg    3900
atgaggaaac atcagaaaaa tttgcctaca ttttaggttc tcttagtaac ctggaagaat    3960
tgatccttcc tactggggat ggaatttatc gagtggccaa actgatcatc cagcagtgtc    4020
agcagcttca ttgtctccga gtcctctcat ttttcaagac tttgaatgat gacagcgtgg    4080
tggaaattgg ttaaaaatgt gtctgcaggc acacaggacg tgccttcacc cccatctgac    4140
tatgtggaaa gagttgacag tcccatggca tactcttcca atggcaaagt gaatgacaag    4200
cggttttatc cagagtcttc ctataaatcc acgccggttc ctgaagtggt tcaggagctt    4260
ccattaactt cgcctgtgga tgacttcagg cagcctcgtt acagcagcgg tggtaacttt    4320
gagacacctt caaaaagagc acctgcaaag ggaagagcag gaaggtcaaa gagaacagag    4380
caagatcact atgagacaga ctacacaact ggcggcgagt cctgtgatga gctggaggag    4440
gactggatca gggaatatcc acctatcact tcagatcaac aaagacaact gtacaagagg    4500
aattttgaca ctggcctaca ggaatacaag agcttacaat cagaacttga tgagatcaat    4560
aaagaactct cccgtttgga taagaattg gatgactata gaagaaag tgaagagtac    4620 atggctgctg ctgatgaata caatagactg aagcaagtga agggatctgc agattacaaa    4680
agtaagaaga atcattgcaa gcagttaaac agcaaattgt cacacatcaa gaagatggtt    4740
ggagactatg atagacagaa acatagaag gctgatgcca gttgtttga gaaattaagt    4800 atctgacatc tctgcaatct tctcagaagg caaatgactt tggaccataa ccccggaagc    4860
caaacctctg tgagcatcac agttttggtt gctttaatat catcagtatt gaagcatttt    4920
ataaatcgct tttgataatc aactgggctg aacactccaa ttaaggattt tatgctttaa    4980
acattggttc ttgtattaag aatgaaatac tgtttgaggt ttttaagcct taaggaagg    5040 ttctggtgtg aactaaactt tcacaccca gacgatgtct tcatacctac atgtatttgt    5100
ttgcataggt gatctcattt aatcctctca accacctttc agataactgt tatttataat    5160 cactttttc cacataagga aactgggttc ctgcaatgaa gtctctgaag tgaaactgct    5220
tgtttcctag cacacacttt tggttaagtc tgttttatga cttcattaat aataaattcc    5280
ggcatcatac agctactcct ccctaccgcc acctccacag acaccactct cctggttcca    5340
tctcctctgc tgcttctagc tccctgctct ggcttcaagg tgcgcaggac ctgcttcctt    5400
ggtgatcctc tgtagtctcc cacaccccac attatctaca aactgatgac tcctaattta    5460
catctccagc tcagacctct ccatcaatcc caacgcatac ac                      5502
```

<210> SEQ ID NO 2
<211> LENGTH: 1232
<212> TYPE: PRT
<213> ORGANISM: Homo sapiens

<400> SEQUENCE: 2

```
Met Ala Thr Gln Gln Lys Ala Ser Asp Glu Arg Ile Ser Gln Phe Asp
 1               5                  10                  15

His Asn Leu Leu Pro Glu Leu Ser Ala Leu Leu Gly Leu Asp Ala Val
                20                  25                  30

Gln Leu Ala Lys Glu Leu Glu Glu Glu Gln Lys Glu Arg Ala Lys
            35                  40                  45

Met Gln Lys Gly Tyr Asn Ser Gln Met Arg Ser Glu Ala Lys Arg Leu
        50                  55                  60

Lys Thr Phe Val Thr Tyr Glu Pro Tyr Ser Ser Trp Ile Pro Gln Glu
    65                  70                  75                  80

Met Ala Ala Ala Gly Phe Tyr Phe Thr Gly Val Lys Ser Gly Ile Gln
```

-continued

|     |     |     | 85  |     |     |     | 90  |     |     |     | 95  |     |     |
|-----|-----|-----|-----|-----|-----|-----|-----|-----|-----|-----|-----|-----|-----|

Cys Phe Cys Cys Ser Leu Ile Leu Phe Gly Ala Gly Leu Thr Arg Leu
              100                 105                 110

Pro Ile Glu Asp His Lys Arg Phe His Pro Asp Cys Gly Phe Leu Leu
            115                 120                 125

Asn Lys Asp Val Gly Asn Ile Ala Lys Tyr Asp Ile Arg Val Lys Asn
        130                 135                 140

Leu Lys Ser Arg Leu Arg Gly Gly Lys Met Arg Tyr Gln Glu Glu Glu
145                 150                 155                 160

Ala Arg Leu Ala Ser Phe Arg Asn Trp Pro Phe Tyr Val Gln Gly Ile
                165                 170                 175

Ser Pro Cys Val Leu Ser Glu Ala Gly Phe Val Phe Thr Gly Lys Gln
            180                 185                 190

Asp Thr Val Gln Cys Phe Ser Cys Gly Gly Cys Leu Gly Asn Trp Glu
        195                 200                 205

Glu Gly Asp Asp Pro Trp Lys Glu His Ala Lys Trp Phe Pro Lys Cys
210                 215                 220

Glu Phe Leu Arg Ser Lys Lys Ser Ser Glu Glu Ile Thr Gln Tyr Ile
225                 230                 235                 240

Gln Ser Tyr Lys Gly Phe Val Asp Ile Thr Gly Glu His Phe Val Asn
                245                 250                 255

Ser Trp Val Gln Arg Glu Leu Pro Met Ala Ser Ala Tyr Cys Asn Asp
            260                 265                 270

Ser Ile Phe Ala Tyr Glu Glu Leu Arg Leu Asp Ser Phe Lys Asp Trp
        275                 280                 285

Pro Arg Glu Ser Ala Val Gly Val Ala Ala Leu Ala Lys Ala Gly Leu
290                 295                 300

Phe Tyr Thr Gly Ile Lys Asp Ile Val Gln Cys Phe Ser Cys Gly Gly
305                 310                 315                 320

Cys Leu Glu Lys Trp Gln Glu Gly Asp Asp Pro Leu Asp Asp His Thr
                325                 330                 335

Arg Cys Phe Pro Asn Cys Pro Phe Leu Gln Asn Met Lys Ser Ser Ala
            340                 345                 350

Glu Val Thr Pro Asp Leu Gln Ser Arg Gly Glu Leu Cys Glu Leu Leu
        355                 360                 365

Glu Thr Thr Ser Glu Ser Asn Leu Glu Asp Ser Ile Ala Val Gly Pro
370                 375                 380

Ile Val Pro Glu Met Ala Gln Gly Glu Ala Gln Trp Phe Gln Glu Ala
385                 390                 395                 400

Lys Asn Leu Asn Glu Gln Leu Arg Ala Ala Tyr Thr Ser Ala Ser Phe
                405                 410                 415

Arg His Met Ser Leu Leu Asp Ile Ser Ser Asp Leu Ala Thr Asp His
            420                 425                 430

Leu Leu Gly Cys Asp Leu Ser Ile Ala Ser Lys His Ile Ser Lys Pro
        435                 440                 445

Val Gln Glu Pro Leu Val Leu Pro Glu Val Phe Gly Asn Leu Asn Ser
        450                 455                 460

Val Met Cys Val Glu Gly Glu Ala Gly Ser Gly Lys Thr Val Leu Leu
465                 470                 475                 480

Lys Lys Ile Ala Phe Leu Trp Ala Ser Gly Cys Cys Pro Leu Leu Asn
                485                 490                 495

Arg Phe Gln Leu Val Phe Tyr Leu Ser Leu Ser Ser Thr Arg Pro Asp
            500                 505                 510

-continued

```
Glu Gly Leu Ala Ser Ile Ile Cys Asp Gln Leu Leu Glu Lys Glu Gly
            515                 520                 525

Ser Val Thr Glu Met Cys Met Arg Asn Ile Ile Gln Gln Leu Lys Asn
530                 535                 540

Gln Val Leu Phe Leu Leu Asp Asp Tyr Lys Glu Ile Cys Ser Ile Pro
545                 550                 555                 560

Gln Val Ile Gly Lys Leu Ile Gln Lys Asn His Leu Ser Arg Thr Cys
            565                 570                 575

Leu Leu Ile Ala Val Arg Thr Asn Arg Ala Arg Asp Ile Arg Arg Tyr
            580                 585                 590

Leu Glu Thr Ile Leu Glu Ile Gln Ala Phe Pro Phe Tyr Asn Thr Val
            595                 600                 605

Cys Ile Leu Arg Lys Leu Phe Ser His Asn Met Thr Arg Leu Arg Lys
            610                 615                 620

Phe Met Val Tyr Phe Gly Lys Asn Gln Ser Leu Gln Lys Ile Gln Lys
625                 630                 635                 640

Thr Pro Leu Phe Val Ala Ala Ile Cys Ala His Trp Phe Gln Tyr Pro
            645                 650                 655

Phe Asp Pro Ser Phe Asp Asp Val Ala Val Phe Lys Ser Tyr Met Glu
            660                 665                 670

Arg Leu Ser Leu Arg Asn Lys Ala Thr Ala Glu Ile Leu Lys Ala Thr
            675                 680                 685

Val Ser Ser Cys Gly Glu Leu Ala Leu Lys Gly Phe Phe Ser Cys Cys
690                 695                 700

Phe Glu Phe Asn Asp Asp Leu Ala Glu Ala Gly Val Asp Glu Asp
705                 710                 715                 720

Glu Asp Leu Thr Met Cys Leu Met Ser Lys Phe Thr Ala Gln Arg Leu
            725                 730                 735

Arg Pro Phe Tyr Arg Phe Leu Ser Pro Ala Phe Gln Glu Phe Leu Ala
            740                 745                 750

Gly Met Arg Leu Ile Glu Leu Leu Asp Ser Asp Arg Gln Glu His Gln
            755                 760                 765

Asp Leu Gly Leu Tyr His Leu Lys Gln Ile Asn Ser Pro Met Met Thr
            770                 775                 780

Val Ser Ala Tyr Asn Asn Phe Leu Asn Tyr Val Ser Ser Leu Pro Ser
785                 790                 795                 800

Thr Lys Ala Gly Pro Lys Ile Val Ser His Leu Leu His Leu Val Asp
            805                 810                 815

Asn Lys Glu Ser Leu Glu Asn Ile Ser Glu Asn Asp Asp Tyr Leu Lys
            820                 825                 830

His Gln Pro Glu Ile Ser Leu Gln Met Gln Leu Leu Arg Gly Leu Trp
            835                 840                 845

Gln Ile Cys Pro Gln Ala Tyr Phe Ser Met Val Ser Glu His Leu Leu
850                 855                 860

Val Leu Ala Leu Lys Thr Ala Tyr Gln Ser Asn Thr Val Ala Ala Cys
865                 870                 875                 880

Ser Pro Phe Val Leu Gln Phe Leu Gln Gly Arg Thr Leu Thr Leu Gly
            885                 890                 895

Ala Leu Asn Leu Gln Tyr Phe Phe Asp His Pro Glu Ser Leu Ser Leu
            900                 905                 910

Leu Arg Ser Ile His Phe Ser Ile Arg Gly Asn Lys Thr Ser Pro Arg
            915                 920                 925

Ala His Phe Ser Val Leu Glu Thr Cys Phe Asp Lys Ser Gln Val Pro
930                 935                 940
```

-continued

```
Thr Ile Asp Gln Asp Tyr Ala Ser Ala Phe Glu Pro Met Asn Glu Trp
945                 950                 955                 960

Glu Arg Asn Leu Ala Glu Lys Glu Asp Asn Val Lys Ser Tyr Met Asp
                965                 970                 975

Met Gln Arg Arg Ala Ser Pro Asp Leu Ser Thr Gly Tyr Trp Lys Leu
            980                 985                 990

Ser Pro Lys Gln Tyr Lys Ile Pro Cys Leu Glu Val Asp Val Asn Asp
        995                 1000                1005

Ile Asp Val Val Gly Gln Asp Met Leu Glu Ile Leu Met Thr Val Phe
    1010                1015                1020

Ser Ala Ser Gln Arg Ile Glu Leu His Leu Asn His Ser Arg Gly Phe
1025                1030                1035                1040

Ile Glu Ser Ile Arg Pro Ala Leu Glu Leu Ser Lys Ala Ser Val Thr
                1045                1050                1055

Lys Cys Ser Ile Ser Lys Leu Glu Leu Ser Ala Ala Glu Gln Glu Leu
            1060                1065                1070

Leu Leu Thr Leu Pro Ser Leu Glu Ser Leu Glu Val Ser Gly Thr Ile
        1075                1080                1085

Gln Ser Gln Asp Gln Ile Phe Pro Asn Leu Asp Lys Phe Leu Cys Leu
    1090                1095                1100

Lys Glu Leu Ser Val Asp Leu Glu Gly Asn Ile Asn Val Phe Ser Val
1105                1110                1115                1120

Ile Pro Glu Glu Phe Pro Asn Phe His His Met Glu Lys Leu Leu Ile
                1125                1130                1135

Gln Ile Ser Ala Glu Tyr Asp Pro Ser Lys Leu Val Ala Ser Leu Pro
            1140                1145                1150

Asn Phe Ile Ser Leu Lys Ile Leu Asn Leu Glu Gly Gln Gln Phe Pro
        1155                1160                1165

Asp Glu Glu Thr Ser Glu Lys Phe Ala Tyr Ile Leu Gly Ser Leu Ser
    1170                1175                1180

Asn Leu Glu Glu Leu Ile Leu Pro Thr Gly Asp Gly Ile Tyr Arg Val
1185                1190                1195                1200

Ala Lys Leu Ile Ile Gln Gln Cys Gln Gln Leu His Cys Leu Arg Val
                1205                1210                1215

Leu Ser Phe Phe Lys Thr Leu Asn Asp Asp Ser Val Val Glu Ile Gly
            1220                1225                1230

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 3
atgcttggat ctctagaatg g                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 4
agcaaagaca tgtggcggaa                                                20
```

```
<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 5
ccagctccta gagaaagaag ga                                              22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 6
gaactacggc tggactcttt t                                               21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 7
ctctcagcct gctcttcaga t                                               21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 8
aaagcctctg acgagaggat c                                               21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 9
cgactgcctg ttcatctacg a                                               21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 10
tttgttctcc agccacatac t                                               21

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 11
```
catttggcat gttccttcca ag                                            22

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: PCR primer

<400> SEQUENCE: 12
gtagatgaat actgatgttt cataatt                                       27

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 13
tgccactgcc aggcaatcta a                                             21

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 14
taaacaggac acggtacagt g                                             21

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 15
catgttttaa gtctcggtgc tctg                                          24

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 16
ttagccagat gtgttggcac atg                                           23

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 17
gattctatgt gataggcagc ca                                            22

<210> SEQ ID NO 18
<211> LENGTH: 21
<212> TYPE: DNA
<213> ORGANISM: Artificial Sequence -continued

```
<220> FEATURE:
<223> OTHER INFORMATION: Description of Artificial Sequence: PCR primer

<400> SEQUENCE: 18
gccactgctc ccgatggatt a                                                    21

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 19
gctctcagct gctcattcag at                                                   22

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: PCR primer

<400> SEQUENCE: 20
acaaagttca ccacggctct g                                                    21

<210> SEQ ID NO 21
<211> LENGTH: 275
<212> TYPE: PRT
<213> ORGANISM: Cydia pomonella
<220> FEATURE:
<223> OTHER INFORMATION: Description of Artificial Sequence: PCR primer

<400> SEQUENCE: 21
```

Met Ser Asp Leu Arg Leu Glu Glu Val Arg Leu Asn Thr Phe Glu Lys
1               5                   10                  15

Trp Pro Val Ser Phe Leu Ser Pro Glu Thr Met Ala Lys Asn Gly Phe
            20                  25                  30

Tyr Tyr Leu Gly Arg Ser Asp Glu Val Arg Cys Ala Phe Cys Lys Val
        35                  40                  45

Glu Ile Met Arg Trp Lys Glu Gly Asp Pro Ala Ala Asp His Lys
    50                  55                  60

Lys Trp Ala Pro Gln Cys Pro Phe Val Lys Gly Ile Asp Val Cys Gly
65                  70                  75                  80

Ser Ile Val Thr Thr Asn Asn Ile Gln Asn Thr Thr Thr His Asp Thr
                85                  90                  95

Ile Ile Gly Pro Ala His Pro Lys Tyr Ala His Glu Ala Ala Arg Val
            100                 105                 110

Lys Ser Phe His Asn Trp Pro Arg Cys Met Lys Gln Arg Pro Glu Gln
        115                 120                 125

Met Ala Asp Ala Gly Phe Phe Tyr Thr Gly Tyr Gly Asp Asn Thr Lys
    130                 135                 140

Cys Phe Tyr Cys Asp Gly Gly Leu Lys Asp Trp Glu Pro Glu Asp Val
145                 150                 155                 160

Pro Trp Glu Gln His Val Arg Trp Phe Asp Arg Cys Ala Tyr Val Gln
                165                 170                 175

Leu Val Lys Gly Arg Asp Tyr Val Gln Lys Val Ile Thr Glu Ala Cys
            180                 185                 190

Val Leu Pro Gly Glu Asn Thr Thr Val Ser Thr Ala Ala Pro Val Ser
        195                 200                 205

```
Glu Pro Ile Pro Glu Thr Lys Ile Glu Lys Pro Gln Val Glu Asp
        210                 215                 220

Ser Lys Leu Cys Lys Ile Cys Tyr Val Glu Glu Cys Ile Val Cys Phe
225                 230                 235                 240

Val Pro Cys Gly His Val Val Ala Cys Ala Lys Cys Ala Leu Ser Val
                245                 250                 255

Asp Lys Cys Pro Met Cys Arg Lys Ile Val Thr Ser Val Leu Lys Val
                260                 265                 270

Tyr Phe Ser
        275

<210> SEQ ID NO 22
<211> LENGTH: 268
<212> TYPE: PRT
<213> ORGANISM: Orgyia pseudotsugata

<400> SEQUENCE: 22

Met Ser Ser Arg Ala Ile Gly Ala Pro Gln Glu Gly Ala Asp Met Lys
1               5                   10                  15

Asn Lys Ala Ala Arg Leu Gly Thr Tyr Thr Asn Trp Pro Val Gln Phe
            20                  25                  30

Leu Glu Pro Ser Arg Met Ala Ala Ser Gly Phe Tyr Tyr Leu Gly Arg
        35                  40                  45

Gly Asp Glu Val Arg Cys Ala Phe Cys Lys Val Glu Ile Thr Asn Trp
    50                  55                  60

Val Arg Gly Asp Asp Pro Glu Thr Asp His Lys Arg Trp Ala Pro Gln
65                  70                  75                  80

Cys Pro Phe Val Arg Asn Asn Ala His Asp Thr Pro His Asp Arg Ala
                85                  90                  95

Pro Pro Ala Arg Ser Ala Ala His Pro Gln Tyr Ala Thr Glu Ala
                100                 105                 110

Ala Arg Leu Arg Thr Phe Ala Glu Trp Pro Arg Gly Leu Lys Gln Arg
            115                 120                 125

Pro Glu Glu Leu Ala Glu Ala Gly Phe Phe Tyr Thr Gly Gln Gly Asp
        130                 135                 140

Lys Thr Arg Cys Phe Cys Cys Asp Gly Gly Leu Lys Asp Trp Glu Pro
145                 150                 155                 160

Asp Asp Ala Pro Trp Gln Gln His Ala Arg Trp Tyr Asp Arg Cys Glu
                165                 170                 175

Tyr Val Leu Leu Val Lys Gly Arg Asp Phe Val Gln Arg Val Met Thr
            180                 185                 190

Glu Ala Cys Val Val Arg Asp Ala Asp Asn Glu Pro His Ile Glu Arg
        195                 200                 205

Pro Ala Val Glu Ala Glu Val Ala Asp Asp Arg Leu Cys Lys Ile Cys
    210                 215                 220

Leu Gly Ala Glu Lys Thr Val Cys Phe Val Pro Cys Gly His Val Val
225                 230                 235                 240

Ala Cys Gly Lys Cys Ala Ala Gly Val Thr Thr Cys Pro Val Cys Arg
                245                 250                 255

Gly Gln Leu Asp Lys Ala Val Arg Met Tyr Gln Val
                260                 265

<210> SEQ ID NO 23
<211> LENGTH: 1151
<212> TYPE: PRT
<213> ORGANISM: Homo sapiens
```

-continued

<400> SEQUENCE: 23

```
Thr Arg Thr Val Asp Lys Pro Gln Lys Met Ala Thr Gln Gln Lys Ala
 1               5                  10                  15
Ser Asp Glu Arg Ile Ser Gln Phe Asp His Asn Leu Leu Pro Glu Leu
            20                  25                  30
Ser Ala Leu Leu Gly Leu Asp Ala Val Gln Leu Ala Lys Glu Leu Glu
        35                  40                  45
Glu Glu Glu Gln Lys Glu Arg Ala Lys Met Gln Lys Gly Tyr Asn Ser
    50                  55                  60
Gln Met Arg Ser Glu Ala Lys Arg Leu Lys Thr Phe Val Thr Tyr Glu
65                  70                  75                  80
Pro Tyr Ser Ser Trp Ile Pro Gln Glu Met Ala Ala Gly Phe Tyr
                85                  90                  95
Phe Thr Gly Val Lys Ser Gly Ile Gln Cys Phe Cys Ser Leu Ile
            100                 105                 110
Leu Phe Gly Ala Gly Leu Thr Arg Leu Pro Ile Glu Asp His Lys Arg
        115                 120                 125
Phe His Pro Asp Cys Gly Phe Leu Leu Asn Lys Asp Val Gly Asn Ile
    130                 135                 140
Ala Lys Tyr Asp Ile Arg Val Lys Asn Leu Lys Ser Arg Leu Arg Gly
145                 150                 155                 160
Gly Lys Met Arg Tyr Gln Glu Glu Ala Arg Leu Ala Ser Phe Arg
                165                 170                 175
Asn Trp Pro Phe Tyr Val Gln Gly Ile Ser Pro Cys Val Leu Ser Glu
            180                 185                 190
Ala Gly Phe Val Phe Thr Gly Lys Gln Asp Thr Val Gln Cys Phe Ser
        195                 200                 205
Cys Gly Gly Cys Leu Gly Asn Trp Glu Glu Gly Asp Asp Pro Trp Lys
    210                 215                 220
Glu His Ala Lys Trp Phe Pro Lys Cys Glu Phe Leu Arg Ser Lys Lys
225                 230                 235                 240
Ser Ser Glu Glu Ile Thr Gln Tyr Ile Gln Ser Tyr Lys Gly Phe Val
                245                 250                 255
Asp Ile Thr Gly Glu His Phe Val Asn Ser Trp Val Gln Arg Glu Leu
            260                 265                 270
Pro Met Ala Ser Ala Tyr Cys Asn Asp Ser Ile Phe Ala Tyr Glu Glu
        275                 280                 285
Leu Arg Leu Asp Ser Phe Lys Asp Trp Pro Arg Glu Ser Ala Val Gly
    290                 295                 300
Val Ala Ala Leu Ala Lys Ala Gly Leu Phe Tyr Thr Gly Ile Lys Asp
305                 310                 315                 320
Ile Val Gln Cys Phe Ser Cys Gly Gly Cys Leu Glu Lys Trp Gln Glu
                325                 330                 335
Gly Asp Asp Pro Leu Asp Asp His Thr Arg Cys Phe Pro Asn Cys Pro
            340                 345                 350
Phe Leu Gln Asn Met Lys Ser Ser Ala Glu Val Thr Pro Asp Leu Gln
        355                 360                 365
Ser Arg Gly Glu Leu Cys Glu Leu Leu Glu Thr Thr Ser Glu Ser Asn
    370                 375                 380
Leu Glu Asp Ser Ile Ala Val Gly Pro Ile Val Pro Glu Met Ala Gln
385                 390                 395                 400
Gly Glu Ala Gln Trp Phe Gln Glu Ala Lys Asn Leu Asn Glu Gln Leu
                405                 410                 415
```

-continued

```
Arg Ala Ala Tyr Thr Ser Ala Ser Phe Arg His Met Ser Leu Leu Asp
            420                 425                 430

Ile Ser Ser Asp Leu Ala Thr Asp His Leu Leu Gly Cys Asp Leu Ser
        435                 440                 445

Ile Ala Ser Lys His Ile Ser Lys Pro Val Gln Glu Pro Leu Val Leu
450                 455                 460

Pro Glu Val Phe Gly Asn Leu Asn Ser Val Met Cys Val Glu Gly Glu
465                 470                 475                 480

Ala Gly Ser Gly Lys Thr Val Leu Leu Lys Lys Ile Ala Phe Leu Trp
            485                 490                 495

Ala Ser Gly Cys Cys Pro Leu Leu Asn Arg Phe Gln Leu Val Phe Tyr
                500                 505                 510

Leu Ser Leu Ser Ser Thr Arg Pro Asp Glu Gly Leu Ala Ser Ile Ile
            515                 520                 525

Cys Asp Gln Leu Leu Glu Lys Glu Gly Ser Val Thr Glu Met Cys Met
530                 535                 540

Arg Asn Ile Ile Gln Gln Leu Lys Asn Gln Val Leu Phe Leu Leu Asp
545                 550                 555                 560

Asp Tyr Lys Glu Ile Cys Ser Ile Pro Gln Val Ile Gly Lys Leu Ile
            565                 570                 575

Gln Lys Asn His Leu Ser Arg Thr Cys Leu Leu Ile Ala Val Arg Thr
                580                 585                 590

Asn Arg Ala Arg Asp Ile Arg Arg Tyr Leu Glu Thr Ile Leu Glu Ile
            595                 600                 605

Gln Ala Phe Pro Phe Tyr Asn Thr Val Cys Ile Leu Arg Lys Leu Phe
    610                 615                 620

Ser His Asn Met Thr Arg Leu Arg Lys Phe Met Val Tyr Phe Gly Lys
625                 630                 635                 640

Asn Gln Ser Leu Gln Lys Ile Gln Lys Thr Pro Leu Phe Val Ala Ala
                645                 650                 655

Ile Cys Ala His Trp Phe Gln Tyr Pro Phe Asp Pro Ser Phe Asp Asp
            660                 665                 670

Val Ala Val Phe Lys Ser Tyr Met Glu Arg Leu Ser Leu Arg Asn Lys
                675                 680                 685

Ala Thr Ala Glu Ile Leu Lys Ala Thr Val Ser Ser Cys Gly Glu Leu
    690                 695                 700

Ala Leu Lys Gly Phe Phe Ser Cys Cys Phe Glu Phe Asn Asp Asp Asp
705                 710                 715                 720

Leu Ala Glu Ala Gly Val Asp Glu Asp Leu Thr Met Cys Leu
                725                 730                 735

Met Ser Lys Phe Thr Ala Gln Arg Leu Arg Pro Phe Tyr Arg Phe Leu
            740                 745                 750

Ser Pro Ala Phe Gln Glu Phe Leu Ala Gly Met Arg Leu Ile Glu Leu
    755                 760                 765

Leu Asp Ser Asp Arg Gln Glu His Gln Asp Leu Gly Leu Tyr His Leu
770                 775                 780

Lys Gln Ile Asn Ser Pro Met Met Thr Val Ser Ala Tyr Asn Asn Phe
785                 790                 795                 800

Leu Asn Tyr Val Ser Ser Leu Pro Ser Thr Lys Ala Gly Pro Lys Ile
                805                 810                 815

Val Ser His Leu Leu His Leu Val Asp Asn Lys Glu Ser Leu Glu Asn
            820                 825                 830

Ile Ser Glu Asn Asp Asp Tyr Leu Lys His Gln Pro Glu Ile Ser Leu
    835                 840                 845
```

-continued

```
Gln Met Gln Leu Leu Arg Gly Leu Trp Gln Ile Cys Pro Gln Ala Tyr
    850             855             860
Phe Ser Met Val Ser Glu His Leu Leu Val Leu Ala Leu Lys Thr Ala
865             870             875             880
Tyr Gln Ser Asn Thr Val Ala Ala Cys Ser Pro Phe Val Leu Gln Phe
            885             890             895
Leu Gln Gly Arg Thr Leu Thr Leu Gly Ala Leu Asn Leu Gln Tyr Phe
        900             905             910
Phe Asp His Pro Glu Ser Leu Ser Leu Leu Arg Ser Ile His Phe Ser
        915             920             925
Ile Arg Gly Asn Lys Thr Ser Pro Arg Ala His Phe Ser Val Leu Glu
    930             935             940
Thr Cys Phe Asp Lys Ser Gln Val Pro Thr Ile Asp Gln Asp Tyr Ala
945             950             955             960
Ser Ala Phe Glu Pro Met Asn Glu Trp Glu Arg Asn Leu Ala Glu Lys
            965             970             975
Glu Asp Asn Val Lys Ser Tyr Met Asp Met Gln Arg Arg Ala Ser Pro
            980             985             990
Asp Leu Ser Thr Gly Tyr Trp Lys Leu Ser Pro Lys Gln Tyr Lys Ile
        995             1000            1005
Pro Cys Leu Glu Val Asp Val Asn Asp Ile Asp Val Val Gly Gln Asp
    1010            1015            1020
Met Leu Glu Ile Leu Met Thr Val Phe Ser Ala Ser Gln Arg Ile Glu
1025            1030            1035            1040
Leu His Leu Asn His Ser Arg Gly Phe Ile Glu Ser Ile Arg Pro Ala
            1045            1050            1055
Leu Glu Leu Ser Lys Ala Ser Val Thr Lys Cys Ser Ile Ser Lys Leu
        1060            1065            1070
Glu Leu Ser Ala Ala Glu Gln Glu Leu Leu Thr Leu Pro Ser Leu
        1075            1080            1085
Glu Ser Leu Glu Val Ser Gly Thr Ile Gln Ser Gln Asp Gln Ile Phe
    1090            1095            1100
Pro Asn Leu Asp Lys Phe Leu Cys Leu Lys Glu Leu Ser Val Asp Leu
1105            1110            1115            1120
Glu Gly Asn Ile Asn Val Phe Ser Val Ile Pro Glu Glu Phe Pro Asn
            1125            1130            1135
Phe His His Met Glu Lys Leu Leu Ile Gln Ile Ser Ala Glu Ser
            1140            1145            1150
```